US008759055B2

(12) United States Patent
Heller et al.

(10) Patent No.: US 8,759,055 B2
(45) Date of Patent: *Jun. 24, 2014

(54) MINIATURE BIOLOGICAL FUEL CELL THAT IS OPERATIONAL UNDER PHYSIOLOGICAL CONDITIONS, AND ASSOCIATED DEVICES AND METHODS

(75) Inventors: Adam Heller, Austin, TX (US); Nicholas Mano, Austin, TX (US); Hyug-Han Kim, Chungnam (KR); Yongchao Zhang, Austin, TX (US); Fei Mao, Fremont, CA (US); Ting Chen, Austin, TX (US); Scott C. Barton, Austin, TX (US)

(73) Assignee: Abbott Diabetes Care Inc., Alameda, CA (US)

( * ) Notice: Subject to any disclaimer, the term of this patent is extended or adjusted under 35 U.S.C. 154(b) by 1048 days.

This patent is subject to a terminal disclaimer.

(21) Appl. No.: 12/020,459

(22) Filed: Jan. 25, 2008

(65) Prior Publication Data

US 2008/0118782 A1 May 22, 2008

Related U.S. Application Data

(63) Continuation of application No. 10/427,113, filed on May 1, 2003, now Pat. No. 7,368,190.

(60) Provisional application No. 60/377,886, filed on May 2, 2002.

(51) Int. Cl.
| | |
|---|---|
| *C12N 11/18* | (2006.01) |
| *C12Q 1/26* | (2006.01) |
| *C12Q 1/32* | (2006.01) |
| *G01N 33/72* | (2006.01) |
| *H01M 8/16* | (2006.01) |

(52) U.S. Cl.
CPC . *H01M 8/16* (2013.01); *C12Q 1/26* (2013.01); *C12Q 1/32* (2013.01); *G01N 33/723* (2013.01); *Y02E 60/527* (2013.01)
USPC .......................................................... 435/175

(58) Field of Classification Search
None
See application file for complete search history.

(56) References Cited

U.S. PATENT DOCUMENTS

| | | | |
|---|---|---|---|
| 3,774,243 A | 11/1973 | Ng et al. |
| 3,811,950 A | 5/1974 | Avampato et al. |
| 3,861,397 A | 1/1975 | Rao et al. |
| 4,117,202 A | 9/1978 | Beck |
| 4,224,125 A | 9/1980 | Nakamura et al. |
| 4,431,004 A | 2/1984 | Bessman et al. |
| 4,490,464 A | 12/1984 | Gorton et al. |
| 4,581,336 A | 4/1986 | Malloy et al. |
| 4,806,468 A | 2/1989 | Wagner et al. |
| 4,820,399 A | 4/1989 | Senda et al. |
| 4,820,636 A | 4/1989 | Hill et al. |
| 5,126,247 A | 6/1992 | Palmer et al. |
| 5,262,035 A | 11/1993 | Gregg et al. |
| 5,262,305 A | 11/1993 | Heller et al. |
| 5,264,104 A | 11/1993 | Gregg et al. |
| 5,320,725 A | 6/1994 | Gregg et al. |
| 5,356,786 A | 10/1994 | Heller et al. |
| 5,478,754 A | 12/1995 | Brandt et al. |
| 5,506,144 A | 4/1996 | Sundrehagen et al. |
| 5,593,852 A | 1/1997 | Heller et al. |
| 5,609,749 A | 3/1997 | Yamauchi et al. |
| 5,639,672 A | 6/1997 | Burd et al. |
| 5,651,869 A | 7/1997 | Yoshioka et al. |
| 5,665,222 A | 9/1997 | Heller et al. |
| 5,804,401 A | 9/1998 | Gardiol et al. |
| 5,807,747 A | 9/1998 | Wallworth et al. |
| 5,837,546 A | 11/1998 | Allen et al. |
| 5,888,787 A | 3/1999 | Chen et al. |
| 5,906,921 A | 5/1999 | Ikeda et al. |

(Continued)

FOREIGN PATENT DOCUMENTS

| | | |
|---|---|---|
| DE | 301808 | 11/1917 |
| DE | 4126692 | 2/1993 |

(Continued)

OTHER PUBLICATIONS

Willner et al. "Integration of Layered Redox Proteins and Conductive Supports for Bioelectronic Applications" Angew. Chem. Int. Ed. 2000, 39, 1180-1218.*

Ohara et al. "Glucose Electrodes Based on Cross-Linked [ Os(bpy)2CI] +/2+ Complexed Poly( 1 -vinylimidazole) Films" Anal. Chem. 1003, 65, 3512-3517.*

Fresht, Alan "The Structure and mechanism in protein science: a guide to enzyme catalysis and protein folding" Book, 1999 WH Freeman pp. 473 and 474.*

(Continued)

*Primary Examiner* — Thane Underdahl
(74) *Attorney, Agent, or Firm* — Edward J. Baba; Khin K. Chin; Bozicevic, Field & Francis LLP

(57) ABSTRACT

A fuel cell is provided with an anode and a cathode. The anode is in electrical communication with an anode enzyme and the cathode is in electrical communication with a cathode enzyme. The anode enzyme is preferably an oxidase or a dehydrogenase. The cathode enzyme is a copper-containing enzyme, such as a lacasse, an ascorbate oxidase, a ceruloplasmine, or a bilirubin oxidase. Preferably, the cathode enzyme is operable under physiological conditions. Redox polymers serve to wire the anode enzyme to the anode and the cathode enzyme to the cathode. The fuel cell can be very small in size because it does not require a membrane, seal, or case. The fuel cell can be used in connection with a biological system, such as a human, as it may operate at physiological conditions. By virtue of its size and operability at physiological conditions, the fuel cell is of particular interest for applications calling for a power source implanted in a human body, such as a variety of medical applications.

15 Claims, 11 Drawing Sheets

(56) References Cited

U.S. PATENT DOCUMENTS

| | | | |
|---|---|---|---|
| 5,972,199 | A | 10/1999 | Heller et al. |
| 6,054,039 | A | 4/2000 | Shieh |
| 6,103,033 | A | 8/2000 | Say et al. |
| 6,120,676 | A | 9/2000 | Heller et al. |
| 6,134,461 | A | 10/2000 | Say et al. |
| 6,143,164 | A | 11/2000 | Heller et al. |
| 6,174,734 | B1 | 1/2001 | Ito et al. |
| 6,175,752 | B1 | 1/2001 | Say et al. |
| 6,262,264 | B1 | 7/2001 | Buck, Jr. et al. |
| 6,294,062 | B1 | 9/2001 | Buck, Jr. et al. |
| 6,294,281 | B1 | 9/2001 | Heller |
| 6,338,790 | B1 | 1/2002 | Feldman et al. |
| 6,352,824 | B1 | 3/2002 | Buck, Jr. et al. |
| 6,399,293 | B1 | 6/2002 | Pachl et al. |
| 6,436,255 | B2 | 8/2002 | Yamamoto et al. |
| 6,500,571 | B2 | 12/2002 | Libertore et al. |
| 6,531,239 | B2 | 3/2003 | Heller |
| 6,599,407 | B2 | 7/2003 | Taniike et al. |
| 6,740,215 | B1 | 5/2004 | Nakaminami et al. |
| 6,746,582 | B2 | 6/2004 | Heller et al. |
| 6,766,817 | B2 | 7/2004 | da Silva |
| 6,885,196 | B2 | 4/2005 | Taniike et al. |
| 6,918,404 | B2 | 7/2005 | da Silva |
| 7,018,755 | B2 | 3/2006 | Ikegami et al. |
| 7,066,586 | B2 | 6/2006 | da Silva |
| 7,238,442 | B2 | 7/2007 | Heller |
| 2002/0172992 | A1 | 11/2002 | Heller |
| 2003/0152823 | A1 | 8/2003 | Heller |
| 2008/0044721 | A1 | 2/2008 | Heller et al. |

FOREIGN PATENT DOCUMENTS

| | | |
|---|---|---|
| DE | 4314417 | 11/1994 |
| DE | 4344646 | 6/1995 |
| EP | 0745843 | 12/1996 |
| JP | 55-78242 | 6/1980 |
| JP | 57-12359 | 1/1982 |
| WO | WO 89/06802 | 7/1989 |
| WO | WO 02/06828 | 1/2002 |

OTHER PUBLICATIONS

Cook, Paul "Enzyme mechanism for isotope effects" book, 1991 CRC press pp. 351-352.*

J. Stenesh "Biochemistry", published 1998, Plenum Press, New York, p. 223.* thefreedictionary.com "membrane" 3 pages, accessed Aug. 12, 2013 at http://www.thefreedictionary.com/p/membrane.*

Alkire, et al., "Current Distribution in a Tubular Electrode under Liminar Flow: One Electrode Reaction," J. Electrochem. Soc.: Electrochemical Science and Technology, vol. 124, No. 7, pp. 1043-1049.

Aoki, et al., "Electron Diffusion Coefficients in Hydrogels Formed of Cross-Linked Redox Polymers," The Journal of Physical Chemistry. 1993, vol. 97, pp. 11014-11019.

Aoki, et al., "Effect of Quaternization on Electron Diffusion Coefficients for Redox Hyrdrogels Based on Poly(4-vinylpyridine)," The Journal of Physical Chemistry. 1995, vol. 99, No. 14, pp. 5012-5110.

Barton, et al., "Electroreduction of O2 to Water on the 'Wired' Laccase Cathode," J. Phys. Chem. B. 2001, vol. 105, pp. 11917-11921.

Barton et al., "The 'Wired' Laccase Cathode: High Current Density Electroreduction of O2 to Water at +0.7 V (NHE) at pH 5," J. Am. Chem. Soc. 2001, vol. 123, pp. 5802-5803.

Barton et al., "Electroreduction of O2 to Water at 0.6 V (SHE) at pH 7 on the 'Wired' Pleurotus Ostreatus Laccase Cathode," Biosensors and Bioelectronics. 2002, vol. 17, pp. 1071-1074.

Binyamin et al., "Mechanical and Electrochemical Characteristics of Composites of Wired Glucose Oxidase and Hydrophilic Graphite," Journal of the Electrochemical Society. 2000, vol. 147, No. 7, pp. 2780-2783.

Binyamin et al., "Stablilization of Wired Glucose Oxidase Anodes Rotating at 1000 rpm at 37° C.," Journal of the Electrochemical Society, vol. 146, No. 8, pp. 2965-2967.

Blauch et al., "Effects of Long-Range Electron Transfer on Charge Transport in Static Assemblies of Redox Centers," The Journal of Physical Chemistry. 1993, vol. 97, No. 24, pp. 6444-6448.

Chen et al., "A Miniature Biofuel Cell," Journal of the American Chemical Society. 2001, vol. 123, No. 35, pp. 8630-8631.

Chen et al., "In Situ Assembled Mass-Transport Controlling Micromembranes and Their Application in Implanted Amperometric Glucose Sensors," Analytical Chemistry. Aug. 15, 2000, vol. 72, No. 16, pp. 3757-3763.

Colon et al., "Cobalt Polypyridyl Complexes as Redox Mediators for Lipoamide Dehydrogenase," Electroanalysis, 1998, vol. 10, No. 9, pp. 621-627.

Greenfield et al., "Inactivation of Immobilized Glucose Oxidase by Hydrogen Peroxide," Analytical Biochemistry. 1975, vol. 65, pp. 109-124.

Heller, "Electrical Connection of Enzyme Redox Centers to Electrodes," The Journal of Physical Chemistry. 1992, vol. 96, No. 9, pp. 3579-3587.

Jaremko et al., "Advances Toward the Implantable Artificial Pancreas for Treatment of Diabetes," Diabetes Care. Mar. 1998, vol. 21, No. 3, pp. 444-450.

Jin et al., "Electron Transfer Between Cytochrome C and Copper Enzymes," Biochemistry and Bioenergetics. 1996, vol. 39, pp. 221-225.

Katakis et al., "Electrostatic Control of the Electron Transfer Enabling Binding of Recombinant Glucose Oxidase and Redox Polyelectrolytes," Journal of the American Chemical Society. 1994, vol. 116, No. 8, pp. 3617-3618.

Katz et al., "A Non-Compartmentalized Glucose I O2 Biofuel Cell by Bioengineered Electrode Surfaces," Journal of Electroanalytical Chemistry. 1999, vol. 479, pp. 64-68.

Katz et al., "A Biofuel Cell Based on Two Immiscible Solvents and Glucose Oxidase and Microperoxidase-11 Monolayer-Functionalized Electrodes," New J Chem. 1999, pp. 481-487.

Kenausis et al., "'Wiring' of Glucose Oxidase and Lactate Oxidase Within a Hydrogel Made with Poly(vinyl pyridine) Complexed with $[Os(4,4'\text{-dimethoxy-2,2'-bipyridine})_2 1]^{+2/2+}$," The Journal of the Chemical Society, Faraday Transactions 1996, vol. 92. No. 20, pp. 4131-4136.

Koroljova-Skorobogat'Ko et al., "Purification and Characterization of the Constitutive Form of Laccase from the Basidiomycete Coriolus Hirsutus and Effect of Inducers on Laccase Synthesis," Biotechnol Appl Biochem. 1998, vol. 28, pp. 47-54.

Lee et al., "Catalysis of the Reduction of Dioxygen at Graphite Electrodes Coated with Fungal Laccase A," J. Electroanal. Chem. 1984, col. 172, pp. 289-300.

De Lumley-Woodyear et al., "Polyacrylamide-Based Redox Polymer for Connecting Redox Centers of Enzymes to Electrodes," Analytical Chemistry. 1995, vol. 67, No. 8, pp. 1332-1338.

Mano et al., "A Miniature Biofuel Cell Operating in a Physiological Buffer," J Am Chem Soc. 2002, vol. 124, pp. 12962-12963.

Mano et al., "On the Relationship Between the Characteristics of Bilirubin Oxidases and O2 Cathodes Based on Their 'Wiring'," J Phys Chem B. 2002, vol. 106, pp. 8842-8848.

Mano et al., "*An Oxygen Cathode Operating in a Physiological Solution*," J. Am. Chem. Soc. 2002,124, 6480-6486.

Mano et al. "A Miniature Biofuel Cell Operating at 0.78 V," Chem Commun. 2003, pp. 518-519.

Notification of Transmittal of the International Search Report or the Declaration, mailed May 11, 2004, in International Application No. PCTNS03/13806 of TheraSense, Inc.

Notification of Transmittal of International Preliminary Examination Report, mailed Oct. 7, 2004, in International Application No. PCTIUS03113806 of TheraSense, Inc.

Ohara et al., "'Wired' Enzyme Electrodes for Amperometric Determination of Glucose or Lactate in the Presence of Interfering Substance," Analytical Chemistry. Aug. 1, 1994, vol. 66, No. 15, pp. 2451-2457.

Palmore et al., "Electro-Enzymatic Reduction of Dioxygen to Water in the Cathode Compartment of a Biofuel Cell," Journal of Electroanalytical Chemistry. 1999, vol. 464, pp. 110-117.

Palmore et al., "A Methanol/Dioxygen Biofuel Cell that uses $NAD^+$-Dependent Dehydrogenases as Catalysts: Application of an

(56) References Cited

OTHER PUBLICATIONS

Electro-Enzymatic Method to Regenerate Nicotinamide Adenine Dinucleotide at Low Overpotentials," Journal of Electroanalytical Chemistry. 1998, vol. 443, pp. 155-161.

Palmore et al., "Microbial and Enzymatic Biofuel Cells," Enzymatic Conversion of Biomass for Fuels Production, 1994, Chapter 14, pp. 271-290.

Quinn et al., "Biocompatible, Glucose-Permeable Hydrogel for in situ Coating of Implantable Biosensors," Biomaterials. 1997, vol. 18, No. 23, pp. 1665-1670.

Quinn et al., "Photo-Crosslinked Copolymers of 2-Hydroxyethyl Methacrylate, Poly(ethylene Glycol) Tetra-Acrylate and Ethylene Dimethacrylate for Improving Biocompatibility of Biosensors," Biomaterials. 1995. vol. 15. No. 5. pp. 389-396.

Rajagopalan et al., "Effect of Quaternization of the Glucose Oxidase 'Wiring' Redox Polymer on the Maximum Current Densities of Glucose Electrodes," The Journal of Physical Chemistry. 1996, vol. 100, No. 9, pp. 3719-3727.

Rajagopalan et al., "Electrical 'Wiring' of Glucose Oxidase in Electron Conducting Hydrogels," Molecular Electronics, Chapter 7, pp. 241-254.

Rao et al., "Metal-Oxygen and Glucose-Oxygen Cells for Implantable Devices," Biomedical Engineering. 1974, vol. 9, No. 3, pp. 98-102.

Santucci et al., "Unmediated Heterogeneous Electron Transfer Reaction of Ascorbate Oxidase and Laccase at a Gold Electrode," Biochem. J. 1990, vol. 332, pp. 611-615.

Sayka et al., "The Effect of Plasma Treatment on the Wettability of Substrate Materials," Solid State Technology. 1989, vol. 32, No. 5, pp. 69-70.

Service, "Can Chip Devices Keep Shrinlung?" Science. Dec. 13, 1996, vol. 274, pp. 1834-1836.

Tarasevich et al., "Electrocatalysis of Cathodic Molecular Oxygen Reduction with Biopolymers-Enzymes and Their Models," J. Electroayal. Chem. 1986, vol. 206, pp. 217-227.

Tarasevich et al., "Electrocatalysis of a Cathodic Oxygen Reduction by Laccase," Bioelectrochemistry and Bioenergetics. 1979, vol. 6, pp. 393-403.

Taylor, "'Wiring' of Glucose Oxidase Within a Hydrogel Moade with Polyvinyl Imidazole Cornplexed with $[Os-4,4'-dimethoxy-2,2'-bipyridine)Cl]^{+/2+}$," Journal of Electroanalytical Chemistry. 1995, vol. 396. pp. 511-515.

Thuesen et al., "Cyclic Voltammetry and Electrocatalysis of the Blue Copper Oxidase Polyporous Versicolor Laccase," Acta Chemica Scandinavica. 1998, vol. 52, pp. 555-562.

Trudeau et al., "Reagentless Mediated Laccase Electrode for the Detection of Enzyme Modulators," Analytical Chemistry. Mar. 1, 1997, vol. 69, No. 5, pp. 882-886.

Tsujimura et al., "Bioelectrocatalytic Reduction of Dioxygen to Water at Neutral pH Using Bilirubin Oxidase as an Enzyme and 2,2'-Azinobis (3-ethylbenzothiazolin-6-sulfonate) as an Electron Transfer Mediator." Journal of Electroanalytical Chemistry. 2001, vol. 496, pp. 69-75.

Tsujimura et al., "Glucose/02 Biofuel Cell Operating at Physiological Conditions," Electrochemistry. 2002, vol. 70, No. 12, pp. 940-942.

Vreeke et al., "Hydrogen Peroxide and β-Nicotinamide Adenine Dinucleotide Sensing Amperometric Electrodes Based on Electrical Connection of Horseradish Peroxidase Redox Centers to Electrodes Through a Three-Dimensional Electron Relaying Polymer Network," Analytical Chemistry. Dec. 15, 1992, vol. 64, No. 24, pp. 3084-3090.

Wagner et al., "Continuous Amperometric Monitoring of Glucose in a Brittle Diabetic Chimpanzee with a Miniature Subcutaneous Electrode," Proc. Natl. Acad. May 1998, vol. 95, pp. 6379-6382.

Willner et al., "A Biofuel Cell Based on Pyroloquinoline Quinone and Microperoxidase-11 Monolayer-Functionalized Electrodes," Bioelectrochemistry and Bioenergetics. 1998, vol. 44, pp. 209-214.

Willner et al., "Biofuel Cell Based on Glucose Oxidase and Microperoxidase-11 Monolayer-Functionalized Electrodes," Journal of the Chemical Society—Perkin Transactions. 1998, vol. 2, No. 8, pp. 1817-1822.

Yahiro et al., "Bioelectrochemistry I. Enzyme Utilizing Bio-Fuel Cell Studies," Biochimica et Biophysica Acta. 1964, vol. 88, pp. 375-383.

Yaropolov et al., "Electrochemical properties of Some Copper-Containing Oxidases," Bioelectrochemistry and Bioenergetics. 1996, vol. 40, pp. 49-57.

Ye et al., "High Current Density 'Wired' Quinoprotein Glucose Dhydrogenase Electrode," Analytical Chemistry. Feb. 1, 1993, vol. 65, No. 3, pp. 238-241.

Zakeeruddin et al., "Towards Mediator Design: Characterization of Tris-(4,4'-substituted-2,2'-bipyridine) Complexes of Iron(II), Ruthenium(II) and Osmium(II) as Mediators for Glucose Oxidase of *Aspergillus niger* and Other Redox Proteins," J. Electroanal. Chem. 1992. vol. 337, pp. 253-283.

(Author Unknown), "Hemoglobin Function" Ch. 3, pp. 37-60 (date unkown).

Bier, et al., "An enzymatic amplification cycle for high sensitive immunoassay", Anal. Chim, Acta, 1996, vol. 328, No. 1, pp. 27-32.

Bier, et al., "High sensitive competitive immunodetection of 2, 4-dichlorophenoxyacetic acid using enzymatic amplification with electrochemical detection", J. Anal. Chem., 1996, vol. 354, No. 7-8, pp. 861-865.

Frew, J.E., et al. Electrochemical Biosensors, Analytical Chemistry, Aug. 1, 1987, vol. 59, pp. 933A-944A.

Gorton, L; Carbon Paste Electrodes Modified with Enzymes, Tissues, and Cells, Electroanalysis, Jan. 1995, Vo. 7, pp. 23-45.

F. Lisdat, et al., "Laccase-modified thick film electrodes", (Germany) Technical Digest of the 7th International Meeting on Chemical Sensors, 1998, pp. 786-788.

Notification of Transmittal of International Preliminary Examination Report, mailed Jul. 19, 2002, in International Application No. PCTUS02/15706 of TheraSense, Inc.

Stocklein et al., Effects of organic solvents on semicontinuous immunochemical detection of coumarin derivatives, Sens. Actuators, vol. B 24(1-3), 1995, pp. 80-84.

Stocklein et al., "Laccase: A Marker Enzyme for Solvent-modified Immunoassays", Ann. N.Y. Acad. Sci., 1996, vol. 799, pp. 525-528.

Tayhas et al., Electro-enzymatic reduction of dioxygen to water in the cathode compartment of a biofuel cell, Journal of Elctroanalytical Chemistry, Mar. 19, 1999, Vo. 464, pp. 110-117.

\* cited by examiner

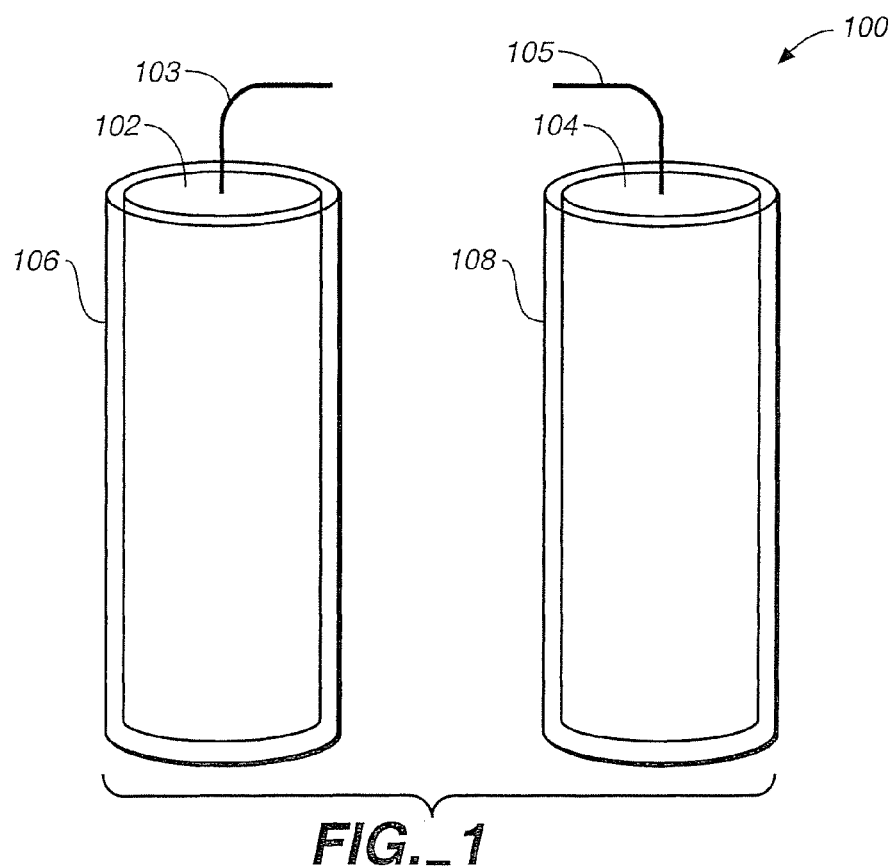
FIG._1
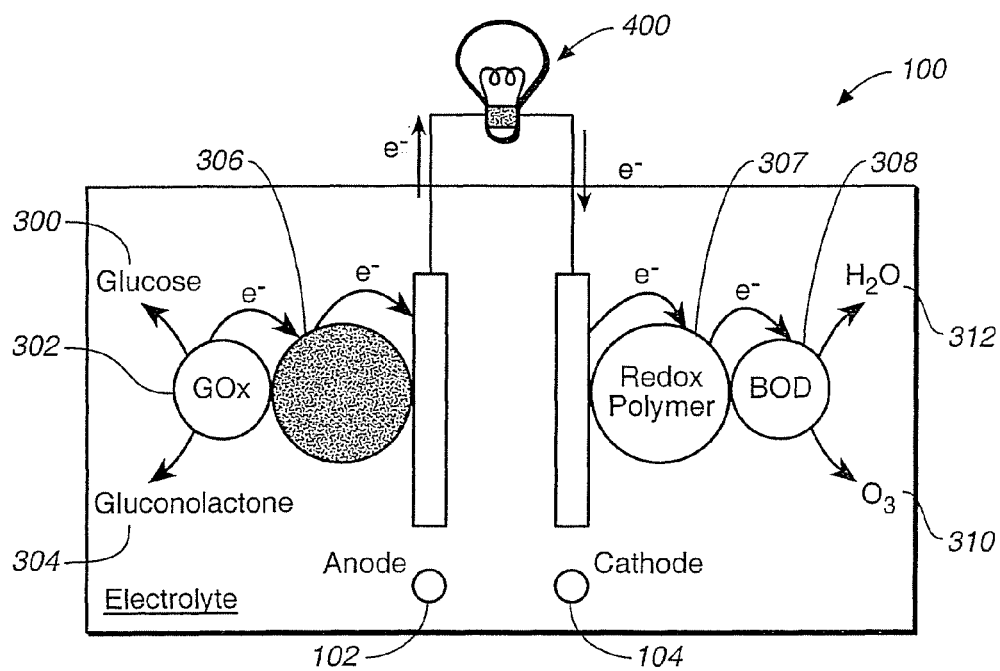
FIG._2

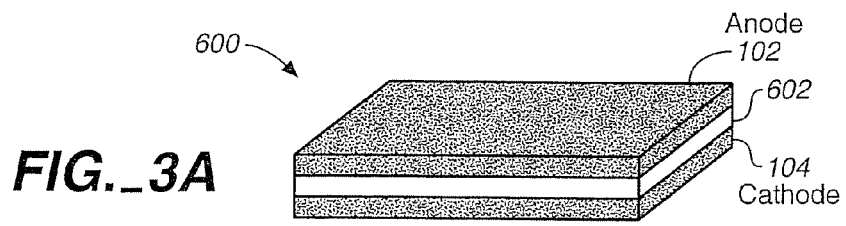
FIG._3A
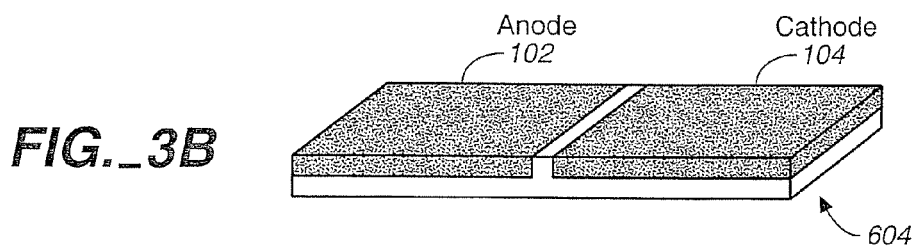
FIG._3B
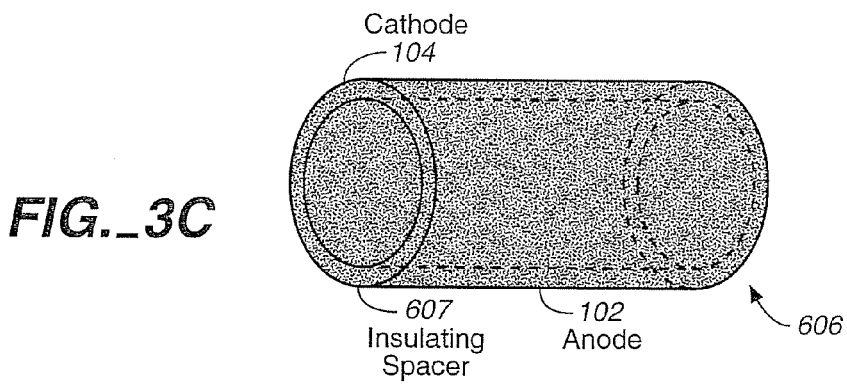
FIG._3C
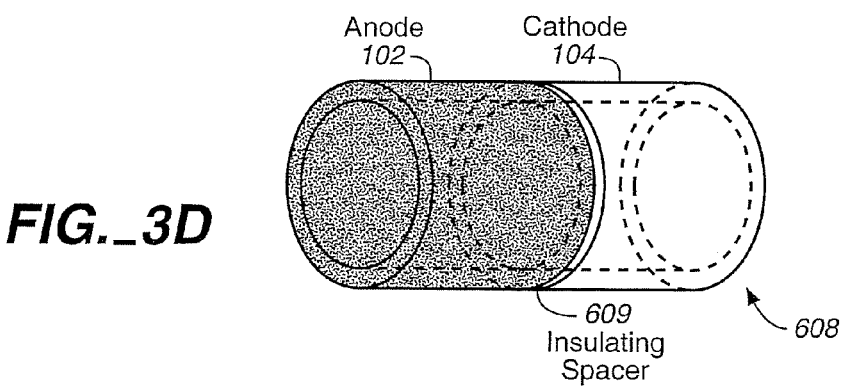
FIG._3D
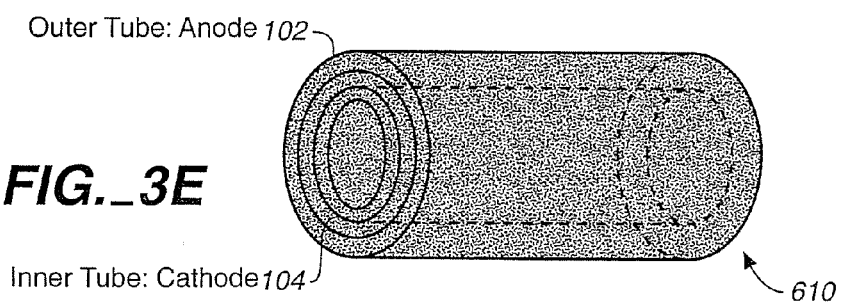
FIG._3E

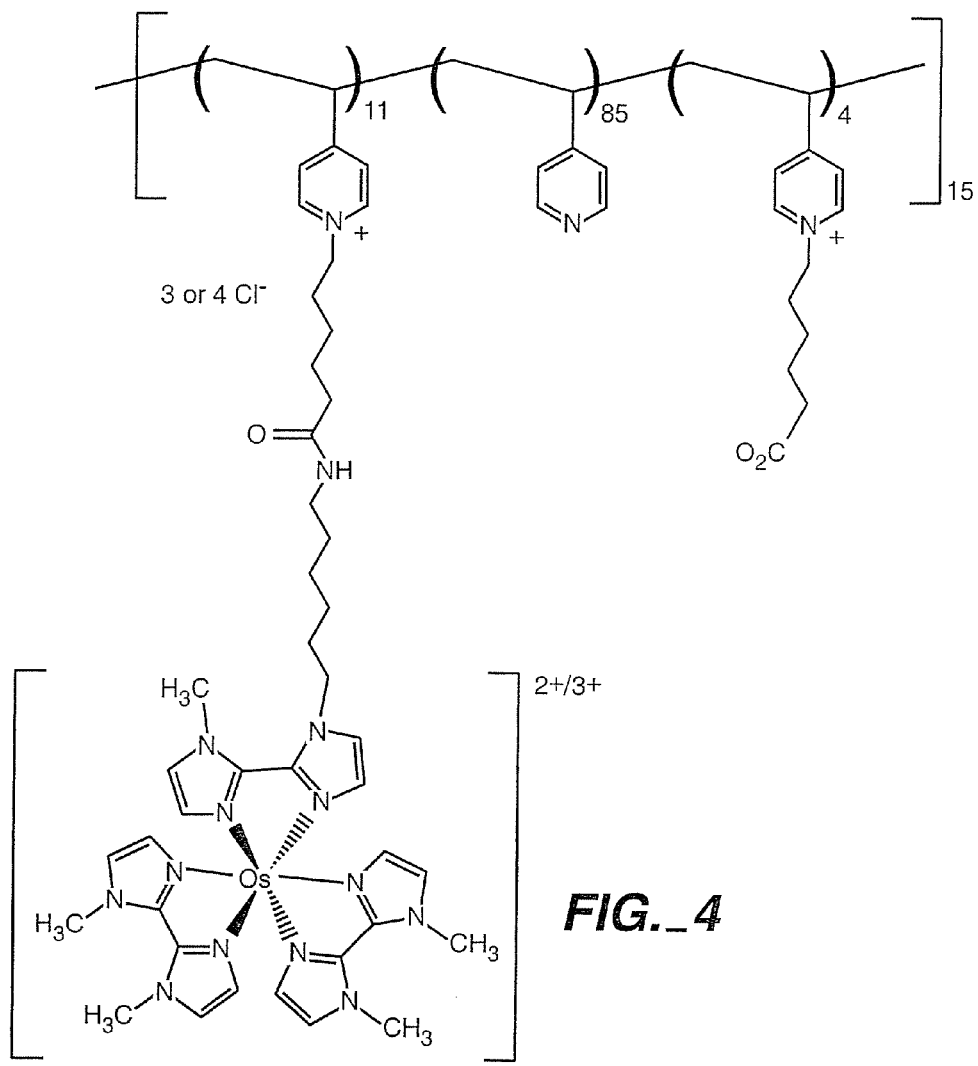
FIG._4
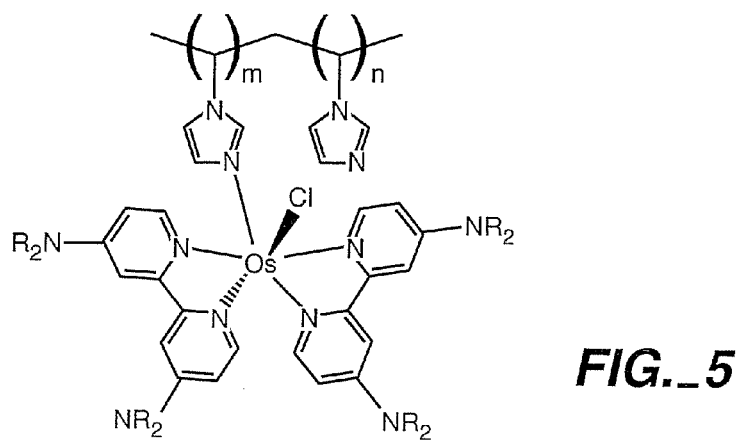
FIG._5

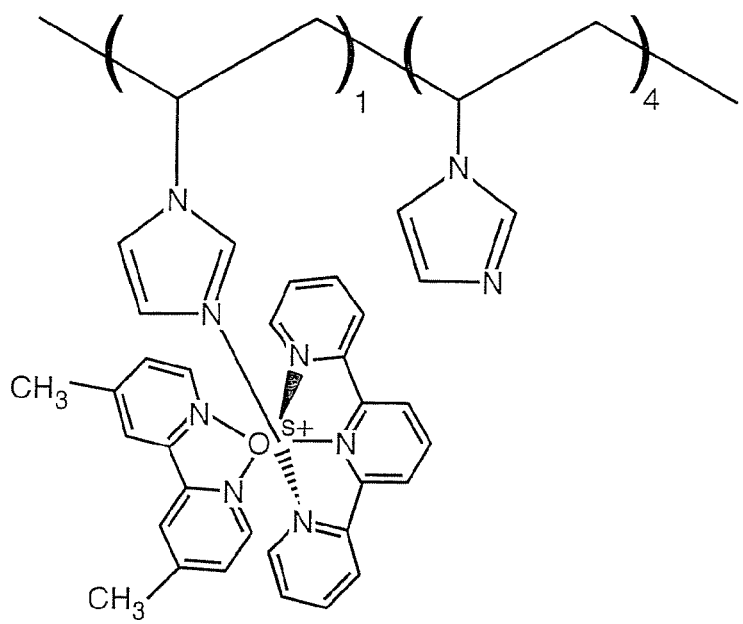
*FIG._6*
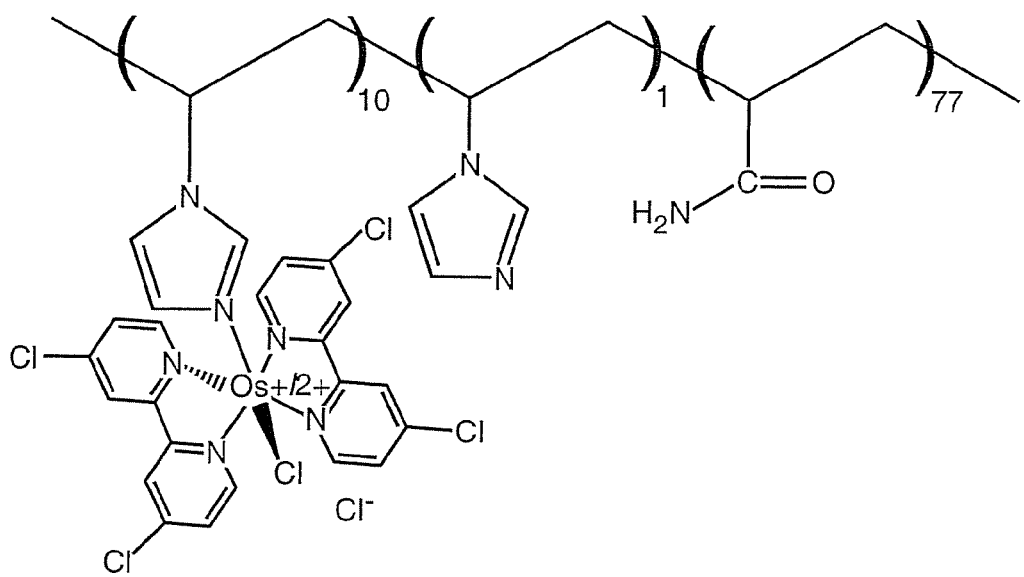
*FIG._7*

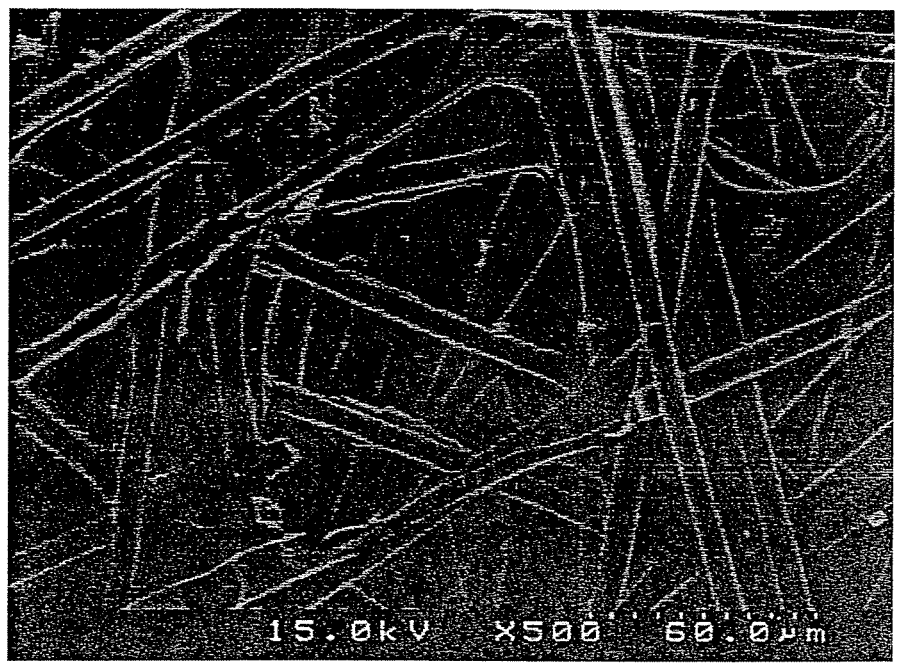
FIG._8

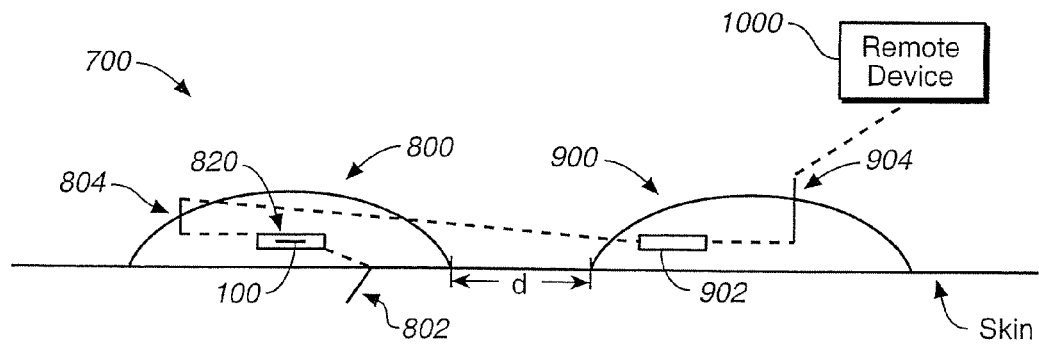
FIG._9
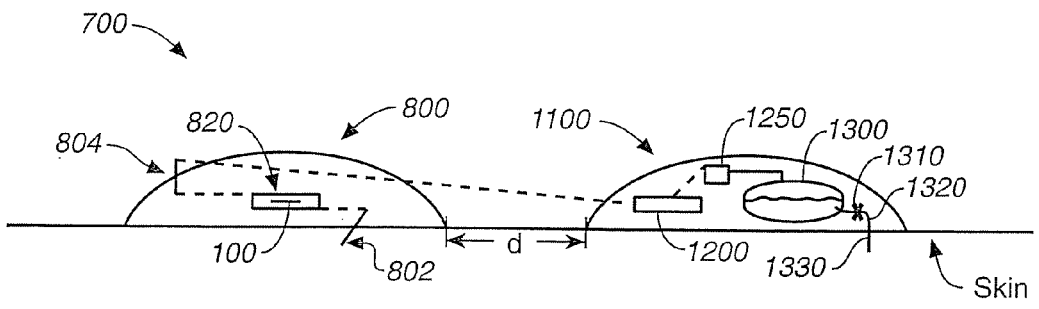
FIG._10
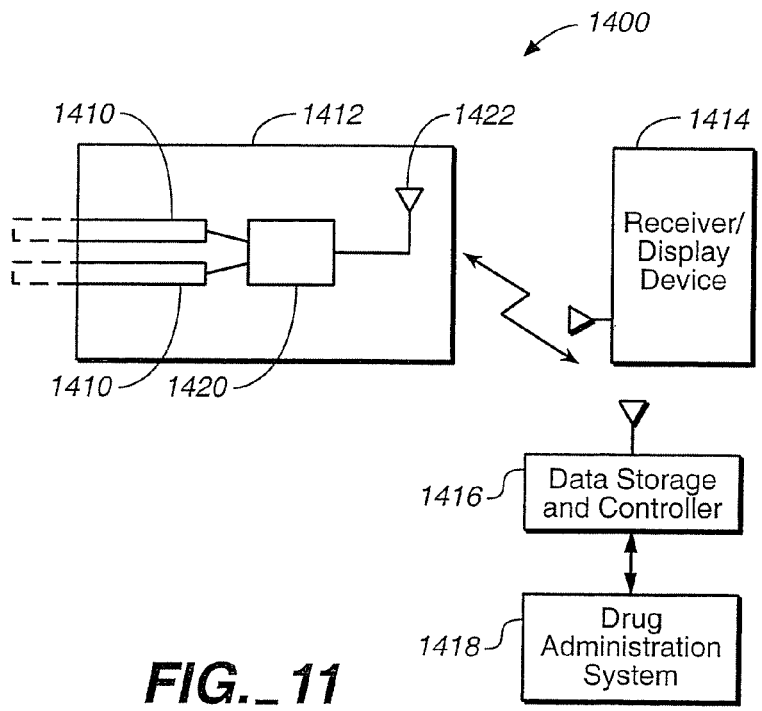
FIG._11

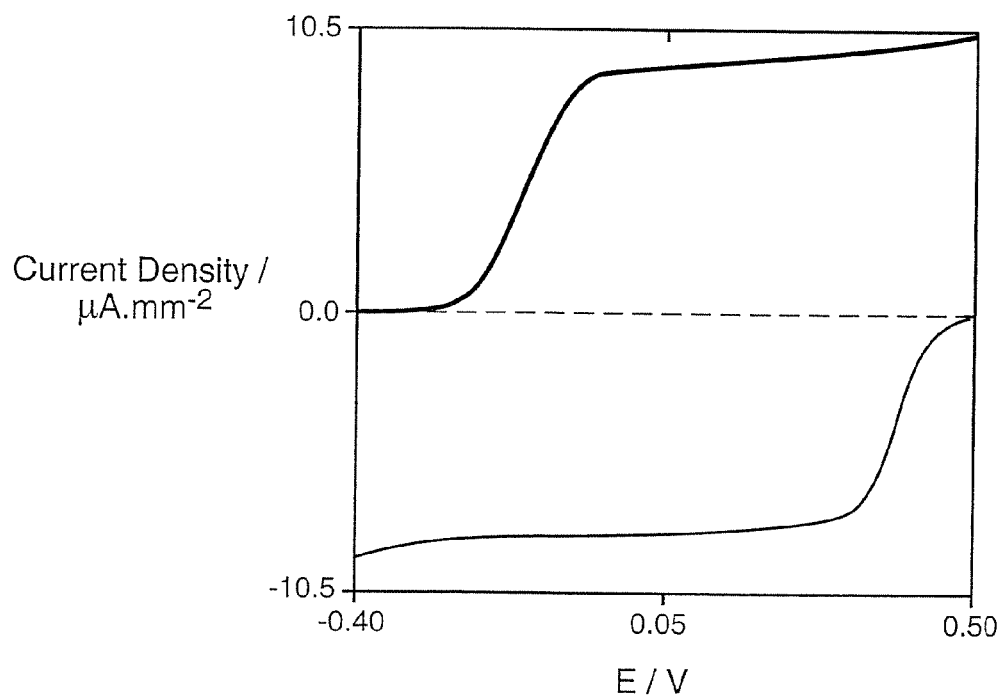
FIG._12A
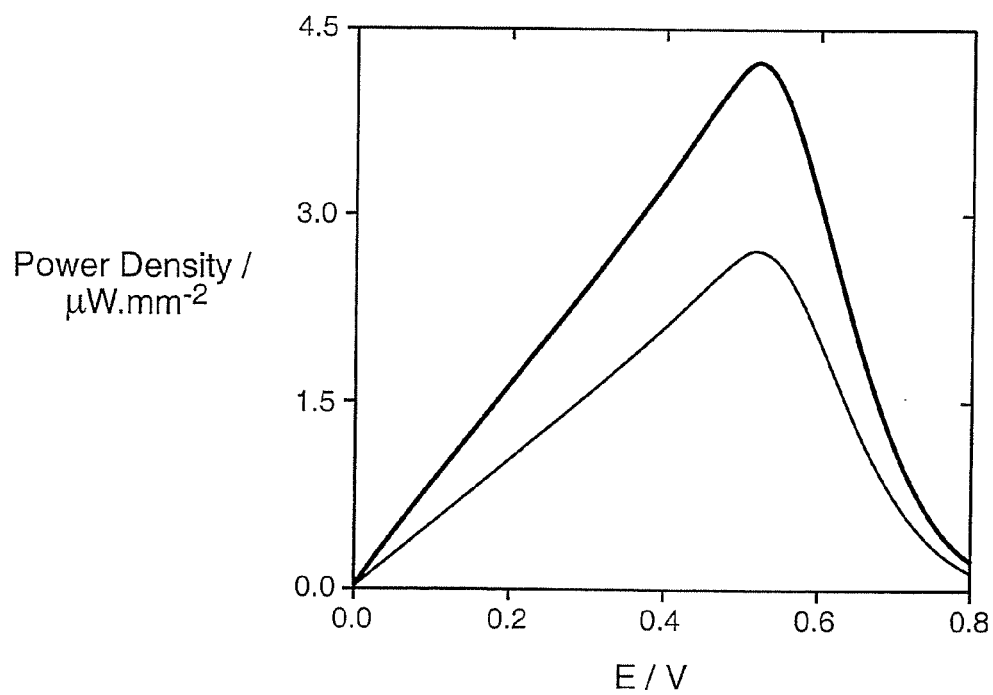
FIG._12B

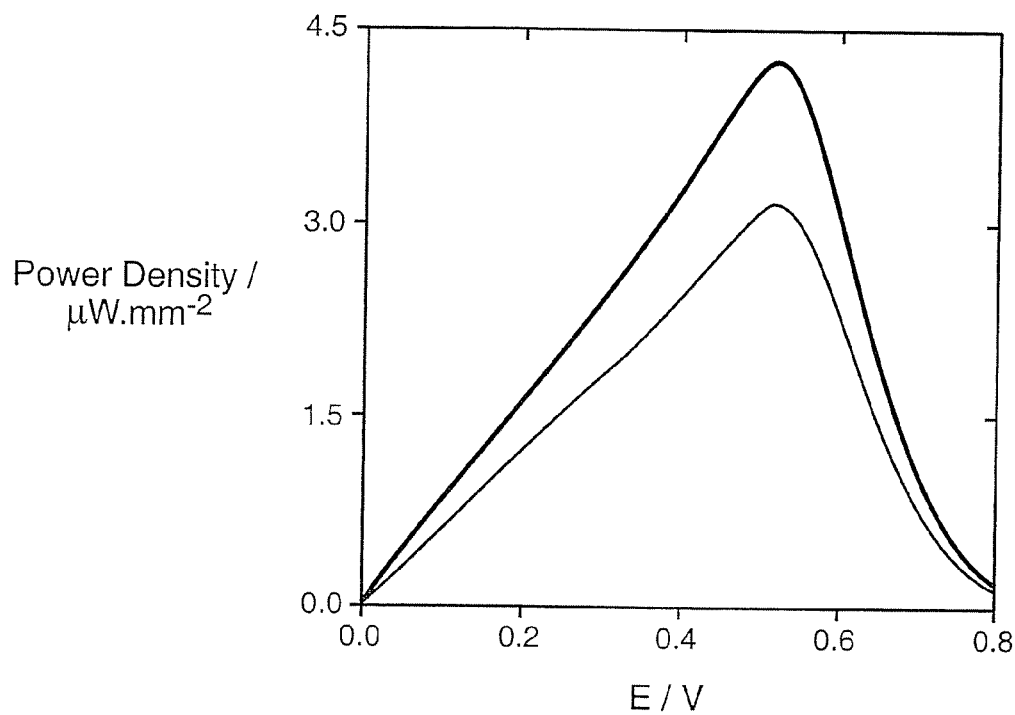
FIG._13A
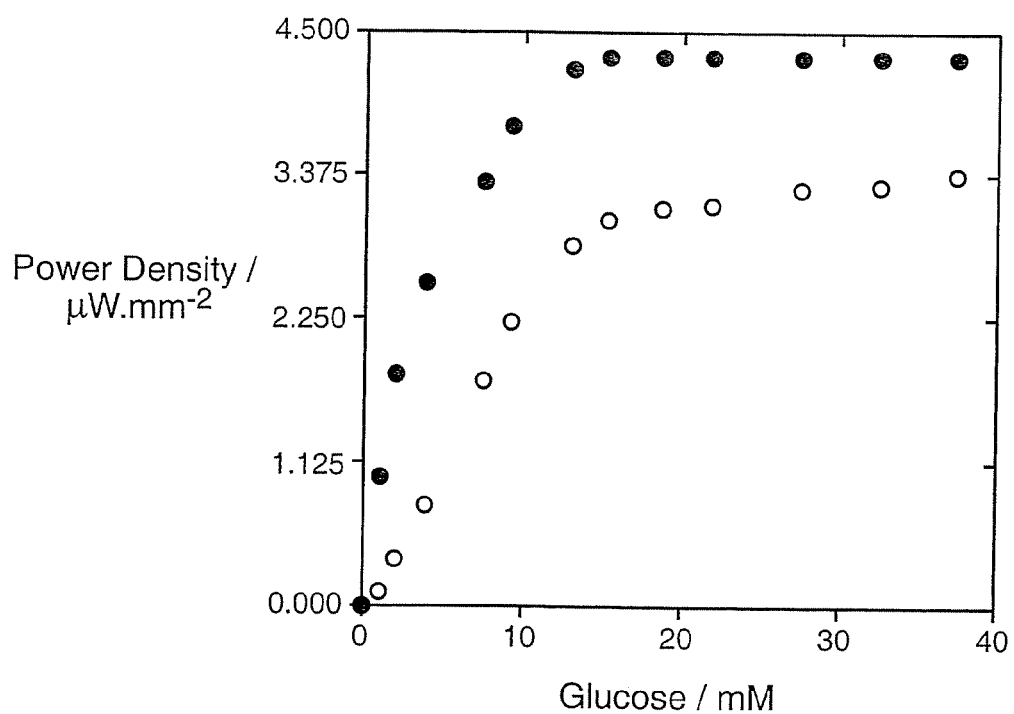
FIG._13B

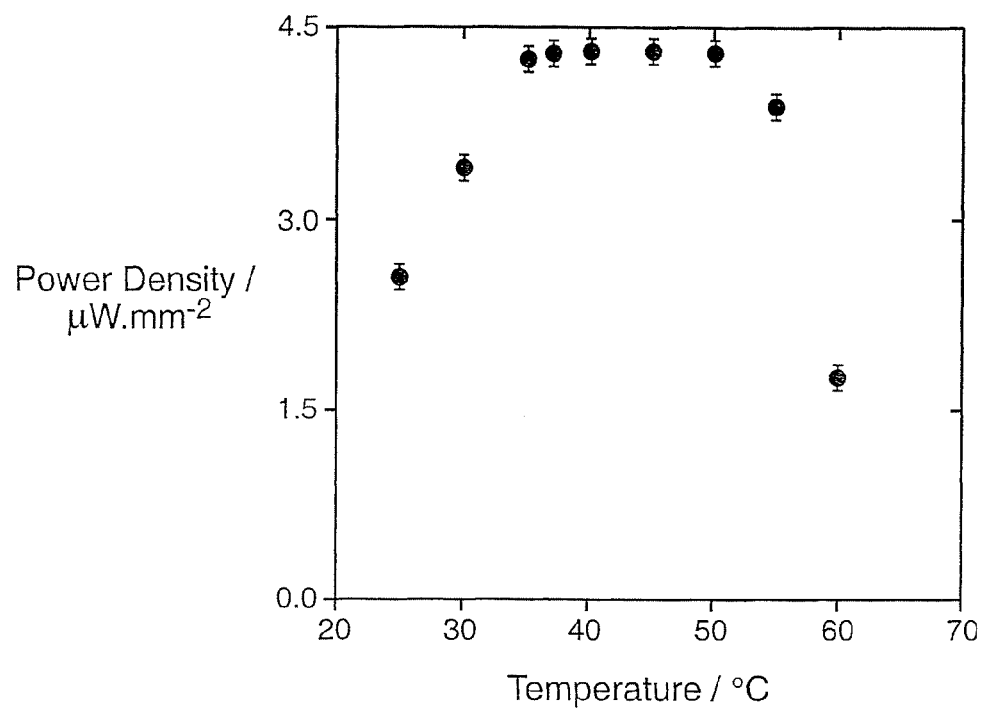
FIG._14
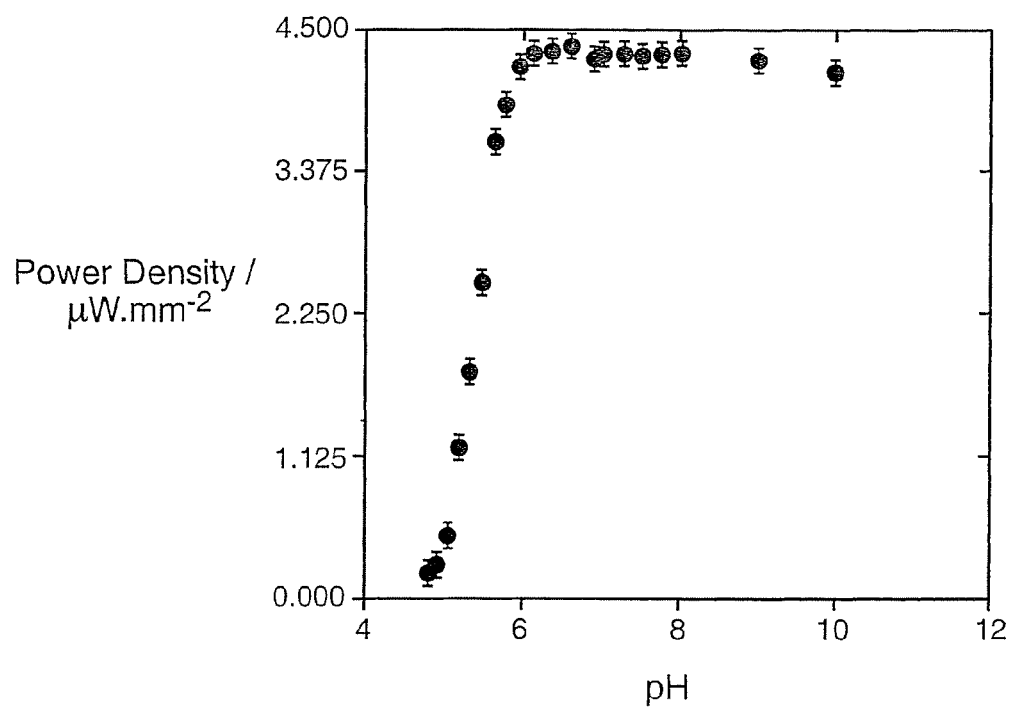
FIG._15A

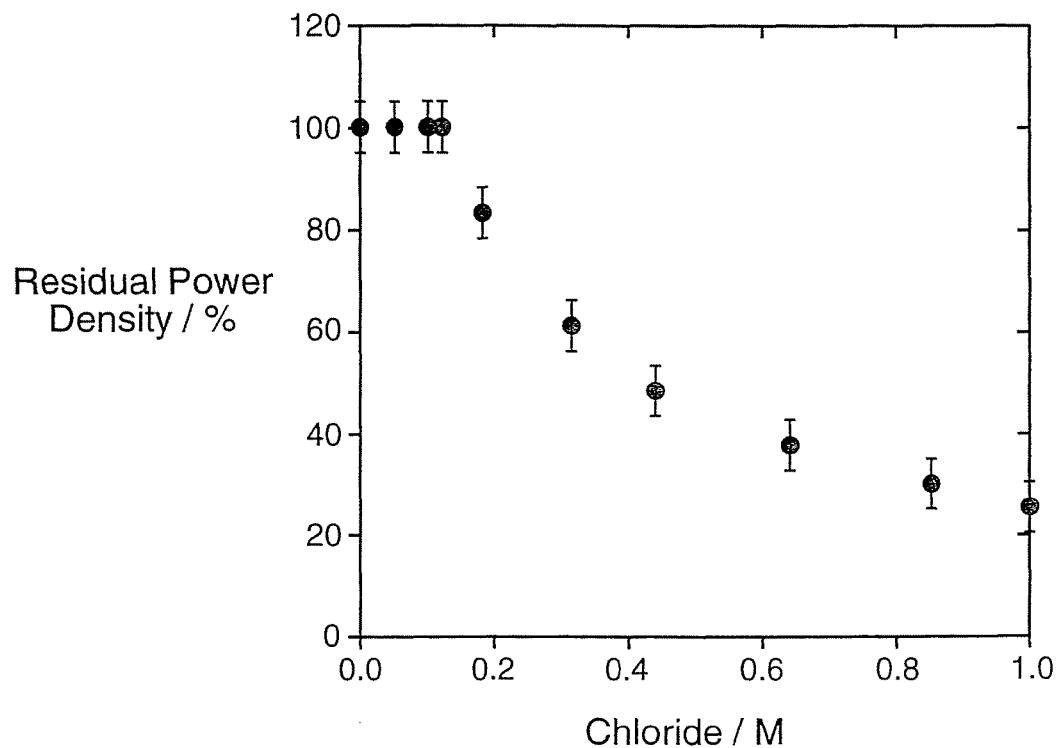
FIG._15B
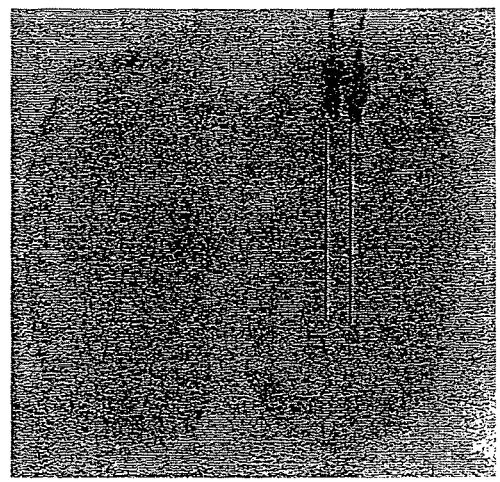
FIG._16A

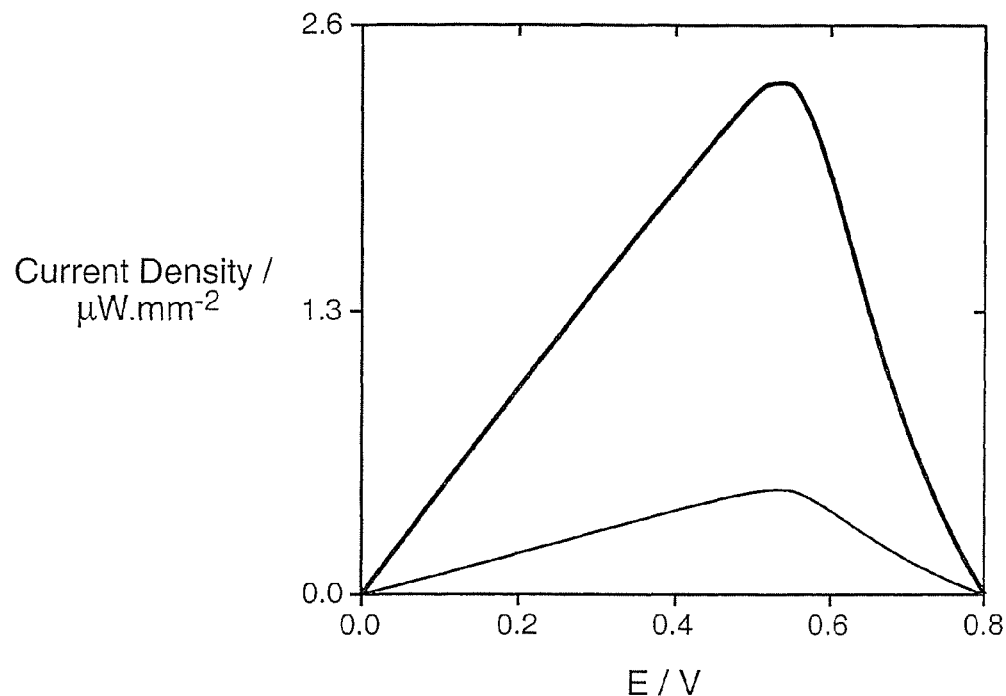
FIG._16B
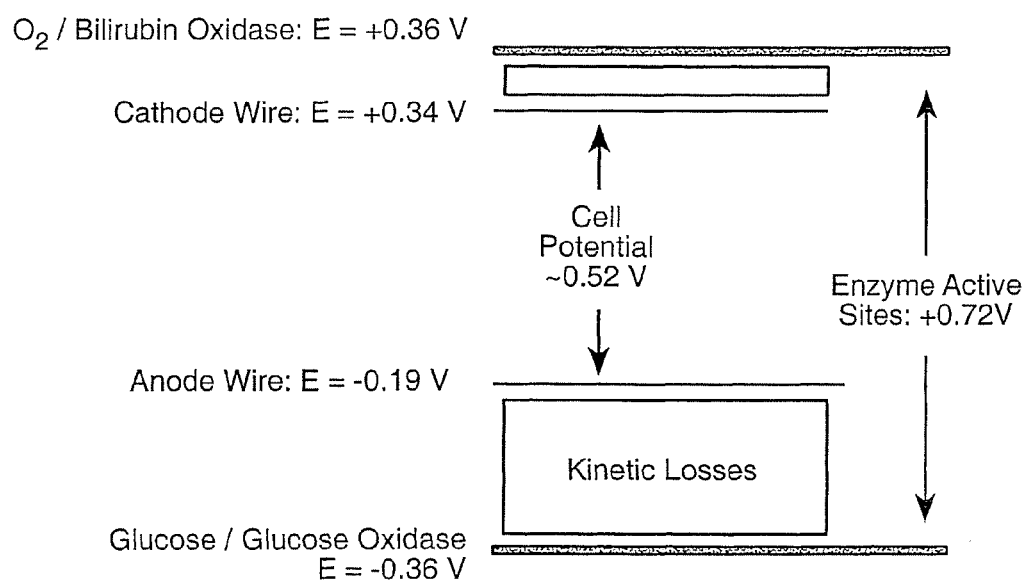
FIG._17

MINIATURE BIOLOGICAL FUEL CELL THAT IS OPERATIONAL UNDER PHYSIOLOGICAL CONDITIONS, AND ASSOCIATED DEVICES AND METHODS

CROSS-REFERENCE TO RELATED APPLICATIONS

This application claims priority to U.S. Provisional Application Ser. No. 60/377,886 of Adam Heller, Nicolas Mano, Hyug-Han Kim, Yongchao Zhang, and Fei Mao, entitled "Miniature Biological Fuel Cell That Is Operational Under Physiological Conditions," filed on May 2, 2002, which application is incorporated herein in its entirety by this reference. This application is also related to U.S. application Ser. No. 09/203,227 of Adam Heller, entitled "Biological Fuel Cell and Method," filed on Nov. 30, 1998 (with a priority claim based on U.S. Provisional Application Ser. No. 60/089,900 that was filed on Jun. 17, 1998), and issued as U.S. Pat. No. 6,294,281 on Sep. 25, 2001, and U.S. application Ser. No. 09/961,621 of Adam Heller, entitled "Biological Fuel Cell and Methods," filed on Sep. 24, 2001, and issued as U.S. Pat. No. 6,531,239 on Mar. 11, 2003, which non-provisional applications and provisional application are incorporated herein in their entireties by this reference.

STATEMENT OF FEDERAL SPONSORSHIP

Some of the research described herein was performed in connection with an Office of Naval Research grant N00014-02-1-0144 and a Defense Advanced Research Projects Agency grant N00014-97-1-1074.

FIELD OF THE INVENTION

This invention relates to electrochemical cells, and in particular, miniature biological fuel cells. More particularly, the invention relates to biological fuel cells that may be used as power sources residing within a biological system, such as an animal or a plant.

BACKGROUND OF THE INVENTION

Packages comprising autonomous electronic and electromechanical systems that are implanted in the body of animals, such as sensors and their associated electronic circuits that function to amplify the sensor signals and transmit them to a nearby receiver, require a power source. Today, these packages are powered externally by batteries. The smallest batteries are, however, much larger than the implantable sensors and their associated signal amplifier circuits. For this reason, the size of autonomous packages that include a sensor, an amplifier-transmitter, and a power source are generally defined by the battery. Batteries cannot be made as small as the sensors or amplifiers because the batteries require cases and seals, the miniaturization of which is difficult and prohibitively expensive.

Known fuel cells are also much larger than available sensors because they require a case and a seal, and usually also a membrane, which is difficult to miniaturize and seal. By way of illustration, in a conventional fuel cell, usually a membrane separates the cathode and anode compartments of the cell so as to separate electrooxidized reactant of the anodic reaction and electroreduced reactant of the cathodic reaction. If these reactants were not separated, they could react with one another, thereby reducing the power and the efficiency of the cell. As the miniaturization and sealing of membranes present difficult manufacturing issues, conventional fuel cells are generally much larger than is desirable for certain applications.

Biological fuel cells, also known as biofuel cells, have received much attention in past years. Herein, the term "biological fuel cell" or "biofuel cell" refers to an electrochemical cell having performance attributes that permit its use as a power source for an implanted device in a biological system, such as an animal, including a human, or a plant. Biological fuel cells generate electrical energy using components found in biological systems, such as sugars, alcohols, carboxylic acids, carbohydrates, starches, cellulose, and oxygen. Such devices are generally disclosed and discussed in the above-referenced U.S. Pat. Nos. 6,294,281 and 6,531,239. Miniature biofuel cells having oxygen electroreducing cathodes and glucose electrooxidizing anodes are of current interest because such cells may power future autonomous electronic and electromechanical systems implanted in a biological system, and particularly, the human body.

Numerous biofuel cells have been described in the past fifty years. However, only a few of these biofuel cells could be operated under physiological conditions, which are the conditions relevant to operation in the body of animal. Physiological conditions include, for instance, a pH of about 7.2 to 7.4, a temperature of near 37° C., and a chloride concentration of about 0.14 M. The power density of known biofuel cells is small, the typical currents per square centimeter of electrode area being less than 1 $mA/cm^2$, and usually less than 100 $\mu A/cm^2$.

Furthermore, known biofuel cells having higher power densities require ion-conducting separation membranes, such as Nafion™ membranes. These membranes are required because components of the catalysts of the anode and cathode reactions are often dissolved or reversibly adsorbed on the electrodes. Most of these known biofuel cells comprise two different dissolved or absorbed enzymes, one in the anode compartment, and the other in the cathode compartment. The most efficient of these cells also comprise diffusional redox mediators dissolved in their respective compartments. These mediators carry electrons between the electrodes and the dissolved enzymes. Because these fuel cells have limited power densities and unstable dissolved enzymes, and require membranes that are difficult to miniaturize, they have not been produced in dimensions smaller than 1 mm in length, width, or height.

As the electronic circuits and sensors used in implantable devices have become miniaturized, autonomous sensor-amplifier-transmitter devices of millimeter and sub-millimeter dimensions can be built. For example, signal amplifier circuits and sensors with footprints less under 1 $mm^2$ can be produced. The size reduction in these implantable devices is severely limited, however, by battery size and/or cost. For example, smaller batteries, such as lithium batteries of sub-millimeter dimensions, are prohibitively expensive to manufacture. Therefore, reduction in the size of implantable medical devices depends on the availability of power sources that can be miniaturized to dimensions comparable to the implantable devices themselves, and on the cost of such power sources. These factors are important, for example, in the development of autonomous medical sensors and associated transmitters, or of receivers and associated actuators.

Accordingly, the development of a miniaturized power source is desirable. Further, the development of a power source, having millimeter to sub-millimeter dimensions, is desirable. Still further, the development of a power source that can function under physiological conditions is desirable.

SUMMARY OF THE INVENTION

The present invention is directed to power sources, or fuel cells, of reduced physical dimensions. The power source of the present invention is a fuel cell that, unlike other fuel cells, can operate without a membrane. As a membrane can be eliminated as a component of the fuel cell, the dimensions of the cell can be reduced. For example, according to one aspect of the invention, the power source can have a footprint less than or equal to approximately 3 $mm^2$, and generally less than or equal to 1 $mm^2$, such as down to about 0.1 $mm^2$. This reduced size compares well with the size of conventional methanol-air or hydrogen-oxygen fuel cells, which is on the order of 10 $mm^2$ or more, and is of great advantage for a variety of applications, such as applications calling for the implantation of fuel cells in biological systems.

A membrane is rendered unnecessary in the inventive fuel cells by virtue of two special electrocatalysts, one of which is immobilized on the surface of the anode, the other of which is immobilized on the surface of the cathode. Generally, immobilization refers to the direct or indirect, entrapment of an electrocatalyst on an electrode surface or chemical binding, such as covalent, ionic, or coordinative binding, of an electrocatalyst on an electrode surface. The anode electrocatalyst is a poor catalyst for oxygen reduction and the cathode electrocatalyst is a poor catalyst for oxidation of the fuel of the cell, such as glucose. In other words, the anode electrocatalyst is so selective for the fuel of the cell, that oxygen is not rapidly electroreduced at the anode, even though the anode is poised at a potential that is much more reducing than the potential of the cathode, where oxygen is reduced. Further, the cathode electrocatalyst is so selective for oxygen, that the fuel of the cell is not rapidly electrooxidized at the cathode, even though the cathode is poised at a potential that is much more oxidizing than the potential of the anode, where the cell fuel is electrooxidized. As a result, the current loss associated with the oxidation of the cell fuel at the cathode, and the current loss associated with the reduction of oxygen at anode, are both small.

Thus, in the cell of the present invention, the rate of fuel oxidation, such as glucose oxidation, at the wired cathode, or the cathode that is in electrical communication with the immobilized cathode enzyme, such as bilirubin oxidase, is much slower than the rate of oxygen electroreduction, such that no membrane is required. This aspect differentiates the inventive fuel cell from the known methanol-air fuel cell, which requires a membrane. Further, in the cell of the present invention, the rate of oxygen electroreduction at the wired anode, or the anode that is in electrical communication with the immobilized anode enzyme, is much slower than the rate of fuel electrooxidation, such as glucose oxidation, such that no membrane is required. This aspect differentiates the inventive fuel cell from the known hydrogen-oxygen fuel cell, in which oxygen is rapidly reduced at the hydrogen anode and a membrane is required. In summary, the fuel cell of the present invention can operate with the anode and the cathode in the same compartment, in the presence of both oxygen and the fuel of the cell, such as glucose.

Not only can the fuel cell operate without cumbersome components, such as membranes, seals and cases, it can do so effectively. For example, according to one aspect of the invention, the fuel cell of the present invention can produce a current density of from about 0.1 to about 10 $mA/cm^2$, which compares well with the lower current densities associated with conventional fuel cells, such as methanol-air and hydrogen-oxygen fuel cells. In addition, the effective fuel cell of the present invention can be manufactured relatively inexpensively, such as on the order of about 10¢, per cell, which compares favorably with the manufacturing costs of conventional cells, such as methanol-air and hydrogen-oxygen fuel cells, which are on the order of more, and often considerably more, than $100. The very low cost of the inventive fuel cells is a particular advantage with respect to applications that call for fuel cells having a short life span, such as disposable fuel cells used in biological systems for medical purposes, which may be in use for only a week, or even less.

According to another aspect of the invention, the fuel cell comprises a miniature biofuel cell capable of operating under physiological conditions, or generally, a temperature of about 37° C., a pH of 7.2 to 7.4, and a NaCl concentration of about 0.14 M (although physiological temperatures may be up to about 37.5° C. and physiological NaCl concentrations may be up to about 0.15M, for example). This aspect differentiates the inventive biofuel cell from conventional methanol-air and hydrogen-oxygen fuel cells, which operate at non-physiological conditions of neutral pH and relatively high temperature, such as 70° C. to 120° C. As such, the biofuel cell of the present invention may be used within a biological system, such as a body of an animal. For example, according to a particular aspect of the invention, the biofuel cell electrooxidizes oxidizable components of a body fluid within an animal, particularly glucose or lactate components, and electroreduces oxygen within that fluid. Power is generated in the biofuel cell via the electrooxidation of glucose or lactate in the fluid, coupled with the electroreduction of oxygen in the same fluid. Advantageously, this biofuel cell is small, effective, powerful, and easy and inexpensive to manufacture.

These and other aspects, features and advantages of the present invention are described in the drawings and the description of the invention set forth below, or will be apparent or appreciated upon consideration thereof.

BRIEF DESCRIPTION OF THE DRAWINGS

FIG. 1 is a cross-sectional view of components of a biological fuel cell, according to an embodiment of the invention.

FIG. 2 is a schematic illustration of electron transfer in the electrocatalytic oxidation of glucose and in the electrocatalytic reduction of oxygen that occur in a biological fuel cell, according to an embodiment of the invention.

FIGS. 3A to 3E are illustrations of various configurations of an anode and a cathode used in a biological fuel cell, according to various embodiments of the invention.

FIG. 4 is a representation of the molecular structure of a redox polymer that can be used as an electrical coupler or "wire" in an anode electrocatalyst layer, according to an embodiment of the invention.

FIG. 5 is a representation of the molecular structure of a redox polymer that can be used as an electrical coupler or "wire" in an anode electrocatalyst layer, according to an embodiment of the invention.

FIG. 6 is a representation of the molecular structure of a redox polymer that can be used as an electrical coupler or "wire" in a cathode electrocatalyst layer, according to an embodiment of the invention.

FIG. 7 is a representation of the molecular structure of a redox polymer that can be used as an electrical coupler or "wire" in a cathode electrocatalyst layer, according to an embodiment of the invention.

FIG. 8 is a scanning electron microscope image of a composite electrode, which shows the crosslinking of a redox polymer-enzyme adduct on carbon fibers, according to an embodiment of the invention.

FIG. 9 is a schematic illustration of an analyte-monitoring device, shown in cross-section, where dashed lines represent electrical coupling of components of the device, and dotted lines represent communicative couplings between components of the device and between the device and a remote device, according to an embodiment of the invention.

FIG. 10 is a schematic illustration of an analyte-monitoring and/or treatment device, shown in cross-section, where dashed lines represent electrical coupling of components of the device and a dotted line represents a communicative coupling between components of the device, according to an embodiment of the invention.

FIG. 11 is a schematic, block-diagram illustration of an autonomous, analyte-monitoring and treatment device, which includes a drug delivery system, according to an embodiment of the invention.

FIG. 12A is a graph of current density ($\mu A/cm^2$) versus cell potential (V), which shows the polarization of an anode (in bold line) and of a cathode (in fine line) in a biological fuel cell, as described in Experimental Example 3.

FIG. 12B is a graph of power density ($\mu W/mm^2$) versus cell potential (V) at 25° C. (in fine line) and at 37° C. (in bold line) in a biological fuel cell, as described in Experimental Example 3.

FIG. 13A is a graph of power output (power density in $\mu W/mm^2$) versus cell potential (V) in air (bold line) and under oxygen (fine line) in a biological fuel cell, as described in Experimental Example 3.

FIG. 13B is a graph of power density ($\mu W/mm^2$) versus glucose concentration (mM) in air (closed circle) and under oxygen (open circle) in a biological fuel cell operating at 0.52 V, as described in Experimental Example 3.

FIG. 14 is a graph of power density ($\mu W/mm^2$) versus temperature (° C.) in a biological fuel cell operating at 0.52 V, as described in Experimental Example 3.

FIG. 15A is a graph of power density ($\mu W/mm^2$) versus pH in a biological fuel cell operating at 0.52 V, as described in Experimental Example 3.

FIG. 15B is a graph of residual power density (%) versus chloride concentration in a biological fuel cell operating at 0.52 V, as described in Experimental Example 3.

FIG. 16A shows photographs of a whole and a sliced grape with implanted fibers and associated electrical contacts, as described in Experimental Example 3. Lines are drawn to show the position of the 7-$\mu$m-diameter fibers, as they were barely visible.

FIG. 16B is a graph of power output (power density in $\mu W/mm^2$) versus cell potential (V) of the biological fuel cell associated with FIG. 16A above, where the cathode fiber is implanted near the skin of the grape (bold line) and near the center of the grape (fine line), as described in Experimental Example 3.

FIG. 17 is a schematic illustration of redox potentials (vs Ag/AgCl at pH 7.2) of enzymes and associated "wiring" redox polymers in a biological fuel cell, as described in Experimental Example 3.

DETAILED DESCRIPTION OF EMBODIMENTS

The present invention is generally directed to a biological fuel cell and more particularly directed to a biological fuel cell of reduced physical dimensions that can be used under physiological conditions. A biological fuel cell that is miniaturized according to the present invention may be used in connection with various devices, including autonomous electronic, electromechanical and microfluidic medical implants, such as sensors, transmitters, receivers, and actuators, and the like. Such devices may be reduced in size by virtue of being powered by a miniaturized biological fuel cell.

The biological fuel cell of the invention may comprise, consist essentially of, or consist of an anode and an anode enzyme in electrical communication and a cathode and a cathode enzyme in electrical communication. That is, the biological fuel cell may be based on two primary electrical connections. One electrical connection is between an anode of the biological fuel cell and a catalyzing enzyme for the oxidation of oxidizable components of a biological fluid, such as glucose or lactate. For example, glucose may be electrooxidized by the catalyzing enzyme via this first electrical connection. The other electrical connection is between a cathode of the biological fuel cell and a catalyzing enzyme, such as a copper-containing enzyme, for the reduction of oxygen. For example, oxygen may be electroreduced by the catalyzing enzyme, bilirubin oxidase (often referenced herein as BOD), via this second electrical connection.

The implantable biological fuel cell of the invention has a footprint smaller than 3 $mm^2$, preferably smaller than 1 $mm^2$, and most preferably less than or equal to about 0.3 $mm^2$, such as down to about 0.1 $mm^2$. The volume of the cell is on the order of about 1 $mm^3$ or less. The biological fuel cell can be used, for example, to power an implanted miniature sensor, or sensor/transmitter, such as a sensor of blood flow or pressure, pH, oxygen, carbon dioxide, electrolyte(s), lactate, pyruvate, glucose, creatine phosphate, creatine, creatinine, or the like. The biological fuel cell can be integrated with the sensor or other electronic device on a chip, such as an organic or a silicon-based integrated circuit, to facilitate integration and manufacture of a sensor or other device that will carry its own power source. In a preferred embodiment, none of the components of the cell is dissolved or leached at appreciable levels, in vivo, such that the components do not diffuse away from the working electrodes during the operation of the cell.

The Biological Fuel Cell

The biological fuel cell of the invention typically uses compounds available in a variety of biological systems as fuel. Generally, the cell operates in association with a biological fluid, such as blood in an animal, including a human, or sap in a plant, for example. By way of example, a biological fuel cell may be configured for implantation within a biological system, such as an animal, to operate an electrical device, such as a glucose sensor, a pacemaker, a stimulator for nerve growth, a stimulator for relief of chronic pain, a stimulator for regrowth of bone or other tissue, a drug-release valve or microvalve, a fluid-flow control valve, such as a valve in a duct or in the urinary tract, or the like. When the fuel cell is implanted in a blood vessel of an animal, biological fluid may be pumped through the fuel cell by the heart of the animal, thereby obviating any need for a mechanical pump. Further by way of example, a biological fuel cell may be configured for providing electricity from a biological system, such as a plant, including a tree, or a component of a plant, such as a plant residue or fruit, or the like, which electricity may be used to operate a device that is external to the cell or to the system in which the cell resides.

Typically, the cell operates in association with a biological fluid of an animal, such as blood, subcutaneous interstitial fluid, fluid between cells in various tissues, fluid in the peritoneum, fluid near the spinal cord, or the like. Since the biofuel cells are generally used within an animal when the animal is alive, components of the biological fluid that fuel the biofuel cell are replenished. These replenishable components serve as oxidizable fuel for the operation of the biological fuel cell, and include, without limitation, glucose, lactate, and pyruvate. Merely by way of example, other exemplary components include sugars, alcohols, carboxylic acids, carbohydrates, starches, and cellulose. Through the biofuel cell, these components are oxidized by dissolved or complexed oxygen, which is usually supplied by the blood in which it is mostly hemoglobin-bound. In other fluids, the oxygen may be more or less associated with or bound to myoglobin.

FIG. 1 illustrates components of a biological fuel cell 100, according to an embodiment of the invention. Biological fuel cell 100 is intended for use within a biological system, which provides electrolyte (as shown in FIG. 2) for the cell. The cell 100 includes two electrodes, an anode 102 and a cathode 104, which are separated to avoid electrical shorting. The separation of anode 102 from cathode 104 can be accomplished using one or more spacers (not shown). The spacers are often permeable, porous, microporous, and/or fibrous. Alternatively, the spacers can have gaps to allow fluid to flow through them. In alternate embodiments, the spacers can comprise ion-selective membranes. Suitable materials for spacers include, but are not limited to, polyamides (e.g., nylon), polyesters (e.g., Dacron™), a cation-exchange membrane (e.g., a Nafion™ membrane), an anion-exchange membrane, porous polyolefins, polyimides, polyethers, and polyurethanes.

In accordance with the embodiment shown, anode 102 and cathode 104 are formed from two carbon fibers. The carbon fibers can vary in size, but generally have a diameter that ranges from about 2 μm to about 50 μm, and a length that ranges from about 10 μm to about 10 cm. In one embodiment of the invention, the carbon fibers used in anode 102 and cathode 104 have a diameter of about 7 μm and a length of about 2 cm. Anode 102 and cathode 104 can also have electrical connections 103 and 105 that couple biological fuel cell 100 to an electrical device, such as a sensor, an amplifier, a storage device, such as a capacitive storage element or battery, or some other electronic circuit or device. The carbon fibers that form anode 102 and cathode 104 can be coated with thin films of electrocatalyst layers 106 and 108, as shown in FIG. 1. Although clearly shown in FIG. 1, electrocatalyst layers 106 and 108 will generally be much too thin to be distinguishable from the carbon fibers.

Anode electrocatalyst layer 106 is formed on at least a portion of anode 102. Generally, anode electrocatalyst layer 106 will coat the majority of the surface of anode 102. Anode electrocatalyst layer 106 typically comprises an anode redox polymer and an anode enzyme. Examples of enzymes that can be used in anode electrocatalyst layer 106 are oxidases and dehydrogenases of glucose, lactate and pyruvate, as exemplified by glucose oxidase (GOx), lactate oxidase (LOx), and pyruvate oxidase.

Cathode electrocatalyst layer 108 is formed on at least a portion of cathode 104. Generally, cathode electrocatalyst layer 108 will coat the majority of the surface of cathode 104. Cathode electrocatalyst layer 108 typically comprises a cathode redox polymer and a cathode enzyme. Preferred cathode enzymes comprise four copper ions in each of their functional units. An example of a cathode enzyme that can be used in cathode electrocatalyst layer 108 is bilirubin oxidase (BOD).

For purposes of this specification, GOx will often be used herein to reference an enzyme that can be used in anode electrocatalyst layer 106, while BOD will often be used herein to reference an enzyme that can be used in cathode electrocatalyst layer 108. It should be noted that these are merely examples of these enzymes, which examples should not be construed as a limitation as to enzymes that can be used with this invention.

Electrocatalyst layers 106 and 108 electrically couple their respective enzymes to anode 102 and cathode 104 through their respective redox polymer components, which are crosslinked, electron-conducting structures. More than one redox polymer and/or more than one enzyme can be used in each electrocatalyst layer 106 and 108. The electrical coupling provided by the redox polymers is often referred to herein as "wiring" or "wires" or the like. In water, the redox polymers swell, but do not dissolve, to form electron-conducting hydrogels. When the redox polymers and enzymes are sufficiently crosslinked, the hydrogels can be tough, and can have leather-like strength and other mechanical properties. As the electrocatalyst layers 106 and 108 form hydrogels that immobilize the anode enzymes on the anode 102 and the cathode enzymes on the cathode 104, respectively, a membrane for separating the anode reactants and the cathode reactants is not required in biological fuel cell 100. This is a major advantage, in terms of manufacturability and cost reduction, for example, of biofuel cell 100.

In particularly preferred modes of the invention, chemistry that essentially immobilizes or binds the enzymes on anode 102 and the cathode 104 of fuel cell 100 is employed such that an ion- or electrode-separating membrane can be eliminated as a component of the cell. Thus, biological fuel cell 100 may be, and preferably is, a membrane-free or single-compartment cell. As used herein, "membrane-free" or "single-compartment" cell refers to a cell 100 in which the anode 102 and the cathode of the cell, and the immobilized enzymes associated therewith, are not separated by a membrane or partition, although other portions of the cell may be so separated.

The biological fuel cell 100 may comprise anode 102, having disposed thereon an anode enzyme, and cathode 104, having disposed thereon a cathode enzyme, at least a portion of the anode and cathode enzymes being substantially immobilized on anode 102 and cathode 104. For a physiological biofuel cell 100, substantial immobilization refers to a lack of dissolution of the enzyme over a 24-hour period at 37° C. in a pH 7.2 aqueous buffer solution that contains 0.14 M NaCl and 20 mM phosphate ions added to their sodium salts. Those skilled in the art will appreciate that the proportion of the enzyme that must be bound to the electrode (directly or indirectly, but in any case, in adequate proximity to the electrode surface to permit the movement of electrons as the electrochemical reaction proceeds), will be determined by the desired or necessary performance properties of the cell. Overall, the amount of enzyme that may not be fully bound to the electrode will be limited by the need to avoid, in a particular cell design, interference with the performance of the membrane-free or single-compartment cell due to the shuttling of reactive species between the electrodes.

The enzyme in each electrocatalyst layer 106 and 108 typically catalyzes an electrochemical reaction of an anode reductant or a cathode oxidant, respectively. The anode reductant and cathode oxidant are provided by the biological system and comprise the fuel source for biological fuel cell 100. Examples of the most common anode reductants used in biological fuel cell 100 include glucose, lactate, and pyruvate. The cathode oxidant primarily comprises oxygen present in the biological system, found as dissolved molecular oxygen, or as hemoglobin- or myoglobin-bound oxygen. Biological fuel cell 100 can also include other enzymes that break down more complex molecules, for example, carbohydrates, such as starches (for example, glycogen) or celluloses, into simpler components, such as sugars (for example, glucose), alcohols, or carboxylic acids, thereby allowing these more complex molecules to be used as a fuel source as well.

During the operation of biological fuel cell 100, the anode reductant is electrooxidized at anode electrocatalyst layer 106 and the cathode oxidant is electroreduced at cathode electrocatalyst layer 108. The anode redox polymer passes electrons, or a current, between the anode reductant and anode 102, while the cathode redox polymer passes electrons, or a current, between the cathode oxidant and cathode 104. The electrical power of biological fuel cell 100 is generated from the overall oxidation of the anode reductant by the cathode oxidant. In a biological system, for example, the electrical power can be generated by the overall oxidation of glucose, lactate, or pyruvate by dissolved oxygen delivered as hemoglobin-bound oxygen ($HbO_2$), which is in rapid equilibrium with dissolved oxygen passing through the oxygen-permeable membranes of red blood cells. Biological fuel cell 100 facilitates this oxidation reaction, and uses the resulting flow of electrons to produce an electrical current that can power an implanted electrical device.

In biological fuel cell 100, the source of an electron current can be glucose, as it delivers a pair of electrons to anode electrocatalyst layer 106. Such a cell is schematically depicted in FIG. 2. The electrons then travel via anode 102 to an external electrical device or an internal electrical device, such as an implanted device, that is powered by biological fuel cell 100. The electrons power the electrical device and then travel to cathode 104, where they are transmitted via cathode electrocatalyst layer 108 to oxygen (i.e., the cathode oxidant is electroreduced).

In general, for each of electrocatalyst layers 106 and 108, it is preferred that the redox polymer and the enzyme are oppositely charged polyelectrolytes. In one embodiment of the invention, an enzyme used for the electrooxidation of glucose can be GOx wired to anode 102, and an enzyme for the electroreduction of oxygen can be BOD wired to cathode 104. The reaction centers of the two enzymes are electrically wired to anode 102 and cathode 104 via electron-conducting hydrogels, or redox polymers that have swelled in water. As the enzyme GOx is a polyanion at neutral pH, a polycationic redox polymer is most effective as to its wiring. In the operation of the cell, via its wiring, electrons are collected from glucose-reduced GOx at anode 102, where glucose is electrooxidized to δ-gluconolactone (see Eq. 1 below), and electrons are delivered to $O_2$-oxidized bilirubin oxidase at cathode 104, where oxygen is electroreduced to water (see Eq. 2 below). The overall reaction is that of Eq. 3 below.

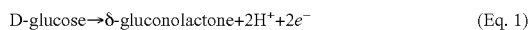
D-glucose→δ-gluconolactone+$2H^+$+$2e^-$ (Eq. 1)

$O_2$+$4H^+$+$4e^-$→$2H_2O$ (Eq. 2)

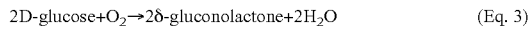
2D-glucose+$O_2$→2δ-gluconolactone+$2H_2O$ (Eq. 3)

The reactions represented by Eqs. 1-3 above are now described in relation to the schematic illustration of FIG. 2. FIG. 2 illustrates the electron transfer involved in the electrocatalytic oxidation of glucose and the electron transfer involved in the electrocatalytic reduction of oxygen, both of which occur in biofuel cell 100. In the biofuel cell 100, the anode 102 and the cathode 104, coated with different cross-linked electrostatic adducts of enzymes and redox polymers, reside in the same solution or same compartment. As shown, electrons are first transmitted from a glucose molecule 300 to an enzyme 302, such as GOx merely by way of illustration. Glucose 300 is therefore electrooxidized to form a gluconolactone molecule 304, and enzyme 302 is reduced. Protons are generally released into the biological system via this reaction (see Eq. 1), while the captured electrons are transmitted to anode 102 through an anode redox polymer 306, such as an osmium(Os)-complex-based redox polymer (Os(II)→Os(III), E°=+0.95 V vs Ag/AgCl). The electrons then travel from anode 102 to an electrical circuit that is typically designed to power an electrical device 400, such as the light bulb shown merely by way of illustration, and in certain preferred embodiments, an implanted electrical device. The electrons eventually make their way to cathode 104, where they are transmitted through a cathode redox polymer 307, such as an Os-complex-based redox polymer (Os(II)→Os(II), E°=+0.55 V vs Ag/AgCl), to an enzyme 308, preferably a copper-containing enzyme, such as a BOD merely by way of illustration. The electrons are then passed on to an oxygen molecule 310 in the biological system, which captures both the transmitted electrons and protons from the biological system to form a water molecule 312.

The physical dimensions of biological fuel cell 100, as well as its operational parameters (e.g., output power and voltage) are, at least in part, a function of the components that form biological fuel cell 100. Merely by way of example, the open-circuit voltage of biological fuel cell 100 can range from about 0.1 volts to about 1.2 volts, and typically, from about 0.2 volts to about 0.9 volts. The voltage at the maximum power point can range from about 0.2 to about 0.8 volts, for example. The volumetric output power density of biological fuel cell 100 can range from about 0.5 $mW/cm^3$ to about 5 $W/cm^3$, for example, although a higher or a lower volumetric output power density is certainly possible. The gravimetric output power density can range from about 5 mW/g to about 5 W/g, for example, although a higher or a lower gravimetric output power density is certainly possible.

The output power density can depend on the flow of fluid through biological fuel cell 100, particularly if the dimensions of the electrodes are large, such as greater than about 0.1 mm. Generally, increasing the rate of this flow of fluid increases the output power density of cells having larger electrodes. By way of example, when the electrodes of the cell 100 are made with carbon cloth discs having a diameter of about 4 mm, the power, or output power density, increases substantially with flow. On the other hand, the power output density is nearly independent of the flow of fluid through the cell 100, or may even decrease slightly with this flow, when the dimensions of the electrodes are small, such as less than about 0.1 mm, less than preferred dimensions of about 0.05 mm, and less than most-preferred dimensions of about 0.02 mm. Thus, when biological fuel cell 100 is formed from two carbon-fiber electrodes, having a diameter of about 7 μm, and a length of about 2 cm, the power, or output power density, is nearly independent of fluid flow through the cell.

The output power density, and therefore the size of an implanted biological fuel cell 100, can be limited by electrode kinetics, ohmic resistance, and/or mass transport. When the electrode kinetics is fast and the biological fuel cell 100 is small enough for the ohmic resistance of the electrolytic solution to be low, the power density is determined by the mass transport of the reactants to the electrodes. When mass transport is rapid, such as via rapidly flowing blood, the power density is determined by the electrode kinetics. The mass-transport-limited current density increases upon raising the concentration of the reactants or upon increasing the flow rate of the biological fluid. Because the concentrations of glucose (about 4 to about 7 mM in the blood of non-diabetic people) and $HbO_2$ (about 5 mM in venous and about 8 mM in arterial blood at normal hematocrit) are defined in blood and in other tissues of the human body, the power density is controlled by the flow rate of the biological fluid when the turnover of the anode or cathode electrocatalyst is fast enough to electrooxidize or electroreduce the entire influx of reactant. If, however, one of the dimensions of the electrodes is small enough, then as discussed above, the power density can be made nearly independent of flow.

In an embodiment of the invention, anode 102 and cathode 104, as well as all other components of biological cell 100, are preferably coated such that they are bio-inert. This is to prevent protein fouling or an immune reaction, for example. By way of example, in one embodiment of the invention, the components of biological fuel cell 100 can be coated with a thin coating that is highly permeable to the reactants. This coating can comprise a photo-crosslinked, bioinert, 18-kD poly(ethylene glycol)diacrylate, formed of a solution containing a photoinitiator, 2,2-dimethoxy-2-phenyl-acetophenone. An appropriate coating can be applied in a variety of ways. For example, aqueous precursor monomer and prepolymer (a low molecular weight polymer) solutions can be dip-coated on fibers or other structures. Alternatively, these solutions can be spun on the rotating components by a process similar to that of spinning photoresists on silicon wafers in the manufacture of integrated circuits. In this latter process, the components being coated are rotated at a defined angular velocity while the solution is applied. The thickness of the film is defined by the angular velocity and the viscosity of the solution. After water evaporates from the deposited films, the films are photo-polymerized via exposure to ultraviolet radiation, for example, from a 150 W mercury lamp disposed 30 cm away from the film.

Miniaturization of biological fuel cell 100 is possible because the cell does not have corroding or corrosive components, and because the cell reactants react much faster at their respective electrodes than at their respective counter electrodes. (See, for example, Mano et al., *A Miniature Biofuel Cell Operating in a Physiological Buffer*, J. Am. Chem. Soc. 2002, 124, 12962-12963.) In other words, miniaturization is made possible by the absence of reaction of glucose at cathode 104 and the very slow reaction of $O_2$ at anode 102, which, as the two electrocatalysts are immobilized on their respective electrodes, eliminates the need for a compartment-separating membrane. As a result, biological fuel cell 100 does not require any of the three components that are generally the most difficult to miniaturize, namely, the case, the seal, and the compartment-separating membrane. Further, as a result of the high selectivity of the electrodes, the surfaces of the electrodes need not be clean, as is required in conventional methanol-air and hydrogen-oxygen fuel cells, and the cleanliness of the cell's fuel and the fuel cell itself is irrelevant.

Thus, in accordance with an embodiment of the invention, biological fuel cell 100 is usually assembled without the case, the seal, and the compartment-separating membrane required by conventional batteries. As a result, biological fuel cell 100 can be manufactured with a footprint smaller than about 3 $mm^2$, preferably smaller than about 1 $mm^2$, and most preferably smaller than about 0.3 $mm^2$. The biological fuel cell, with dimensions on the millimeter to sub-millimeter level, can power devices such as an implanted sensor, a sensor/transmitter, an actuator, or a receiver/actuator system, as further described herein. Further, this small biological fuel cell can be constructed so that none of its components, including its catalytic components, will be dissolved or leached while residing in the body.

The Electrodes

Five exemplary structures, including anode 102 and cathode 104, are illustrated in FIGS. 3A-3E. Merely by way of simplification, these structures are illustrated with similar anode and cathode geometries. It should be noted, however, that these are merely simplified examples of these structures, as the dimensions of the two electrodes may differ because the current densities of the two electrodes are usually not the same, and may be adjusted to ensure that the current densities of the two electrodes are the approximately the same. The optimal ratio of anode area to cathode area depends on the ratio of the respective current densities of the two electrodes in the tissue in which biological fuel cell 100 is used. When the dimensions of the electrodes are larger than about 0.1 mm, their current densities are generally determined by local flow and mass transport. When the dimensions of the electrodes are smaller, their current densities, which may not be limited by mass transport, are generally determined by the kinetics of the electrocatalysts.

In FIG. 3A, the biological fuel cell 600 appears as a bipolar sandwich, similar to conventional fuel cell stacks and button-type batteries. An electronically insulating separator 602 between anode 102 and cathode 104 is penetrated by the blood or by the interstitial fluid, minimizing the ohmic resistance of the cell. Single-cell sandwiches can be stacked to generate a current that is an aggregate or a multiple of the current of the single-cell components. Such a configuration provides a high surface area in a small volume, at the likely expense of increased mass transport resistance. This configuration is preferred when kinetics, rather than mass transport, limits the current.

In the coplanar biological fuel cell 604 of FIG. 3B, a separator for penetration by blood or interstitial fluid (such as the separator 602 in cell 600 of FIG. 3A) is not required. Advantageously, coplanar cell 604 facilitates mass transport to anode 102 and cathode 104 and is of relatively simple construction. In this construction, the electrodes 102 and 104 of the cell 604 can be reduced in width to minimize the ohmic loss. Preferably, these electrodes are long and narrow, in the form of parallel strips.

The biological fuel cells 606, 608 and 610, respectively, of FIGS. 3C, 3D and 3E, have stent-like, cylindrical geometries that are well suited for implantation in blood vessels. The single-walled tubular structures of FIGS. 3C and 3D, namely cells 606 and 608, are comparable to the coplanar structure of FIG. 3B. As shown in FIG. 3C, cell 606 comprises a half-annular anode 102 joined in parallel with a half-annular cathode 104, via an insulating spacer 607, to form a complete annular structure. As shown in FIG. 3D, the cell 608 comprises an annular anode 102, and an annular cathode 104, joined in series, via a ring-like insulating spacer 609, to form a relatively elongated annular structure. In this embodiment, the products of the upstream electrode reaction are swept past the downstream electrode.

Cell 610 of FIG. 3E comprises an annular cathode 104 within an annular anode 102. The cathode and anode may be concentrically arranged as shown. Cell 610 offers less ohmic resistance than the cells of FIGS. 3B to 3D, but has a high mass-transport resistance. Even though $HbO_2$ is in rapid equilibrium with dissolved $O_2$, the lesser diffusivity of $HbO_2$ is likely to lead to a preference for an arrangement of cell 610 in which the cathode 104 is the inner electrode.

Cell 604 of FIG. 3B and cell 608 of FIG. 3D are particularly advantageous in that they are easily optimized in terms of the ratio of the areas of their respective anodes 102 and cathodes 104. In both cell 604 and cell 608, this ratio varies simply with the lengths of the electrode segments. In cell 606 of FIG. 3C, the ratio can be optimized by varying the radius of the radial segments.

According to an embodiment of the invention, anode 102 and cathode 104 are made of a non-corroding metal, such as gold, platinum, palladium, iridium, osmium, rhenium, ruthenium, ruthenium dioxide, and preferably, carbon. By way of example, carbon particles, carbon fibers, carbon cloth, or the like may be used to make carbon-based anodes and cathodes. Carbon particles have effective diameters that range from about 10 nm to about 100 μm, and preferably range from about 2 μm to about 50 μm. Carbon fibers have diameters that normally range from about 2 μm to about 20 μm. Carbon cloth is made of fibers, having diameters similar to those of carbon fibers, and has a void fraction greater than about 10 to about 30 percent by volume, and preferably, greater than about 50 percent by volume.

Each of anode 102 and cathode 104 is coated by crosslinking an electron-conducting redox polymer and an enzyme, each of which is further discussed below, on its surface. Crosslinking a water-soluble redox polymer and an enzyme on a treated carbon electrode produces a hydrogel with an immobilized and wired enzyme. The anode and cathode hydrogels are permeable to water-soluble biochemicals and ions.

Redox Polymers

The redox polymer of the anode electrocatalyst layer 106 electrically connects, or wires, the reaction centers of the anodic enzyme to the anode 102 and the redox polymer of the cathode electrocatalyst layer 108 wires the reaction centers of the cathodic enzyme to the cathode 104. This wiring is accomplished without using a diffusing mediator. The redox polymer preferably forms some type of bond with the enzyme. Preferably, the redox polymer is a polycation that forms an electrostatic adduct with the enzyme. For example, the redox polymer and the enzyme may be, and preferably are, oppositely charged polyelectrolytes. In one particular example, polycationic redox polymers are most effective in the wiring of GOx, because GOx is polyanionic at neutral pH. A current density of about 2 mA/cm² can be reached with carbon-cloth-based electrodes even in air where the redox potential of the wire of GOx is about +0.05 V vs. Ag/AgCl and the electrode is poised at 0.2 V (Ag/AgCl). At this potential, most of the GOx electrons are collected by the wire, with only one-sixth of the current being lost to $O_2$.

A suitable redox polymer is one having a redox species that is a transition metal compound or complex. A preferred transition metal compound or complex is one in which the transition metal is osmium, ruthenium, iron, or cobalt, preferably, the former. According to an embodiment of the invention, the redox polymer has several desirable characteristics, including but not limited to, the following: (1) a flexible, hydrophilic backbone, which provides segmental mobility when the redox polymer is hydrated; (2) redox functions pendant on flexible and hydrophilic spacers, which tend to maximize electron exchange between the colliding redox centers; and (3) small complexes of $Os^{2+/3+}$, having high rates of self-exchange, which small complexes allow the close approach of the reaction centers of the enzymes: For example, an exemplary redox polymer, PVP-[Os(N,N'-dialkylated-2,2'-bi-imidazole)$_3$Cl]$^{2+/3+}$, has long and flexible tethers that bind the redox centers to the polymer backbone and allow for efficient collection of electrons from elements such as GOx. This redox polymer is illustrated in FIG. 4 and further described in Mao et al., *Long Tethers Binding Redox Centers to Polymer Backbones Enhance Electron Transport in Enzyme "Wiring" Hydrogels*, J. Am. Chem. Soc. 2003, 125, 4951-4957.

The redox polymer is important to the effective functioning of cell 100. For example, when a cell lacks the redox-polymer-based electrical connections, or wires, discussed above, the internal resistance of the cell is so high that no current will flow. Further by way of example, when BOD enzyme is used in a cell that lacks a redox polymer, only a very small fraction of the molecules of the BOD enzyme are properly oriented to allow electron transfer with cathode 104 and to thereby contribute to the current in the cell. By contrast, when a redox polymer hydrogel is present in cell 100, the enzyme molecules need not be oriented toward the surface of the electrode because virtually all of the reaction centers of the enzyme are wired to the electrode via the redox centers of the redox polymer hydrogel. The hydrogel has mobile segments that can effectively approach these reaction centers of the enzyme to effect this wiring. Additionally, the three-dimensional volume of the hydrogel can contain not just one layer, but multiple layers, of the enzyme that is wired to the electrode.

In summary, in cells lacking the wiring provided by redox polymers, electron transfer between an enzyme and an electrode may be poor or may not take place at all. For example, in such a cell, as effective electron transfer between an electrode and an enzyme requires that the active site of the enzyme face toward the surface of the electrode, only a small fraction of a monolayer of the randomly oriented enzyme will be electroreduced or electrooxidized. Therefore, the current densities associated with cells that lack redox-polymer wiring cannot approach the current densities associated with the redox-polymer-wired cells 100 described herein. Advantageously, extraordinarily high current densities, such as from about 0.1 to about 10 mA/cm², can be obtained from cells 100 containing electrodes that have been modified with redox polymer hydrogels that wire enzymes such as GOx and BOD.

The redox potentials of the redox polymers that wire the anode enzyme and the cathode enzyme can be tailored to increase the power output of biological fuel cell 100. The difference in these redox potentials affects the optimal operating potential of biological fuel cell 100. The redox potential of the anode redox polymer is reducing relative to the redox potential of the cathode redox polymer. The preferred redox potential of the anode redox polymer depends on the anode enzyme, and that of the cathode polymer on the cathode enzyme. Usually the redox potential of the anode polymer is tailored to function under physiological conditions, and if the anode enzyme is GOx, the redox polymer is also tailored to function in the range from about −300 mV to about +200 mV, and preferably from about −150 mV to about +70 mV, versus the potential of the Ag/AgCl (3 M KCl) electrode. The redox potential of the cathode redox polymer is tailored to be in the range of from about +250 mV to about +600 mV, and preferably from about +300 mV to about +500 mV, versus the potential of the Ag/AgCl (3 M KCl) electrode.

Composite Electrodes

Anode electrocatalyst layer 106 and cathode electrocatalyst layer 108 are composed of redox polymers that form hydrogels upon swelling in water, as previously described. In these layers, electron transport occurs by way of collisions between redox centers that are tethered to crosslinked polymers. When the redox polymers are crosslinked and swelled in water, chain segments of the polymers are mobile, electron diffusivity via the polymers is high (>$10^{-8}$ cm²/s), but the hydrogels are soft. When the redox polymers are highly crosslinked, the polymers are mechanically tough even after forming hydrogels, but the segmental mobility and the electron diffusivity associated with the polymer are reduced. Composite electrodes (e.g., a composite anode and a composite cathode) are composed of redox polymers that are highly crosslinked, yet still form hydrogels having mobile chain segments.

In an embodiment of the invention, a composite anode is formed by combining electrocatalyst layer 106 with a carbon anode 102, and a composite cathode is formed by combining electrocatalyst layer 108 with a carbon cathode 104. The carbon anode 102 and/or carbon cathode 104 is preferably composed of carbon in the form of carbon particles, carbon fibers, or most preferably, carbon cloth. The electrocatalyst layer and the electrode can be combined by binding the hydrogel to hydrophilic carbon particles, carbon fibers, or carbon cloth, to produce a relatively strong composite electrode. The specific area (area per unit weight) of the carbon cloth is high, and carbon fibers, coated with a thin film of well-crosslinked hydrogel, have a high water-wetted surface area. The composite electrode is a well-crosslinked, leather-like, hydrophilic composite electrode that can maintain mechanical integrity and high current density under the shear stress exerted by rapidly flowing solutions at flow velocities similar to those of blood in major arteries.

In one embodiment of the invention, 10-μm-diameter carbon fibers, on which the electrostatic redox-polymer-enzyme adduct is crosslinked, can be used. FIG. 8 shows a scanning electron microscope image (at 500 times magnification) of a composite electrode, in which the crosslinking of the redox-polymer-enzyme adduct on carbon fibers, of about 10 μm in diameter, can be seen. The carbon fibers may be treated to render their surfaces hydrophilic. The surfaces can be plasma-oxidized for this purpose, although other known methods can be used. The composite electrodes of this embodiment can withstand a shear stress of 0.08 N/m$^2$ that is predicted for blood flowing at a linear velocity of 10 cm/s.

In another embodiment of the invention, disc-shaped carbon cloth electrodes can be used to form composite electrodes. The currents associated with these composite electrodes are limited by mass transport. When these composite electrodes are rotated, the currents increase with the square root of their angular velocity, in accordance with the Levich Equation, until the kinetic limit defined by the electrocatalyst is reached. For carbon cloth discs with a diameter of 4 mm, this limit is about 2 to about 5 mA/cm$^2$ of geometrical surface area (as opposed to true surface area) for the anode, and about 5 to about 9 mA/cm$^2$ of geometrical surface area for the cathode. This carbon-cloth embodiment differs from a previously mentioned, carbon-fiber embodiment in which single carbon fibers of about 7 μm in diameter are used to build the electrodes. For these carbon-fiber electrodes, the associated currents are, for the most part, kinetically limited, having a limit of about 1 mA/cm$^2$ of true area, which is about equal to the geometric area.

Anodes

Anode 102 of biological fuel cell 100 effectuates the electrooxidation of the fuel of the cell, such as the electrooxidation of glucose to gluconolactone schematically illustrated in FIG. 2. As described previously, anode enzymes, examples of which are oxidases and dehydrogenases, catalyze this electrooxidation of the cell's fuel. These anode enzymes are wired to the anodes via an anode redox polymer. An example of a redox polymer of an anode electrocatalyst layer 106 is the polymer X5, sometimes referred to herein as polymer I, the representative structure of which is shown in FIG. 4. Polymer X5 is derived from the copolymer of poly(acrylamide) and poly(4-vinyl pyridine) and comprises an Os complex. Another example of a redox polymer of an anode electrocatalyst layer 106 is shown in FIG. 5. This redox polymer is derived from poly(N-vinyl imidazole) and comprises an Os complex. In these examples, the Os(II) and Os(III) centers of the anode redox polymers and the anode enzymes are immobilized in electron-conducting films on the surfaces of the anodes.

Cathodes

Cathode 104 of biological fuel cell 100 effectuates the four-electron electroreduction of $O_2$ to water under physiological conditions. This electroreduction reaction is catalyzed by the cathode enzymes, which are wired to the cathodes via a cathode redox polymer. A representative structure of an exemplary redox polymer, PAA-PVI-[Os(4,4'-dichloro-2,2'-bi-pyridine)$_2$Cl]$^{+/2+}$, of a cathode electrocatalyst layer 108 is shown in FIG. 6, and a representative structure of another exemplary redox polymer, sometimes referred to herein as polymer II, is shown in FIG. 7.

As described previously, cathode enzymes catalyze the four-electron reduction of $O_2$ to water. The cathode enzymes are copper-containing oxidases, examples of which include laccases, ascorbate oxidases, ceruloplasmines, and bilirubin oxidases (BODs). The preferred enzymes are exemplified by BODs, which unlike laccases, retain more than 80%, and usually retain more than 90%, of their maximal activity under physiological pH and salinity.

The catalytic reduction of $O_2$ to water depends on the coordination of the copper ions of the enzymes, or more particularly, the four $Cu^{+/2+}$ ions of the enzymes. The $Cu^{+/2+}$ ions are classified by the ligands that coordinate them into three "types", types I, II, and III. The centers of type I $Cu^{+/2+}$ ions show an intense Cys to Cu(II) charge transfer band at around 600 nm. The type I copper center accepts electrons from an organic substrate, such as a phenol, ascorbate, or bilirubin, and relays the electrons to the $O_2$-reduction site. The $O_2$-reduction site is a tri-nuclear cluster, consisting of one type II $Cu^{+/2+}$ center and a pair of type III $Cu^{+/2+}$ centers with a characteristic 330-nm shoulder.

In non-physiological conditions, laccase monolayers on vitreous carbon catalyze the four-electron electroreduction of $O_2$ to water. (See, for example, Barton et al., *The "Wired" Laccase Cathode: High Current Density Electroreduction of $O_2$ to Water at +0.7 V (NHE) at pH* 5, J. Am. Chem. Soc. 2001, 123, 5802-5803; Chen et al., *A Miniature Biofuel Cell*, J. Am. Chem. Soc. 2001, 123, 8630-8631; Barton et al., *Electroreduction of $O_2$ to Water on the "Wired" Laccase Cathode*, J. Phys. Chem. B 2001, 105, 11917-11921; and Barton et al., *Electroreduction of O2 to water at 0.6 V (SHE) at pH 7 on the 'wired' Plueuotus ostreatus laccase cathode*, Biosensors and Bioelectronics 17 (2002), 1071-1074.) For example, it has been shown that a composite electrode formed using laccase from *Coriolus hirsutus* crosslinked with a redox polymer on a hydrophilic cloth of 10 μm-diameter carbon fibers can electroreduce oxygen to water in the absence of chloride, in a pH 5 citrate buffer, at a current density of 5 mA/cm$^2$ at −0.13 V versus the reversible potential of the $O_2/H_2O$ electrode at 37.5° C. In this example, the redox polymer was PVI-Os(tpy)(dme-bpy)$^{2+/3+}$ [poly-N-vinylimidazole, with one-fifth of the imidazoles complexed with [Os(tpy)(dme-bpy)]$^{2+/3+}$, where tpy=terpyridine, and dme-bpy=4,4'-dimethyl-2,2'-bipyridine]. This redox polymer electrically connected, or wired, the *C. hirsutus* laccase reaction centers to the carbon fibers.

Under physiological conditions, however, the current density of the wired *C. hirsutus* laccase-carbon cloth composite cathode was very small. At a pH of about 7.4, the *C. hirsutus* laccase was practically inactive, and the *C. hirsutus* laccase was inhibited by Cl⁻ at a chloride concentration of about 0.14 M. Therefore, under physiological conditions, the lacasse-based electrode is not a viable option for the electroreduction of $O_2$ to water.

According to an embodiment of the invention, the BOD enzyme can be used in biological fuel cell 100 to electroreduce $O_2$ to water under physiological conditions. There are different forms of BOD available, such as BOD from *Myrothecium verrucaria* (Mv-BOD) and DOD from *Trachyderma tsunodae* (Tt-BOD). BODs are usually monomeric proteins and have molecular weights ranging from about 52 kDa to about 65 kDa. By way of example, Tt-BOD is a monomeric protein that has a molecular weight of about 64 kDa, and Mv-BOD has a molecular weight of about 52 kDa. Both Mv-BOD and Tt-BOD are multi-copper oxidases, each containing one type I, one type II, and two type III copper ions. These three types are defined by their optical and magnetic properties. Type I (blue) copper ions have a characteristic Cys to Cu(III) charge-transfer band near 600 nm. The type I copper center accepts electrons from the electron-donating substrate of the enzyme and relays these to the $O_2$-reduction site. The $O_2$-reduction site is a tri-nuclear cluster, consisting of a type II copper ion and a type III pair of cupric ions with a characteristic 330-nm shoulder.

In an electroreduction reaction, BOD catalyzes the oxidation of bilirubin to biliverdin, as represented by Eq. 4 below.

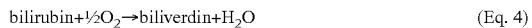

$$\text{bilirubin} + \tfrac{1}{2}O_2 \rightarrow \text{biliverdin} + H_2O \tag{Eq. 4}$$

In one embodiment of the invention, Mv-BOD can be used in cathode electrocatalyst layer 108. In a cathode 104 constructed using Mv-BOD, the electrostatic adduct of the polyanionic Mv-BOD and its wire, the polycationic redox copolymer of polyacrylamide and poly(N-vinylimidazole) complexed with $[Os(4,4'\text{-dichloro-}2,2'\text{-bipyridine})_2Cl]^{+/2+}$, are immobilized on cathode 104. The current density of a cathode 104 built according to this embodiment, when rotated, is $O_2$-transport-limited up to about 8.8 mA/cm$^2$ and has a kinetic limit of about 9.1 mA/cm$^2$. When this Mv-BOD cathode 104 is rotated at around 300 rpm and is poised at around −256 mV versus the potential of the reversible $O_2/H_2O$ electrode, cathode 104 will have an initial current density of about 2.4 mA/cm$^2$ that may decline to around 1.3 mA/cm$^2$ after approximately six days of continuous operation at 37.5° C.

In another embodiment of the invention, Tt-BOD can be used in cathode electrocatalyst layer 108. In Tt-BOD, all of the ligands of the type II and type III $Cu^{+/2+}$ centers are histidines (His), similar to ligands of ascorbate oxidase. It is believed that the full His coordination of the type II $Cu^{+/2+}$ center is the underlying cause of the relative insensitivity of BODs to inhibition by the chloride and hydroxide anions at their physiological concentration. Accordingly, other enzymes having the three types of copper centers, would also be useful as components of cathode electrocatalysts in cathodes operating under physiological conditions.

While the type I $Cu^{+/2+}$ center of Mv-BOD has an axial, weakly coordinating methionine, that of Tt-BOD has a non-coordinating phenylalanine. In a comparison of two laccases, one with methionine and the other with phenylalanine in the axial position of the type I $Cu^{+/2+}$ center, it was found that the redox potential of the type I $Cu^{+/2+}$ center was approximately 100 mV more oxidizing when the ligand was phenylalanine. It has been shown that the use of Tt-BOD shifts the operating potential of cathode 104 upward and improves its operational stability over that of Mv-BOD. It is believed that any observed differences between the wired Mv-BOD and the wired Tt-BOD cathodes, such as differences in the redox potentials, current densities, pH ranges and the operational stabilities, are derived from the more oxidizing redox potential of the type I $Cu^{+/2+}$ center of Tt-BOD, and from differences in the electrostatic adducts that the two polyanionic enzymes form with their respective wiring redox polymers.

Tailoring of the Biological Fuel Cell

In a preferred embodiment, electrons cascade energetically downhill in small potential steps via the anode 102 and the cathode 104 of the biological fuel cell 100. Using this embodiment, one can tailor the cell to obtain a desired cell voltage, a usable or an optimal cell current, and efficient operation. The electron cascade associated with anode 102 involves small potential steps between the anode enzyme, such as GOx, and the anode redox polymer, and between the anode redox polymer and the anode, as the electrons are transferred from the fuel of the cell, such as glucose, to the anode. The electron cascade associated with the electron transfer between the anode 102 and the cathode 104 involves a further potential step, the thermodynamic limit of which is the cell voltage. The electron cascade associated with cathode 104 involves small potential steps between the cathode and the cathode redox polymer, and between the cathode redox polymer and the cathode enzyme, such as BOD, as the electrons are transferred from the cathode to molecular oxygen.

In the above-described embodiment, the size of the small potential steps, which should be measurable voltages, can be selected to obtain desirable voltage, current, and efficiency characteristics of the cell. For example, the potential steps, each, some, or all of which may vary in size, can be selected to be from about 10 mV to about 200 mV, such as from about 20 mV to about 100 mV, as is preferred when the cell operates to electrooxidize glucose at anode 102 and electroreduce oxygen at the cathode 104, as previously described. Preferably, the operating voltage of the cell, or the difference between the electrode potential at the cathode and the anode at certain current densities, is greater than or equal to 0.6 V. The current densities are selected according to the application, where the selection may be based on factors such as the enzyme turnover rate, electron-transport resistance and mass-transport resistance. The power density per unit area of the cell is the product of the operating voltage and the current density of the cell.

Exemplary Applications

Operation of a Miniature Biological Fuel Cell in a Biological System

As previously described, the biological fuel cell of the present invention can be tailored such that its operating voltage is greater than or equal to 0.6 V, a relatively high voltage for a miniature biological fuel cell. Such an operating voltage is of particular interest, as it is sufficient to drive electronic circuits, such as silicon-based integrated circuits or organic circuits, composed of printed, electrodeposited, or otherwise formed circuit patterns. For example, for silicon-based circuits, preferably, a cell voltage of greater than about half the value of the silicon electron-conducting gap (at about 1.106 V), should be used, as this may simplify the design of the circuits. These circuits can be mounted on or packaged in a biocompatible material, such as a biocompatible plastic, polymer, or ceramic material, for applications calling for implanted biofuel cells, for example.

A miniature, membrane-free, biofuel cell operating at 0.78 V has been reported in Mano et al., *A Miniature Biofuel Cell Operating at 0.78 V*, Chem. Commun., 2003, 518-519. Operation at this relatively high voltage was attributed to the use of PVI-$[Os(N,N'\text{-bialkylated-}2,2'\text{-biimidazole})_3Cl]^{2+/3+}$, the representational structure of which is shown in FIG. 4, as opposed to another anode redox polymer. The cell produced 1.2 µW with a power density of 2.68 µW/mm$^2$. As the cathode enzyme of the biofuel cell was a laccase, the cell was operated at 37° C., in a pH 5 buffer, and in the absence of chloride.

In an embodiment of the invention, the cathode enzyme of the biofuel cell is a BOD, rather than a laccase, such that the cell can operate at relatively high voltage, but under physiological conditions. In Experimental Example 3, set forth and further described below, such a biofuel cell, consisting of two, electrocatalyst-coated, carbon fibers (7-µm in diameter, 2 cm in length), was tested for operation in a biological system. When the miniature biofuel cell was implanted in a grasshopper, no power was produced. This was attributed to the fact that the sugar in the biological fluid of the grasshopper is disaccharide trehalose, rather than glucose. When the cell was implanted in a grape, a fruit having a high glucose concentration (>30 mM) in its sap, power was produced.

The power output of the grape-implanted cell was $O_2$-transport-controlled and depended on the position of the cathode fiber. When the cathode fiber was near the center of the grape, where the fruit was oxygen-deficient, the power density was only 0.47 μW/mm$^2$ at 0.52 V. When the cathode fiber was shallowly implanted near the skin of the grape, where the sap was better oxygenated, the power density was 2.4 μW/mm$^2$ at 0.52 V. The grape-implanted cell retained 85% of its initial power output of 1.1 μW after a day of operation.

When the above-described miniature biofuel cell was tested in an aerated, glucose-containing physiological buffer (pH 7.2, 0.14 M NaCl, 20 mM phosphate) at 37° C., it operated continuously for a week. The output of the cell in the physiological buffer solution was 1.9 μW, which is sufficient for powering low-power CMOS circuits, and the operating voltage of 0.52 V is adequate for operation of low-voltage CMOS/SIMOX integrated circuits. The cell is thus suitable for powering implanted, autonomous sensor-transmitter systems, such as those of relevance to physiological research and medicine. Examples of such systems and their applications are provided in U.S. patent application Ser. No. 09/753,746, of Heller, Funderburk, Drucker and Jin, entitled "Analyte Monitoring Device and Methods of Use" which was filed on Jan. 2, 2001. Various such devices and applications are further described below.

Applications for an Implantable Miniature Biofuel Cell

An implantable biofuel cell suitable for medical applications is preferably inexpensive (~sub-dollar), small (~sub-mm$^2$ footprint; ~sub-mm$^3$ volume), disposable or short-lived (~1-week), low-power (~μW for continuous operation, ~milliW for intermittent operation), and low-voltage (~0.52-0.78 V, and preferably, >0.6 V, operating voltage). Here, the term "low-power" or "low-voltage" refers to a power or voltage low enough to be suitable or safe for implantation in a biological system, such as a human body, although such power or voltage may be a relatively high power or voltage, as described above, in the context of an achievable operating power or voltage for a miniaturized biofuel cell. For these applications, the implantable biofuel cell is preferably miniaturized, for example, small relative to the size of the electronic package of the device it powers, and designed to have an operational life, operating voltage, current density, power density per unit area, and the like, suitable for the application.

The implantable biofuel cell is useful in a variety of medical applications. For example, it may be used in various medical devices that operate intermittently, continuously, or autonomously. In a particular example, the biofuel cell may be used to power miniature, in vivo, trans- or sub-cutaneous, lactate and/or pyruvate sensor-transmitter devices for signaling the extent of ischemia resulting from internal or external bleeding or other stress. Further, the biofuel cell may be used to power various miniature, intermittent, continuous or autonomous, in vivo, medical devices, such as preferably continuous, trans- or sub-cutaneous glucose monitors that can autonomously activate the administration of insulin to diabetic patients; preferably continuous monitors of the condition of surgical sites, such as post-surgical sites, that can autonomously activate the administration of agents to reduce bleeding, to reduce pain, and/or to promote healing; preferably continuous monitors of harmful or poisonous agents, or biological- or chemical-warfare agents, such as monitors that can autonomously activate the administration of an antidote; and similar intermittent, continuous or autonomous monitoring and/or treatment devices.

An example of an autonomous, trans- or sub-cutaneous, analyte-monitoring device is now described in relation to FIG. 9. The device 700 preferably has two, physically separate sections, namely, a sensor section 800 and a receiver-transmitter section 900, as depicted in the schematic diagram of FIG. 9. This physical separation simplifies manufacture of the device. The two sections of the device may be in the form of patches that can be worn on the skin of a patient or user of the device, via adhesive or other attachment mechanism, for example.

The sensor section 800 comprises a physiological, analyte sensor 802 that is configured for trans- or sub-cutaneous implantation via the skin of the patient. Such a sensor may be used for the direct testing of analyte levels in the biological fluid associated with the tissue at or adjacent to the implantation site. This level may be correlated and/or converted to analyte levels in blood or other fluids. The site and depth of insertion may affect the particular shape, components, and configuration of the sensor 802. Examples of suitable sensors for use in the analyte-monitoring systems of the invention are described in U.S. patent application Ser. No. 09/034,372.

The sensor section 800 further comprises a miniature biofuel cell 100, as described herein, that is electrically coupled to the sensor 802 and electrically coupled to a transmitter 804, such as an antenna, for transmitting a signal from the sensor to the receiver-transmitter section 900. Preferably, the miniature biofuel cell 100 is integrated with various electrical components, including the transmitter 804, on an integrated circuit chip 820, such as an organic or a silicon-based integrated circuit, constructed for biological compatibility, such as being mounted on or housed in a biologically compatible material, as previously described. The transmitter, or antenna, is typically the largest, or longest, component of the sensor section 800 to ensure adequate signal transmission. That is, its length may be on the order of about one-fourth or more of the wavelength of the signal it transmits, such as on the order of that used in cellular telephones. Preferably, the transmitter comprises a carbon fiber that is of the same length as a carbon fiber electrode of the biofuel cell 100, so that the size of the sensor section 802 can be reduced or minimized. The transmitter 804 may take the form of an antenna protruding from the sensor section 800, in a manner similar to that of an antenna that protrudes from a cellular telephone, or it may take form of a typical integrated circuit component, such as a component printed, electrodeposited, or otherwise patterned on an integrated circuit substrate, as previously described.

Other electrical components may include a potentiostat, a capacitor, a resistor, an amplifier, a converter, such as current-to-voltage or a current-to-frequency converter, control or logic sub-circuitry (such as subcircuitry for the control of the sensor 802 or the cell 100, the control of signal receipt or transmission, or the evaluation of signals from the sensor), and/or the like. The biofuel cell 100 may be used to provide a voltage across the electrodes of the sensor 802, such as via a potentiostat, to charge a capacitor for the storage of signals from the sensor 802, to provide power for relaying a signal from the sensor 802 to the transmitter 804 and transmitting a signal from the transmitter 804 to the receiver-transmitter section 900, and/or the like.

The biofuel cell 100 is designed to accommodate the various power and energy requirements of the sensor section 800, particularly those of the transmitter 804, which typically consumes the most energy. According to an embodiment of the invention, the biofuel cell can provide about 2 μW or more of power for an autonomous, three-day, physiological, glucose biosensor-transmitter system having a sub-mm$^2$ footprint and a sub-mm$^3$ volume. As the power requirement of the transmitter 804 increases with a square of the distance, d, between it and the receiver-transmitter section 900, preferably this distance is kept to a minimum, so that the biofuel cell 100 and the sensor section 800 are as small as possible or desired. For example, when the duty cycle is about 1:100, this distance may be on the order of up to and including about 20 cm (although longer distances may be possible), and more preferably, up to and including about 5 cm. Preferably, the transmitter 804 of the sensor section 800 is located as close as possible to the receiver-transmitter section 900, and more particularly, a receiver 902 of the receiver-transmitter section.

In operation of the analyte-monitoring device 700, the transmitter 804 of the sensor section 800 transmits a signal, representative of the concentration or level of analyte in the subcutaneous tissue, to the receiver-transmitter section 900. The receiver-transmitter section 900 has a receiver 902, communicatively coupled to the transmitter 804, for receiving the signal from the transmitter 804 of the sensor section 800 of the device. The receiver 902 is formed using known receiver and antenna circuitry. The receiver-transmitter section 900 also has a transmitter 904, electrically coupled to the receiver 902, for receiving the signal from the receiver 902 and transmitting or displaying or otherwise processing information from the signal, such as transmitting or displaying the information (such as analyte-concentration information) to the patient, transmitting the information to a remote device 1000, such as a communication device (such as an alarm or a remote display) or a drug delivery device (such as a device adapted to deliver a drug or a medicine to the patient, based on the information, as further described below), or processing the information to evaluate a condition of the patient, for example. While the transmitter 904 is schematically shown in FIG. 9 as an antenna for the transmission of information, merely by way of example, it may take the form of a display, such as a digital read-out display. The receiver-transmitter section 900 may comprise other various electrical components and sub-circuitry to facilitate its functioning, such as the various electrical components described in the above-referenced U.S. patent application Ser. No. 09/753,746.

As mentioned above, the receiver-transmitter section 900 of the device 700 may be used to transmit information to a remote drug delivery device, as represented by remote device 1000 in FIG. 9, via any sufficient communicative coupling between the transmitter 904 and the remote device 1000. Alternatively, as schematically depicted in FIG. 10, the receiver-transmitter section 900 of the device 700 could be replaced by a receiver-delivery section 1100 comprising a receiver 1200, communicatively coupled to the transmitter 804, and a drug reservoir 1300, operatively or electrically coupled to the receiver 1200, in which the receiver 1200, upon receiving a certain signal from the sensor section 800, triggers the delivery of a drug or a medicine from the drug reservoir to the patient. By way of example, the delivery may be accomplished by way of a drug delivery pump 1250 and delivery conduit 1320, such as biocompatible surgical tubing, each of which is operatively coupled to the drug reservoir 1300, as shown, where the delivery conduit 1320, which may be controlled by a check valve 1310, is connected to a trans- or sub-cutaneous insertion device 1330. In this embodiment, an interim receiver-transmitter section, such as receiver-transmitter section 900 previously described, may be omitted from the device 700, and the device may serve as an analyte-monitoring and treatment device.

For the drug delivery embodiments described above, a suitable drug delivery pump system is a disposable system, as described in a U.S. Provisional Application Ser. No. 60/417,464, of Benjamin M. Rush, entitled "Disposable Pump for Drug Delivery System," which was filed on Oct. 9, 2002, or more preferably, a disposable system with an actuation circuit for drug delivery, as described in a U.S. Provisional Application Ser. No. 60/424,613, of Christopher V. Reggiardo, entitled "Disposable Pump and Actuation Circuit for Drug Delivery," which was filed on Nov. 6, 2002. As the drug delivery pump generally requires a great deal of power, an energy source other than a biofuel cell described herein is needed.

The autonomous, subcutaneous, analyte-monitoring and/or treatment devices just described can be used for the monitoring and/or treatment of diabetics, where the analyte is glucose and the drug is insulin; for the monitoring and/or treatment of poison victims, such as snake-bite victims, where the drug is a poison antidote, such as a venom antidote; for the monitoring and/or treatment of ischemia, where the analyte is lactate or pyruvate, indicative of bleeding or other stress, and the drug is an appropriate medicament; and for like applications. Alternatively, the autonomous, analyte-measuring device and/or may be cutaneous, or located on the skin, where the sensor is in contact with the skin, and used for applications such as the monitoring and/or treatment of a skin contaminant, such as a nerve gas or other biological- or chemical-warfare agent, where the drug is atropine or some other appropriate antidote or medicine. For a number of such applications, the device could be a wearable monitoring or monitoring and treatment device by virtue of its small size.

An embodiment of an autonomous, analyte-monitoring and treatment device, which includes a drug delivery system, is now described in relation to a schematic, block-diagram illustration of FIG. 11. In this illustration, a sensor-based drug delivery system 1400 is shown as having a sensor control section 1412, a portion of which is trans- or sub-cutaneously inserted into the patient, namely, an insertion portion of the sensors 1410 that is schematically shown in dashed lines. The system may provide a drug to counteract the high or low level of the analyte in response to the signals from one or more sensors 1410. Alternatively, the system monitors the drug concentration to ensure that the drug remains within a desired therapeutic range. The drug delivery system includes one or more (and preferably two or more) subcutaneously implanted sensors 1410, an on-the-skin sensor section 1412, a receiver/display unit 1414, a data storage and controller module 1416, and a drug administration system 1418. In some cases, the receiver/display unit 1414, data storage and controller module 1416, and drug administration system 1418 may be integrated in a single unit. The sensor-based drug delivery system 1400 uses data form the one or more sensors 1410 to provide necessary input for a control algorithm/mechanism in the data storage and controller module 1416 to adjust the administration of drugs. As an example, a glucose sensor could be used to control and adjust the administration of insulin.

In this embodiment, sensor 1410 produces signals correlated to the level of the drug or analyte in the patient. The level of the analyte will depend on the amount of drug delivered by the drug administration system. A processor 1420 in the on-the-skin sensor section 1412, as illustrated in FIG. 11, or in the receiver/display unit 1414 determines the level of the analyte, and possibly other information, such as the rate or acceleration of the rate in the increase or decrease in analyte level. This information is then transmitted to the data storage and controller module 1410 using a transmitter 1422 in the on-the-skin sensor section 1412, as illustrated in FIG. 11, or a non-integrated receiver/display unit 1414.

If the drug delivery system 1400 has two or more sensors 1410, the data storage and controller module 1416 may verify that the data from the two or more sensors 1410 agrees within predetermined parameters before accepting the data as valid. This data may then be processed via the data storage and controller module 1416, optionally with previously obtained data, to determine a drug administration protocol. The drug administration protocol is then executed using the drug administration system 1418, which may be an internal or external infusion pump, syringe injector, transdermal delivery system (e.g., a patch containing the drug placed on the skin), or inhalation system. Alternatively, the drug storage and controller module 1416 may provide a drug administration protocol so that the patient or another person may provide the drug to the patient according to the profile.

In one embodiment of the invention, the data storage and controller module 1416 is trainable. For example, the data storage and controller module 1416 may store glucose readings over a predetermined period of time, e.g., several weeks. When an episode of hypoglycemia or hyperglycemia is encountered, the relevant history leading to such event may be analyzed to determine any patterns that might improve the system's ability to predict future episodes. Subsequent data might be compared to the known patterns to predict hypoglycemia or hyperglycemia and deliver the drug accordingly. In another embodiment, the analysis of trends is performed by an external system or by a processing circuit (not shown) in the on-the-skin sensor section 1412 or an analyzer (not shown) in the receiver/display unit 1414 and the trends are incorporated in the data storage and controller 1416. Examples of suitable processing circuits and suitable analyzers are described in the above-referenced U.S. patent application Ser. No. 09/753,746.

According to one embodiment, the data storage and controller module 1416, a processing circuit, and/or an analyzer utilize patient-specific data from multiple episodes to predict a patient's response to future episodes. The multiple episodes used in the prediction are typically responses to a same or similar external or internal stimulus. Examples of stimuli include periods of hypoglycemia or hyperglycemia (or corresponding conditions for analytes other than glucose), treatment of a condition, drug delivery (e.g., insulin for glucose), food intake, exercise, fasting, change in body temperature, elevated or lowered body temperature (e.g., fever), and diseases, viruses, infections, and the like. By analyzing multiple episodes, the data storage and controller module 1416, processing circuit, and/or analyzer can predict the coarse of a future episode and provide, for example, a drug administration protocol or administer a drug based on this analysis. An input device (not shown) may be used by the patient or another person to indicate when a particular episode is occurring so that, for example, the data storage and controller module 1416, processing circuit, and/or analyzer can tag the data as resulting from a particular episode, for use in further analyses.

In addition, the drug delivery system 1400 may be capable of providing on-going drug sensitivity feedback. For example, the data from the sensor 1410 obtained during the administration of the drug by the drug administration system 1418 may provide data about the individual patient's response to the drug which can then be used to modify the current drug administration protocol accordingly, both immediately and in the future. An example of desirable data that can be extracted for each patient includes the patient's characteristic time constant for response to drug administration (e.g., how rapidly the glucose concentration falls when a known bolus of insulin is administered). Another example is the patient's response to administration of various amounts of a drug (e.g., a patient's drug sensitivity curve). The same information may be stored by the drug storage and controller module and then used to determine trends in the patient's drug response, which may be used in developing subsequent drug administration protocols, thereby personalizing the drug administration process for the needs of the patient.

Use of the Oxygen Electroreducing Cathode to Assay HbA1c

In an embodiment of the invention, one or more components of biological fuel cell 100 can be used to build a cell that can be operated to assay HbA1c. The HbA1c molecule is a hemoglobin molecule that has been combined with a glucose molecule. Unlike a glucose measurement, which reflects the current blood sugar level of a person, such as a medical patient, an HbA1c measurement can reflect how well a person has been controlling his or her glucose levels over a period of several months. In accordance with an embodiment of the invention, a "desktop" HbA1c assay can be developed.

The basis for the HbA1c assay of the invention comes from the ability to wire reaction centers of an enzyme, e.g., BOD, to cathode 104. As explained herein, BOD catalyzes the four-electron reduction of oxygen to water. Cathode 104, when constructed with BOD as the redox enzyme, can operate under physiological conditions and can therefore be used with a biological fluid of a person or other animal to provide an HbA1c measurement.

Hemoglobin, being the oxygen carrier of blood, reversibly binds oxygen, forming $HbO_2$. The equilibrium of the reaction, $Hb+O_2 \leftrightarrow HbO_2$, is rapid. Because $O_2$ is rapidly released by $HbO_2$ when $O_2$ is depleted from the solution in an electrochemical cell, the concentration of $HbO_2$ can be measured coulometrically based on the reaction, $4H^+ + 4e^- + HbO_2 \rightarrow 2H_2O + Hb$. The concentration of available oxygen in arterial blood is about 8 mM. In a coulometric assay, the red blood cells (optionally captured on Nylon or similar cloth) would be lysed in pH 5 citrate buffer under air, and the $HbO_2$ would be coulometrically assayed. Because the concentration of $O_2$ in water in equilibrium with air at 25° C. is known to be 0.24 mM, the amount of non-Hb-bound $O_2$ would be subtracted in calculating the amount of $HbO_2$. The HbA1c/Hb ratio would be measured by one of the methods (1)-(3) set forth below.

(1) Magnetic beads that are <1 μm (available from Bangs Laboratories), on which antibodies against HbA1c would be immobilized, can be mixed with a citrate-solution diluted blood sample. Two measurements would be performed, one on the entire sample, and a second on the re-oxygenated HbA1c bound to the magnetic beads, after their removal to a chamber of an electrochemical cell. Alternatively, the second measurement could be performed on the residual Hb, after the magnetic separation of the bead-bound HbA1c.

(2) Two samples of the lysed red blood cells in citrate buffer can be coulometrically assayed in two chambers. The total $HbO_2$ would be measured coulometrically in the first chamber. Immobilized HbA1c-specific antibody would be in the second chamber. Either of the two (HbO or the immobilized antibody) would capture HbA1c without capturing Hb. After rinsing or passage of citrate buffer through the second chamber (e.g., by repeatedly filling through capillary action and touching the edge of the chamber to filter paper), the second chamber would contain only $HbA1cO_2$. The $HbA1cO_2$ would be assayed coulometrically based on its electroreduction reaction, $4H^+ + 4e^- + HbA1cO_2 \rightleftharpoons 2H_2O + HbA1c$. The HbA1c/Hb ratio could then be calculated from the two coulometric measurements.

(3) This method is like that of method (2) above, except that the two coulometric measurements would be performed in a single chamber. The chamber, which would contain the immobilized HbA1c capture agent, would be filled with a citrate solution of the lysed red blood cells. First, the total $HbO_2$ would be coulometrically measured. Next, the unbound Hb, but not the bound HbA1c, would be rinsed out, the HbA1c would be re-equilibrated with air, and its amount would be coulometrically measured.

Thus, in one form of the invention, the assay can comprise a method of determining the ratio of HbA1c to total Hb in blood, the method comprising the steps of obtaining a blood sample; electrochemically determining the total amount of hemoglobin in the sample; electrochemically determining the amount of HbA1c in the sample; and calculating the ratio of HbA1c to total hemoglobin. In a preferred form, the method of electrochemically determining the total amount of hemoglobin in the sample is accomplished by placing the sample in an electrochemical cell in which, at the cathode, a cathode enzyme is bound. Binding may be accomplished using a redox polymer. In this method, it is preferred that the enzyme be a laccase or a BOD which will electrooxidize oxygen bound to the hemoglobin to water. The hemoglobin content is determined from the oxygen content.

In another form of the invention, the electrochemical determination of HbA1c fraction can be accomplished by one of two methods. In a first method, the A1c-containing fraction of the hemoglobin is separated by physical means, such as by use of an HbA1c-specific antibody. Under appropriate conditions, the HbA1c, then present in the form of $HbA1cO_2$, can be electrochemically determined by electroreduction of the oxygen (again with an enzyme selected to accomplish the four-electron reduction of oxygen). In a second method, the glycated protein (in the form of a fructosyl amine) can be directly oxidized on crosslinked, poly(N-vinyl imidazole)-based redox polymer films (without an enzyme) of sufficiently positive oxidizing potential. Alternatively, enzymatic electrooxidation of the fructosyl amines can be used for this part of the determination.

Thus, the invention comprises an electrochemical method for the determination of HbA1c (or a ratio of HbA1c/Hb) comprising the steps of determining from a starting sample, in an electrochemical cell, the total amount of hemoglobin (e.g., by measuring bound oxygen), separating the HbA1c component from the sample using an HbA1c-capturing agent, and measuring hemoglobin content in the captured or non-captured portion of the sample.

EXPERIMENTAL EXAMPLES

The following examples are provided to demonstrate biological fuel cells 100, and particular cathodes 104, that were experimentally produced in accordance with embodiments of the invention. Experimental Example 1 is reported in Mano et al., *An Oxygen Cathode Operating in a Physiological Solution*, J. Am. Chem. Soc. 2002, 124, 6480-6486, and Experimental Example 2 is reported in Mano et al., *On the Relationship between the Characteristics of Bilirubin Oxidases and O Cathodes Based on Their "Wiring"*, J. Phys. Chem. B 2002, 106, 8842-8848. The following examples include the chemicals and materials used in the experiment, the techniques used to assemble the electrodes, the results of the experiments, as well as discussions of the results. It should be noted that these experiments are provided herein mainly for illustrative purposes, and should not be construed as placing limitations on the invention.

Experimental Example 1

M.v.-BOD on the Cathode

Chemicals and Materials:

Bilirubin oxidase (EC 1.3.3.5) from *M. Verrucaria*, catalase from bovine liver (EC 1.11.1.6), uric acid (sodium salt), spermine (hydrochloride salt), neomycin, gentamycin, 1,4,8,11-tetraazacyclotetradecane (cyclam), L-sodium ascorbate, 4-acetaminophen, $NaIO_4$, NaCl, NaOH, KCNS, KBr, $MgCl_2$, $CaCl_2$, and NaF were purchased from Sigma (St. Louis, Mo.). Poly(ethylene glycol) (400) diglycidyl ether (PEGDGE) was purchased from Polysciences Inc. (Warrington, Pa.). A fresh solution of BOD in pH 7.4 20 mM phosphate buffer (PB) was prepared daily. The uric acid was dissolved in dilute NaOH and then neutralized with dilute $H_3PO_4$ to yield a 10 mM aqueous solution. The electrochemical measurements were performed in phosphate buffered saline (PBS) (pH 7.4 20 mM phosphate-buffered 0.15 M NaCl) except in the experiments where the pH and anion dependence of the steady-state electroreduction of $O_2$ were studied. In these, borate, citrate, acetate, phosphate, and Tris buffers were employed. All solutions were made with deionized water that was passed through a purification train (Sybron Chemicals Inc., Pittsburgh, Pa.). Carbon cloth (Toray TGPH-030) was received, as a sample, from E-TEK (Somerset, N.J.). Ultrapure $O_2$ and argon were purchased from Matheson (Austin, Tex.).

Synthesis of the Redox Polymer PAA-PVI-[Os(4,4'-dichloro-2,2'-bipyridine)$_2$Cl]$^{+2+}$ 4,4'-Dinitro-2,2'-bipyridine N,N'-dioxide was prepared as described in Anderson, S.; Constable, E. C.; Seddon, K. R.; Turp, E. T.; Baggott, J. E.; Pilling, J. *J. Chem. Soc., Dalton Trans*. 1985, 2247-2250, and Kenausis, G.; Taylor, C.; Rajagopalan, R.; Heller, A. *J. Chem. Soc., Faraday Trans*. 1996, 92, 4131-4135. 4,4'-dichloro-2,2'-bipyridine (dcl-bpy) was synthesized from 4,4'-dinitro-2,2'-bipyridine N,N'-dioxide by modifying the procedure of Maerker et al. (see Anderson, S., supra and Maerker, G.; Case, F. H. J. Am. Chem. Soc. 1958, 80, 2475-2477). $Os(dcl-bpy)_2Cl_2$ was prepared as follows: $(NH_4)_2OsCl_6$ and "dcl-bpy were dissolved in ethylene glycol in a 1:2 molar ratio and refluxed under argon for 1 hour (yield 85%). The $Os(dcl-bpy)_2Cl_2$ was then complexed with the 1:7 polyacrylamide-poly(N-vinylimidazole) (PAA-PVI) copolymer and purified as described in Zakeeruddin, S. M.; D. M. Fraser, D. M.; Nazeeruddin, M.-K.; Gratzel, M. *J. Electroanal. Chem*. 1992, 337, 253-256. PAA-PVI-[Os(4,4'-dichloro-2,2'-bipyridine)$_2$Cl]$^{+/2+}$ redox polymer was thus synthesized.

Electrodes:

The carbon cloth electrodes were made by the three-step procedure reported in Barton, S. C.; Kim, H.-H.; Binyantin, G.; Zhang, Y.; Heller, A. *J. Phys. Chem*. 2001, 105, 11917-11921. Their substrates were 3 mm-diameter vitreous carbon electrodes mounted in Teflon sleeves. In the first step, the substrates were polished with 0.05 μm $Al_2O_3$ powder (Buehler, Lake Bluff, Ill.) rinsed and sonicated for 10 minutes in ultrapure water. The polishing step was repeated until no voltammetric features beyond water oxidation were observed in a 50 mV/s scan in PBS through the 0.2 and 1.0 V range. The electrodes were then dried in an air stream. In the second step, the 350 μm-thick carbon cloth (nominal 78% void fraction, composed of 10 μm diameter fibers) was cut into 4 mm-diameter disks. These were cemented, using conductive carbon paint (SPI, West Chester, Pa.), to the surface of the substrate electrodes. The substrate bound cloth was made hydrophilic by exposure to a 1 Torr $O_2$ plasma for 5 minutes. The rotating ring-disk electrodes (RRDE), with 3 mm-diameter vitreous carbon disks and platinum rings were similarly made. In these, the platinum electrodes were cycled in 0.5 M $H_2SO_4$ until the voltammograms showed the characteristics of a clean platinum electrode. In the third step, the electrocatalyst was deposited on the carbon cloth. The deposition solution consisted of 10 μL of 10 mg/mL aqueous redox polymer solution, 2 μL of PB, 2 μL of 46 mg/mL BOD in PB, and 2 μL of 7 mg/mL PEGDGE in water. A 5 μL aliquot of the mixed solution was pipetted onto the mounted hydrophilic carbon cloth, which was promptly wetted and penetrated by the solution. The electrodes were cured for at least 18 hours at room temperature before they were used.

Instrumentation and Cell:

The measurements were performed using a bi-potentiostat (CH-Instruments, electrochemical detector model CHI832) and a dedicated computer. The temperature was controlled with an isothermal circulator (Fisher Scientific, Pittsburgh, Pa.). The dissolved $O_2$ concentration was monitored with an $O_2$ electrode purchased from BAS (West Lafayette, Ind.). The electrodes were rotated using a Pine Instruments rotator (Austin, Tex.). The measurements were carried out in a water-jacketed electrochemical cell at 37.5° C. containing 50 mL of PBS. At the start of the experiments, argon was bubbled through the solution for at least 15 minutes, followed by oxygen. To maintain a fixed volume of solution in the cell, the bubbled gases were pre-saturated with water by passage through a bubbler, which also contained PBS. The potentials were measured versus a commercial Ag/AgCl (3 M KCl) reference electrode. The counter electrode was a platinum wire (BAS). In the coulometric measurements, the scan rate was 1 mV/s.

BOD Assay:

The absorption spectra of the BOD solutions were measured at 25° C. with an Agilent 8453 UV-visible spectrophotometer following the procedure of Hirose (see Hirose, J.; Inoue, T.; Sakuragi, H.; Kikkawa, M.; Minakami, M.; Morikawa, T.; Iwamoto, H.; Hiromi, K. *Inorg. Chim. Acta* 1998, 273, 204-212). The concentration of BOD was calculated using its reported molar absorption coefficient of 3870 $M^{-1} cm^{-1}$ at 610 nm.

Results:

The open-circuit potential of a vitreous carbon electrode on which BOD (without redox polymer) was adsorbed was +360 mV versus Ag/AgCl in pH 7.4 PBS under 1 atm $O_2$ at 37.5° C. or −196 mV versus the potential of the reversible $O_2/H_2O$ under the same conditions. The open-circuit potential of a similar electrode, but with a thin, adsorbed film of the electrostatic adduct of the redox polymer and BOD, was remarkably higher, +530 mV versus Ag/AgCl, only −26 mV versus the potential of the reversible $O_2/H_2O$ electrode. No spectroscopic evidence was found for complex formation between the copper ions of BOD and the polymer. When the water-soluble copolymer of acrylamide and N-vinylimidazole was added to the BOD solution in PB, the spectrum of the enzyme did not change.

A cyclic voltammogram of the composite wired BOD-coated carbon cloth electrode, with a coating consisting of 44.6 wt % BOD, 48.5 wt % polymer, and 6.9 wt % PEGDGE, under argon at 50 mV/s in PBS at 37.5° C., was produced. The voltammogram is characteristic of a polymer-bound osmium complex with an apparent redox potential of +350 mV versus Ag/AgCl. At 1 mV/s scan rate, the voltammogram exhibited a symmetrical wave, with only slight separation of the oxidation and reduction peaks ($\Delta E_P$=5 mV). At 50 mV/s the separation was substantially increased ($\Delta E_P$=53 mV). The width of the peaks at half-height, $E_{whm}$, was 90 mV, close to the theoretical width of 90.6 mV for an ideal Nernstian one-electron-transfer reaction. In contrast with wired laccases, where $\Delta E_P$ and $E_{whm}$ increased with the PEGDGE weight fraction in the catalyst, $\Delta E_P$ and $E_{whm}$ did not vary with the PEGDGE weight fraction in the wired BOD electrodes. As will be shown below, the kinetic limit of current density of the wired BOD electrodes depended, however, on the weight fraction of the PEGDGE crosslinker. Upon 4-hour cycling of the potential at 50 mV/s between 0.0 and +0.5 V versus Ag/AgCl, the heights of the voltammetric peaks of the electrodes rotating at 1000 rpm decreased only by less than 5%, at 37.5° C.

The reproducibility of the $O_2$ electroreduction currents of the electrodes rotating at 1000 rpm was ±10% or better both for different batches (n=4) and within batches (n=12). When the electrodes were rotated at 4000 rpm, the reproducibility was only ±28% between the batches and ±20% within the batches.

Because two-electron BOD-catalyzed electroreduction of $O_2$ to $H_2O_2$ might compete with the desired four-electron reduction, production $H_2O_2$ was tested for using RRDEs having wired BOD carbon cloth disks and platinum rings. If $H_2O_2$ were produced on the disk, it would have been detected at the ring poised at +0.750 mV versus Ag/AgCl, the $H_2O_2$ being electrooxidized to $O_2$ on the platinum ring at this potential (a similar experiment was performed to investigate the formation of $H_2O_2$ during the electroreduction of $O_2$ on disks of RRDE electrodes modified with cytochrome c.).

When $O_2$ was electroreduced on the disk at increasing current densities of between 0 and 5 mA/cm², the ring current remained unchanged and was negligibly small, showing that $H_2O_2$ was not produced on the disk. Furthermore, catalase, which would have decomposed any $H_2O_2$ that might have been produced into $O_2$, had no effect on the ring current, confirming that $H_2O_2$ was not a byproduct of the electroreduction of $O_2$ to water. After 10 hours of $O_2$ electroreduction at approximately 1 mA current, the 50 mL solution of the cell tested negative for $H_2O_2$ in a calorimetric ABTS-horseradish peroxidase test that would have detected 1 μM $H_2O_2$.

The dependence of the current density I on the square root of the angular velocity of the rotating electrode, $\omega^{1/2}$, was determined. Up to 3500 rpm, where the current density reached 8.8 mA/cm², the current increased linearly with $\omega^{1/2}$ in accordance with the Levich equation, showing that it was $O_2$-transport-limited under 1 atm $O_2$ when the electrode was poised at +300 mV versus Ag/AgCl. Above 3500 rpm, the current density continued to increase with $\omega^{1/2}$, but no longer linearly, until it reached the kinetic limit of 9.1 mA/cm².

The optimal composition of the electrocatalyst was determined for electrodes rotating at 1000 rpm and poised at +300 mV versus Ag/AgCl. In the first group of experiments, the crosslinker (PEGDGE) was fixed at 6.9 wt %, and the total loading of all film components was fixed at 0.6 mg/cm². The dependence of the current density of BOD through the 20 to 70 wt % range was determined. From 20 to 45 wt %, the current density increased with the weight percentage of BOD, reaching 4.6 mA/cm² at 45.2 wt %. Above 50 wt % BOD, the current density declined rapidly. At 60 wt % BOD, precipitation was observed. The precipitation is attributed to the formation of a charge-neutral electrostatic adduct between the cationic polymer and the anionic enzyme (pI=4.1). In experiments where the weight percentage of the cross-linker was varied, while the BOD to redox polymer weight ratio was fixed at 1:1, the optimal PEGDGE weight percentage was found to be 6.9. The resulting optimal catalyst was composed of 44.6 wt % BOD, 48.5 wt % polymer, and 6.9 wt % PEGDGE at 0.6 mg/cm$^2$ total loading. The effect of the total loading on the kinetic limit of the catalytic current was not optimized, because the optimum would have varied with the ratios of the components.

Unlike in the cases of wired glucose oxidase and of wired laccases, crosslinking by periodate oxidation of the BOD oligosaccharides did not lead to useful wired BOD electrodes, even though BOD contains 6.3 wt % carbohydrate.

The pH dependence of the steady-state current density of $O_2$ electroreduction was measured with the electrode poised at +300 mV versus Ag/AgCl in 0.15 M NaCl while the electrode rotated at 1000 rpm. Phosphate, borate, citrate, or Tris was added at 20 mM concentration to maintain the desired pH. The dependence of the current on the pH was determined. The current density increased with pH until it reached a plateau at pH 7.5 and then declined above pH 10.5. In the pH 6-10.5 range, the current density was nearly independent of pH, varying by less than ±10%. Up to pH 9, there was no irreversible change in the current characteristics; above pH 10.5, the drop in the current density was irreversible.

Because copper-binding anions, particularly halide anions, inhibit the laccases and because blood contains 0.14 M chloride, the effect of added anions was investigated. In these experiments, the electrode rotated at 1000 rpm and was poised at +300 mV versus Ag/AgCl in a pH 7.4, 20 mM phosphate buffer solution. The current density was nearly independent of the concentration of chloride, added as NaCl, through the 0-1 M range. Above 1.5 M NaCl concentrations, a decline in the current density was, nevertheless, observed. When bromide was added, the current density declined monotonically as the KBr concentration was raised from 0 and 1 M. At 1 M KBr, the current density was about 25% lower than in the absence of bromide. A steeper decline was again observed at >1.5 M KBr concentration. Adding of fluoride (as NaF) inhibited the electroreduction of $O_2$, about 30% of the current density being lost when the concentration of fluoride was raised from 0 to 0.5 M and about 90% being lost when the concentration was further raised to 1 M. Thiocyanate, added as KCNS, strongly inhibited the electroreduction, the current density dropping to 0 already at 0.25 M KCNS. The maximum current density was about the same when the solutions were buffered at pH 7 with Tris, acetate, or phosphate.

The temperature dependence of the current density of the electrode poised at +300 mV versus Ag/AgCl, rotating at 1000 rpm in PBS under 1 atm $O_2$ was determined. The current density increased with temperature up to 60° C. and then declined rapidly. The increase was reversible only up to 50° C., the enzyme being denatured at higher temperatures. The Arrhenius plot (not shown) of the temperature dependence yielded an activation energy of $E_{act}$=28.2 kJ/mol. The observed activation energy for the denaturing of the enzyme was 77 kJ/mol.

When rotating at 4000 rpm, where the shear stress on the rim on the fiber cloth was 0.7 N/m$^2$, the electrodes were mechanically unstable. For this reason, their stability was tested at 300 rpm, where the current was $O_2$ transport limited. At 300 rpm, the shear stress acting on the rim of the 4 mm diameter electrode was $1.4 \times 10^{-2}$ N/m$^2$. The time dependence of the current density of an electrode poised at +300 mV versus Ag/AgCl rotating at 300 rpm in PBS under 1 atm $O_2$ at 37.5° C. was determined. In the first six days of operation, the current dropped by less than 10% per day. The initial 2.4 mA/cm$^2$ current density dropped to 1.3 mA/cm$^2$ after six days of continuous operation. After storage of the dry electrodes for 1 month at 4° C. under air, 95±3% of the initial current density was retained. The presence of electrooxidizable blood constituents did not harm the electrodes. A transient 5% increase in the current density was observed when either 0.1 mM ascorbate or 0.1 mM ascorbate and 0.17 mM acetaminophen was added, and a transient 25% increase in current density was observed with 0.48 mM urate in the solution.

Potentials:

Xu et al. measured spectrophotometrically the redox potential of an aerated pH 5.3 solution of recombinant *M. Verrucaria* BOD at 20° C., reporting +260 mV versus Ag/AgCl or −440 mV relative to the potential of the reversible $O_2/H_2O$ electrode at the same pH. In pH 7.8 50 mM Tris buffer, others have reported a potential of +373 mV versus Ag/AgCl at ambient temperature, −174 mV versus the reversible $O_2/H_2O$ electrode potential at this pH. The open-circuit potential of the $O_2$ electrode made by adsorbing BOD on vitreous carbon was +360 mV versus Ag/AgCl under 1 atm $O_2$ at 37.5° C. and at pH 7.4, consistent with the latter value. This potential was −196 mV versus that of the reversible $O_2/H_2O$ electrode under these conditions. The open circuit potential of the wired BOD electrode, made by cross-linking the electrostatic adduct of BOD, a polyanion above pH 4.1, and a redox polycation, on carbon cloth, was 530 mV versus Ag/AgCl, only 26 mV below that of the reversible $O_2/H_2O$ electrode, at pH 7.4 under 1 atm $O_2$ and at 37.5° C. Two redox polycations that can be used here are shown in FIGS. 6A and 6B. The wiring of the BOD caused a remarkable increase in potential. The redox potential of the PAA-PVI-[Os(4,4'-dichloro-2,2'-bipyridine)$_2$Cl]$^{+/2+}$ wire (shown in FIG. 6) was +350 mV versus Ag/AgCl or −180 mV versus the pH 7.4 open-circuit potential of the wired BOD electrode under 1 atm $O_2$.

Voltammetric Characteristics:

The slight separation of the voltammetric peak heights at 1 mV/s scan rate is indicative of a reversible surface-bound couple. From the linear dependence of the peak heights on the scan rate, the redox couples of the polymer were determined to be surface-confined. The voltammetric peaks were narrower and less separated than those in the earlier PVI-Os(tpy)(dme-bpy)$^{2+/3}$-based laccase electrode, where $\Delta E_P$ was 120 mV. The difference is attributed to faster charge transport through the wire of this study. Repetitive cycling over a 4-hour period at 37.5° C. did not change the shape of the voltammograms of the electrodes rotating at 1000 rpm, and their peak currents decreased only by less than 5%.

Reproducibility:

When the electrodes rotated at 1000 rpm, the apparent batch-to-batch reproducibility, as well as the within-the-batch reproducibility, of the $O_2$ electroreduction currents was better than ±10%. This reproducibility does not necessarily imply that the composite catalysts were identical within ±10%, because at 1000 rpm the current was limited by $O_2$ transport, not by the kinetics of the electrocatalyst. When the electrodes were rotated at 4000 rpm, where the currents were already limited by the kinetics of the catalytic films, but the electrodes were already mechanically unstable, the reproducibility was only ±28% between the batches and ±20% within the batches.

Composition:

The optimal enzyme-to-polymer weight ratio was near 1:1. At a lower weight fraction of enzyme, the current was limited by the BOD-catalyzed rate of $O_2$ reduction. When the weight fraction of enzyme was higher, the current was limited by the electronic resistance of the film, the redox polymer being an electron conductor and the enzyme an insulator. Above 60 wt % BOD, where the electrostatic adduct precipitated, the increased resistance resulted in increased separation of the voltammetric peaks. The observed optimal weight ratio is that of the composition where the upper limits of three currents are equal, a first current based on the flow of electrons from the electrode to the redox polymer, a second current based on the flow of electrons from the redox polymer to the BOD, and a third current based on the flow of electrons from the BOD to $O_2$. The optimal ratio decreases when the maximum turnover rate of the enzyme is higher and decreases when electrons diffuse more rapidly through the redox polymer. The ratio also depends on the nature of the bond between the wire and the enzyme, which determines the maximum electron current from the redox polymer to BOD. In the absence of bonding, the BOD and the redox polymer would phase-separate, the entropy of mixing of two macromolecules being too low prevent their separation. As discussed above, intimate contact between the electrostatically bound BOD and its wire lowers the kinetic resistance for electron transfer from the wire to BOD.

Crosslinking reduces the segmental mobility on which the electron conduction in the redox polymer films depends. Because electrons diffuse as they are transferred when reduced and oxidized redox centers collide, the highest electron diffusivities are being reached when the film is not crosslinked. However, in absence of crosslinking, the films dissolve, and when inadequately crosslinked, they are sheared off the rotating electrodes. With 6.9 wt % PEGDGE cross-linker, the films were mechanically stable at 300 rpm where the maximum shear stress at the rims of the electrodes was $1.4 \times 10^{-2}$ N/m$^2$. At this angular velocity, the current density was 2.4 mA/cm$^2$.

Polarization:

Electroreduction of $O_2$ started at the open-circuit potential of the wired BOD electrode, +530 mV versus Ag/AgCl. When the electrode rotated at 4000 rpm where, as will be shown below, the current was no longer $O_2$-transport-Limited, the current density was 6.8 mA/cm$^2$ at +380 mV versus Ag/AgCl (−176 mV versus the potential of the reversible $O_2/H_2O$ electrode at the same pH) and the current density reached 9.1 mA/cm$^2$ at 300 mV versus Ag/AgCl, −276 mV versus the reversible potential. The value of 6.8 mA/cm$^2$ at −176 mV versus the potential of the reversible $O_2/H_2O$ electrode represents a more than 13-fold increase over current density reported by Tsujimara et al., (see Tsujimura, S.; Tatsumi, H.; Ogawa, J.; Shimizu, S.; Kano, K.; Ikeda, T. *J. Electroanal. Chem.* 2001, 496, 69-75), whose solution was not a physiological buffer, and whose cathodes operated only for a few hours.

Mass Transport and Kinetics:

The Levich-Koutecky plot for electrode rotating at an angular velocity $\omega$ demonstrates that the Levich equation $I=0.62 \, nFAcD^{2/3}v^{-1/6}\omega^{1/2} \, \omega^{1/2}$ is rigorously obeyed up to 3500 rpm, where the current density is 8.8 mA/cm$^2$. The correspondence between the measured and the predicted currents is exact for the $O_2$ diffusivity $D=2.4 \times 10^{-5}$ cm$^2$/s$^1$, the $O_2$ solubility $c=1.07 \times 10^{-6}$ mol/cm$^3$, and the kinematic viscosity $v=0.091$ cm$^2$/s$^1$ of the 0.15 M NaCl solution at 37.5° C. when n, the number of electrons electroreducing the $O_2$, equals 4 and the area A is 0.126 cm$^2$. Above 3500 rpm, the current is controlled by the kinetics of the electrocatalytic reaction. When the electrode rotates at 4000 rpm and the current is kinetically controlled, the measured Tafel slope is −122 mV/decade, and the theoretical for $O_2$ electroreduction at 37.5° C.

Absence of Inhibition in Physiological Solution:

The pH dependence of the current density of the wired BOD electrode differed from the pH dependence of the maximal turnover rate $V_{max}$ of the dissolved enzyme. When the enzyme is dissolved, $V_{max}$ was high only through the pH 6-8 range. $V_{max}$ declined rapidly at both higher and lower pH, only one-third of $V_{max}$ being retained at pH 9.26. In contrast, the wired BOD electrode retained its high current density through the pH 6-10 range. Importantly, the variation of the current was negligibly small within the pH 7.35-7.45 range of normal human arterial blood. Above pH 10.5, the electrode was irreversibly damaged because of enzyme denaturation. The observed damage above pH 10.5 is consistent with results of Samejima et al., who found, by tracking the circular dichroism as a function of pH, that the enzyme is denatured upon ionization of its tyrosine residues. The voltammetric characteristics of the redox polymer did not change up to pH 11.

Laccases are strongly inhibited by halide anions, including the chloride anion, because these bind with their catalytic type II Cu centers and prevent electron transfer from their type I Cu to their type III Cu clusters. The current density of the wired laccase electrodes declined at pH 5 by 60% when the chloride concentration was raised from 0 to 0.1 M. In contrast, the current density of the wired BOD electrode declined only by 6%. The loss remained small even in 1 M NaCl at pH 7.4 (FIG. 10). Other copper-binding anions inhibited the electroreduction of $O_2$, with inhibition declining in the order CNS$^-$>>F$^-$>>Br$^-$>Cl$^-$. This order is only in partial agreement with the order CNS$^-$>F$^-$>>Cl$^-$>Br$^-$ of solution-phase inhibition of the free enzyme reported by Hirose et al. (see Hirose, J.; Inoue, T.; Sakuragi, H.; Kikkawa, M.; Minakami, M.; Morikawa, T.; Iwamoto, H.; Hiromi, K, *Inorg. Chim. Acta* 1998, 273, 204-212) for BOD and by Xu et al. (see Xu, F.; Shin, W.; Brown, S. H.; Walhleithner, J. A.; Sundaram, U. M.; Solomon, E. I. *Biochim. Biophys. Acta* 1996, 1292, 303-311 and Xu, F. Biochemistry 1996, 35, 7608-7614) for laccases. Significantly, the inhibition of the wired BOD cathode by chloride at its 0.096-0.106 M concentration in normal human-blood was so small that physiological variation in chloride concentration will not affect the $O_2$ electroreduction current. The electrode differed in this respect from the dissolved BOD-based cathode of Tsujimura et al., the current of which depended strongly on the concentration of KCl in the 0-0.1 M range. The observed partial loss of $O_2$ electroreduction current at very high chloride concentration (>1.5 M NaCl) is not attributed to specific binding of chloride to copper centers of BOD. Its likely cause is the screening of the charges of the electrostatically bound polycationic and polyanionic segments of the cross-linked redox polymer-BOD adduct at high ionic strength, causing their dissociation and making the wiring of the enzyme ineffective.

Temperature Dependence:

The $O_2$ electroreduction current increased with the temperature up to 60° C. when the rate of increase was about 110° C./h$^1$ and declined rapidly when the temperature exceeded 60° C. The decline is attributed to the denaturation of the enzyme. The apparent stability of the wired enzyme electrode was better than that of the dissolved enzyme, for which an optimal temperature of 40° C. was reported. The apparent activation energy for $O_2$ electroreduction was $E_{act}$=28.2 kJ/mol$^1$ for the pH 7.4 solution with the electrode rotating at 1000 rpm under 1 atm $O_2$, where the current was $O_2$ transport controlled. Because the current was $O_2$-transport-limited at 1000 rpm, the 28.2 kJ/mol$^1$ value represents the activation energy for diffusion of oxygen in the solution. The 77 kJ/mol$^1$ activation energy for current loss is similar to that for the thermal denaturation of other enzymes.

Stability:

At high angular velocity (>1000 rpm), the electrode was mechanically unstable, its catalytic film being sheared off. When the electrode, poised at +300 mV versus Ag/AgCl, was rotated at 300 rpm under 1 atm $O_2$ at 37.5° C., it lost less than 10% of its current per day of continuous operation for 6 days. The wired BOD electrode was far more stable than suggested by Tanaka's study of the stability of the dissolved enzyme, showing loss of half the activity after 1 hour in phosphate buffer at 37° C. (see Tanaka, N.; Murao, S. *Agric. Biol. Chem.* 1982, 46, 2499-2503). It was also more stable than that of an immobilized BOD electrode used in the clinical monitoring of the concentration of bilirubin. The half-life of the clinical bilirubin-monitoring electrode was much shorter than that of the cathode of this study, only 17 hours at 37° C. and 8 hours at 40° C.

The most readily cathode-electooxidized constituents of blood, urate, ascorbate and acetaminophen, at their physiological concentrations, did not damage the cathode poised at +300 mV/Ag/AgCl in PBS buffer at 37.5° C. When 0.1 mM ascorbate was added, or 0.1 mM ascorbate and 0.17 mM acetaminophen were added, the current transiently decreased by 5%, and when 0.48 mM urate was added, the decrease was 25%. While Binyamin et al. showed that the electrooxidative polymerization of urate in a redox polymer film with a higher density of cationic sites and thus a higher urate concentration in the film caused degradation of its electrocatalytic properties, no such damage was observed in the present films (see Binyamin, G.; Chen, T.; Heller, A. *J. Electroanal. Chem.* 2001, 500, 604-611).

Conclusion:

In Experimental Example 1, the first electrode on which $O_2$ is electroreduced to water under physiological conditions at a current density of 9.1 mA/cm$^2$ and at a potential −0.26 V relative to the reversible potential of the $O_2/H_2O$ electrode, is described. The electrode has no leachable components, making it suitable for use in flow systems, and with a yet-to-be-added, thin bioinert film, for use in animals. The electrode could well serve as the cathode of a miniature biofuel cell that might power implanted sensors and actuators for about 1 week.

Experimental Example 2

T.t.-BOD on the Cathode

Chemicals and Materials:

BOD (EC 1.3.3.5, 1.3 U/mg$^1$) from *Trachyderma tsunodae* was a gift from Amano, Lombard, Ill. NaCl, NaOH, KCNS, KBr, $MgCl_2$, $CaCl_2$, and NaF were purchased from Sigma, St. Louis, Mo. Poly(ethylene glycol) (400) diglycidyl ether (PEGDGE) was purchased from Polysciences Inc. (Warrington, Pa.). A fresh solution of BOD in pH 7.4 20 mM phosphate buffer (PB) was prepared daily. The uric acid was dissolved in dilute NaOH then neutralized with dilute $H_3PO_4$ to yield a 10 mM aqueous solution. The electrochemical measurements were performed in pH 7.4 phosphate buffered saline (PBS, 20 mM phosphate, 0.15 M NaCl) except in the experiments where the pH and anion dependences of the steady-state, $O_2$ electroreduction currents were determined. In these, borate, citrate, acetate, phosphate and Tris buffers were employed. All solutions were made with de-ionized water, passed through a purification train (Sybron Chemicals Inc, Pittsburgh, Pa.). Carbon cloth (Toray TGPH-030) was received, as a sample, from E-TEK (Somerset, N.J.). Ultra-pure $O_2$ and argon, were purchased from Matheson (Austin, Tex.). The synthesis of the BOD-wiring redox polymer PAA-PVI-[Os(4,4'-dichloro-2,2'-bipyridine)$_2$Cl]$^{+/2+}$ was previously reported (see Mano, N.; Kim, H.-H.; Zhang, Y.; Heller, A. *J. Am. Chem. Soc.* 2002).

Carbon Cloth Electrodes:

The carbon cloth electrodes were made by the three-step procedure reported in Barton, S. C.; Kim, H.-H.; Binyamin, G.; Zhang, Y.; Heller, A. *J Phys. Chem.* 2001, 105, 11917, and Mano, N.; Kim, H.-H.; Zhang, Y.; Heller, A. *J. Am. Chem. Soc.* 2002. A deposition solution was prepared by mixing 10.3 µL of a 10 mg/mL$^1$ aqueous redox polymer solution, 2 µl of PBS, and 1.7 µL of 55 mg/mL$^1$ BOD in PBS and 2 µl of 7 mg/mL$^1$ PEGDGE in water. A 5 µl aliquot of the mixed solution was pipetted onto the mounted hydrophilic carbon cloth, which was promptly wetted and penetrated by the solution. The electrodes were cured for at least 18 hours at room temperature before they were used.

Carbon Fiber Electrodes:

Prior to coating, the 7 µm-diameter fibers (0.0044 cm$^2$) were made hydrophilic by exposure to 1 Torr $O_2$ plasma for 3 minutes. The cathodic catalyst consisted of the crosslinked adduct of 44.4 wt % Tt-BOD, 49 wt % redox polymer, and 6.6 wt % PEGDGE.

Instrumentation and Cell:

The measurements were performed using a bipotentiostat (CH-Instruments, Austin, Tex., Model #CHI832) and a dedicated computer. The temperature was controlled with an isothermal circulator (Fisher Scientific, Pittsburgh, Pa.). The dissolved $O_2$ concentration was monitored with an oxygen $O_2$-electrode purchased from BAS (West Lafayette, Ind.). The electrodes were rotated using a Pine Instruments Rotator (Austin, Tex.). The measurements were carried out in a water-jacketed electrochemical cell at 37.5° C. containing 50 mL PBS. At the start of the experiments argon was bubbled through the solution for a least 15 min, followed by oxygen. To maintain a fixed volume of solution in the cell the bubbled gasses were pre-saturated with water by passage through a bubbler, which also contained PBS. The potentials were measured versus a commercial Ag/AgCl (3 M KCl) reference electrode. The counter electrode was a platinum wire (BAS, West Lafayette, Ind.). In the coulometric measurements the scan rate was 1 mV/s$^1$.

BOD Assay:

The absorption spectra of the BOD solutions were measured at 25° C. with an Agilent 8453 UV-Visible spectrophotometer following the procedure of Amano (Lombard, Ill.).

Results:

The open-circuit potential of the vitreous carbon electrode on which Tt-BOD (without redox polymer) was adsorbed was +440 mV versus Ag/AgCl in pH 7.4 PBS under argon at 37.5° C. (−116 mV versus the potential of the reversible $O_2$/420 electrode). The open-circuit potential of a similar electrode, but with a thin adsorbed film of the electrostatic adduct of the redox polymer and Tt-BOD, was remarkably higher, +530 mV versus Ag/AgCl (−26 mV versus the potential of the reversible $O_2/H_2O$ electrode). No spectroscopic evidence was found for complex formation between the $Cu^{+/2+}$ ions of BOD and the redox polymer. When the water-soluble co-polymer of acrylamide and N-vinylimidazole was added to a solution of Tt-BOD in PBS, the spectrum of the enzyme did not change.

A cyclic voltammogram of the composite wired Tt-BOD coated carbon cloth electrode, with a coating consisting of 44.4 wt % BOD, 49 wt % polymer and 6.6 wt % PEGDGE, under argon at 50 mV/s$^1$ in PBS buffer at 37.5° C., was produced. The voltammogram was characteristic of the Os complex bound to the redox polymer, with an apparent redox potential of +350 mV versus Ag/AgCl. At 1 mV/s[1] scan rate the voltammogram exhibited a symmetrical wave, with a 25 mV separation ($\Delta E_P$) of the oxidation and reduction peaks. At 50 mV/s[1] the separation increased to 110 mV. The width of the peaks at half height, $E_{whm}$, was 113 mV, whereas in the wired Mv-BOD it was 90 mV, close to the theoretical width of 90.6 mV for an ideal Nernstian, one-electron-transfer reaction. As observed earlier in wired laccases, but not in wired Mv-BOD, $\Delta E_P$ and $E_{whm}$ increased with the PEGDGE weight fraction in the catalyst. Upon 4-hour cycling of the potential at 50 mV/s[1] between 0.0 V and +0.5 V versus Ag/AgCl, the heights of the voltammetric peaks of the electrodes rotating at 1000 rpm decreased only by less than 6% at 37.5° C.

The reproducibility of the $O_2$ electroreduction currents of electrodes rotating at 1000 rpm under air, or under 1 atm $O_2$, was ±10% or better, both for different batches (n=4) and within batches (n=12). When the electrodes were rotated at 4000 rpm the reproducibility of their currents was ±15% between batches and ±11% within batches.

Because two-electron BOD-catalyzed electroreduction of $O_2$ to $H_2O_2$ might compete with the desired four-electron reduction, the solutions were tested for accumulation of $H_2O_2$. No trace of $H_2O_2$ was detected when they were assayed by established procedures.

The dependence of the current I on the square root of the angular velocity of the rotating electrode, $\omega^{1/2}$, was determined. Up to 3000 rpm, where the current density reached 2.74 mA/cm$^2$, it increased linearly with $\omega^{1/2}$, precisely as predicted by the Levich equation, showing that the current was $O_2$-transport-limited in air when the electrode was poised at +300 mV versus Ag/AgCl. Above 3000 rpm the current continued to increase with $\omega^{1/2}$, but no longer linearly, until it reached 2.9 mA/cm$^2$. Under 1 atm $O_2$, at 1000 rpm, the current density reached 3.5 mA/cm$^2$, 30% less than reported for the Mv-BOD cathode, under the same conditions. Under 1 atm $O_2$ and at 4000 rpm, where the current density was no longer mass transport limited, the current density was 4.6 mA/cm$^2$ at +380 mV versus Ag/AgCl and reached its kinetic limit of 6.25 mA/cm$^2$ at 300 mV versus Ag/AgCl. The kinetic limit of the Tt-cathode was approximately 30% lower than that of the Mv-cathode (9.1 mA/cm$^2$).

The optimal composition of the electrocatalyst was determined for electrodes rotating at 1000 rpm and poised at +300 mV versus Ag/AgCl. In the first group of experiments, the crosslinker (PEGDGE) weight percentage was fixed at 6.6 wt %, and the total loading of all film components was fixed at 0.6 mg/cm$^2$. The dependence of the current density on the wt % of Tt-BOD through the 20 to 60 wt % range was determined. Between 10 wt % and 45 wt %, the current density increased with the wt % of Tt-BOD, reaching 3.5 mA/cm$^2$ at 44.9 wt %. Above 47 wt % Tt-BOD, the current density declined rapidly. At 50 wt % Tt-BOD, the adduct of the enzyme (isoelectric point pH 4.1) and the redox polymer, a polycation, precipitated. The precipitation was similar to that observed in the case of GOx and other polyanionic enzymes, and is attributed to the formation of an electrostatic adduct between the polycationic polymer and the polyanionic enzyme. Above 55 wt % BOD, where the electrostatic adduct precipitated, the separation of the voltammetric peaks increased. These results differed sharply from those for Mv-BOD, where precipitation was observed only above 60 wt % and where the decline in current density above 60 wt % was not as sharp. In experiments where the weight percentage of the crosslinker was varied with the Tt-BOD to redox polymer weight ratio fixed at 1:1.1, the optimal PEGDGE wt % was 6.6. Thus, at 0.6 mg/cm$^2$ total loading, the optimized catalyst was composed of 44.4 wt % Tt-BOD, 49 wt % redox polymer, and 6.6 wt % PEGDGE. Because it depended on the composition, the total loading was not optimized.

The pH-dependence of the steady state current density of $O_2$ electroreduction was measured with the electrode poised at +300 mV versus Ag/AgCl in 0.15 M NaCl while the electrode rotated at 1000 rpm. Phosphate, borate, citrate or Tris were added at 20 mM concentration to maintain the desired pH. The current density increased with pH until it reached a plateau at pH 7.5, then declined slightly above pH 10.5. In the pH 6 to 10.5 range, the current density was nearly independent of pH, varying by less than ±10%. Up to pH 10.5, there was no irreversible change in the current characteristics, and above pH 11, the drop in the current was irreversible. The window of operation of the Tt-BOD cathode was up-shifted relative to that of Mv-BOD, from 5-10 to 6-10.5.

Because copper-binding anions, particularly halide anions, inhibit the laccases and because serum and other physiological fluids contain 0.14 M chloride, the effect of added anions was investigated. In these experiments, the electrode was rotated at 1000 rpm while it was poised at +300 mV versus Ag/AgCl in the pH 7.4 20 mM phosphate buffer solution. The current density was nearly independent of the concentration of NaCl through the 0-1 M range. As found also in the case of Mv-BOD, the current density declined above 1.5 M NaCl. When the concentration of KBr was raised from 0 and 1 M, the current density declined monotonously; at 1 M KBr it was approximately 20% lower than at 0 M KBr. A steeper decline was again observed at >1.5 M KBr concentration. Adding of fluoride (as NaF) inhibited the electroreduction of $O_2$, approximately 30% of the current density being lost when the concentration of fluoride was raised from 0 to 0.25 M, and 100% being lost when the concentration was further raised to 0.5 M. Thiocyanate, added as KCNS, strongly inhibited the electroreduction, the current density dropping to nil already at 0.135 M KCNS. The maximum current density was about the same when the solutions were buffered at pH 7 with Tris, acetate or phosphate.

The temperature dependence of the current density of the electrode poised at +300 mV versus Ag/AgCl, rotating at 1000 rpm in PBS under 1 atm $O_2$, was determined. The current density increased with temperature up to 40° C., then declined rapidly above 55° C. With Mv-BOD, the current density increased up to 60° C., then declined rapidly. For both Mv- and Tt-BOD enzymes, the increase was reversible only up to 50° C., the enzymes being denatured at higher temperatures. For Tt-BOD, the Arrhenius plot of the temperature dependence of the current yielded an activation energy of $E_{act}$=34.3 kJ/mol[1]. The observed activation energy for the thermal denaturing of the enzyme was 88.2 kJ/mol[1].

Repetitive cycling over a 4-hour period at 37.5° C. in air or under 1 atm $O_2$ did not change the shape of the voltammograms of electrodes rotating at 1000 rpm, their peak currents decreasing only by less than 5%.

Consistently with earlier results, the carbon cloth electrodes rotating at 4000 rpm (shear stress on the rim 0.7 N/m$^2$) were mechanically unstable. For this reason, the extended stability tests were performed at 300 rpm, where the current was $O_2$-transport-limited. At this angular velocity, the shear stress acting on the rim of the 4 mm-diameter electrode was $1.4 \times 10^{-2}$ N/m$^2$. The time dependence of the current density of an electrode poised at +300 mV versus Ag/AgCl, rotating at 300 rpm in PBS under 1 atm $O_2$ at 37.5° C., was determined. The current dropped by about 5% per day, the current density declining from 1.9 mA/cm$^2$ to 1.4 mA/cm$^2$ after six days of continuous operation. After storage of the dry electrodes for three weeks at 4° C. under air, 95±3% of the initial current density was retained.

The presence of electrooxidizable serum constituents did not harm the electrodes. A transient 5% increase in the current density was observed when either 0.1 mM ascorbate or 0.1 mM ascorbate and 0.17 mM acetaminophen was added, and a transient 18% increase in current density was observed with 0.48 mM urate in the solution.

The polarization curves of miniature carbon fiber cathodes (7 μm in diameter, 2 cm in length) modified with wired Mv-BOD or with wired Tt-BOD in a quiescent air solution at 37.5° C. in PBS were compared. On the Mv-BOD fiber, $O_2$ was electroreduced at +0.25 V versus Ag/AgCl at a current density of 0.73 mA/cm$^2$. On the Tt-BOD fiber, $O_2$ was electroreduced at +0.3 V versus Ag/AgCl at 0.88 mA/cm$^2$.

Open-Circuit Potentials of the Non-Wired BOD Electrodes Under Argon:

The open-circuit potential of the electrode made by adsorbing non-wired Tt-BOD on vitreous carbon, is, under argon, +440 mV versus Ag/AgCl, or −116 mV versus the potential of the reversible $O_2/H_2O$ electrode, while that of Mv-BOD is +360 mV versus Ag/AgCl, or −196 mV versus the potential of the reversible $O_2/H_2O$ electrode. In the absence of redox polymer, the only redox center of BOD exchanging electrons with the carbon electrode is the type I Cu center. This center, unlike the cluster of type II and type III $Cu^{+/2+}$ centers, is close to the periphery of the globular proteins of the two BODs. The type I $Cu^{+/2+}$ center of Mv-BOD differs from that of Tt-BOD in the axial amino acid residue of its $Cu^{+/2+}$ center. In Mv-BOD, the amino acid is methionine; while in Tt-BOD, it is phenylalanine. In the F463 M laccase, mutant replacement of the non-complexing, axial phenylalanine by the weakly complexing methionine decreases the redox potential of the type I $Cu^{+/2+}$ center by 100 mV. In laccases, the redox potential of the type I $Cu^{+/2+}$ center decreases by approximately 100 mV when it is four-coordinated rather than three-coordinated. It is believed that the higher redox potential of Tt-BOD relative to that of Mv-BOD can be attributed to the replacement of the methionine by phenylalanine in the type I $Cu^{+/2+}$ center.

Dependence of the Potential of the Type I BOD $Cu^{+/2+}$ Centers on pH in the Absence of $O_2$:

For a typical Nernstian electrode reaction in which a proton is consumed upon oxidation, the potential is up-shifted at 25° C. by 59 mV when the pH is decreased by one unit. The redox potential of the type I $Cu^{+/2+}$ of Tt-BOD, the centers of which are titrated with $Li_2[Co(2)(2,6\text{-pyridine-dicarboxylate})_2]$, at 25° C. has been measured under anaerobic conditions. In pH 6.8, 50 mM phosphate buffer, the potential was +400 mV versus Ag/AgCl, and in pH 5.0, 0.2 M acetate buffer, it was +442 mV versus Ag/AgCl. The redox potentials of the copper proteins azurin and rusticyanin also increase as the pH is decreased. In contrast, the redox potentials of Mv-BOD decrease as the pH is lowered, possibly because of a structural change leading to a change in the coordination of the $Cu^{+/2+}$.

Open-Circuit Potentials of the Wired BOD Electrodes Under 1 atm $O_2$:

Because in both Mv-BOD and Tt-BOD the electroreduced $O_2$ is reversibly bound to the cluster of type II and type III $Cu^{+/2+}$ centers, this cluster is poised at or near the potential of the reversible $O_2/H_2O$ electrode. At open-circuit potential, where no current flows, it is not required that each of the four electrocatalytic reaction steps be fast. Specifically, it is not necessary that the redox potentials (which are the potentials when the concentrations of the oxidized and the reduced species are equal) increase in each of the following steps: (a) electron transfer from the electrode to $Os^{2+/3+}$ centers of the redox polymer; (b) electron transfer from the $Os^{2+/3+}$ centers to the type I $Cu^{+/2+}$ centers; (c) electron transfer from the type I $Cu^{+/2+}$ centers to the type II and the type III $Cu^{+/2+}$ center-comprising clusters; and (d) electron transfer from the clusters to their bound $O_2$ molecules. When no current flows, each of the centers can increase or decrease its potential, until the potentials are the same, by adjusting the concentration ratio of its oxidized and reduced species, $[Os^{2+}]:[Os^{3+}]$ or $[Cu^+]:[Cu^{2+}]$. For this reason the open-circuit potentials of both the wired Mv and the Tt cathodes are, under 1 atm $O_2$, close to (within less than 30 mV of) the potential of the reversible $O_2/H_2O$ electrode at pH 7.4.

Polarization:

After the redox centers poise themselves near the open-circuit potential by adjusting their $[Os^{2+}]:[Os^{3+}]$ or $[Cu^+]:[Cu^{2+}]$ ratio, the concentration of one or more of the electron donors or acceptors can be so far reduced that the reaction rate, which is the current, becomes very small. In the four-step cascade, this will be avoided, and the overall rate will remain high, when the $[Os^{2+}]:[Os^{3+}]$ and the $[Cu^+]:[Cu^{2+}]$ ratios of each of the centers is not much larger or much smaller than 1. When the ratio is not too far from 1, the potential of the redox center is, by definition, near its Nernstian redox potential. Thus, the current will be high when the redox potentials of the centers are in the order $O_2/H_2O$>(type II and type III) $Cu^{+/2+}$ cluster >type I $Cu^{+/2+}$ center >wire $Os^{2+/3+}$>electrode. The maximum current, which is the short circuit current, is reached when the rates of the four electron-transfer steps are equal. The equalization of the rates necessitates, however, $[Os^{2+}]:[Os^{3+}]$ and $[Cu^+]:[Cu^{2+}]$ ratios somewhat different than 1, because the centers differ in their self-exchange rates and because the concentration of $Os^{2+/3+}$ differs from that of the $Cu^{+/2+}$ centers. Upon adjusting the ratios, the rates of the four steps are equalized and the short circuit current reaches its maximum. Note that for ratios in the 0.1-10 range, the potentials of the centers at short circuit will differ from their redox potentials by −59 to +59 mV.

In a polarization study, $O_2$ was electroreduced on the Mv-BOD fiber at +0.25 V versus Ag/AgCl at a current density of 0.73 mA/cm$^2$, while on the Tt-BOD fiber it was electroreduced at +0.3 V versus Ag/AgCl at 0.88 mA/cm$^2$. The simultaneous gain in potential and current is attributed to the approximately 100 mV higher redox potential of the type I $Cu^{+/2+}$ center of Tt-BOD relative to that of the Mv-BOD. The $O_2$-binding, type II and type III $Cu^{+/2+}$ center-cluster is buried in the globular BOD protein and may not be directly reduced by electron transfer from an $Os^{2+}$-complex of the redox polymer. It is the type I $Cu^{+/2+}$ center that accepts electrons from $Os^{2+}$, as it is nearer to the protein's surface. When the rates of electron transfer between the type I center and the cluster, and between the cluster and its bound $O_2$ are fast, then the current-controlling step is the transfer of electrons from $Os^{2+}$ of the polymer to the type I $Cu^{+/2+}$ center. Increasing the redox potential of the type I $Cu^{+/2+}$ center increases the rate constant of electron transfer by increasing the transfer-driving potential difference. As a result, the rate of $Os^{2+}\to$(type I $Cu^{2+}$) transfer can increase to match the (type I $Cu^+$) (type II $Cu^{2+}$) rate at a lower $[Os^{2+}]:[Os^{3+}]$ ratio, and therefore, when the redox polymer and the electrode are poised at a more oxidizing potential than in the Mv-cathode where the redox potential of the type I center is approximately 100 mV more reducing.

Composition:

The key difference between the optimal Tt and Mv compositions is that the Tt-films contain less enzyme. If the turnover rates of Tt and Mv were similar, the wt % of the 64 kDa Tt would be higher than the approximately 50 wt % of the 52 kDa Mv-cathode, which is its optimal composition. The higher wt % cannot be reached because of precipitation of the electrostatic adduct of the enzyme and the redox polymer above 55 wt % BOD. In the absence of precipitation up to 60 wt % BOD, the Mv-electrodes can have the optimal BOD wt %, which is the wt % where the rates of consumption of electrons by the enzyme and the rate of electron permeation from the electrode to the enzyme are equal. Because there is no difference between the isoelectric points (pH 4.1) of Mv-BOD and Tt-BOD, the abrupt precipitation of Tt at 55 wt % is attributed to electrostatic bonding of clusters of anions on the Tt-globule and the redox polymer, leading to crosslinking. When the redox polymer is highly crosslinked, its segmental mobility, which underlies the transport of electrons (via collisions between reduced and oxidized, redox-couple-carrying segments) is reduced. For this reason, the wired Tt-BOD is a poorer electron conductor, even though the weight fraction of redox polymer in its adduct is higher. The poorer conductivity is evidenced by increased separation of the voltammetric peaks above 55 wt % Tt-BOD.

Crosslinking by PEGDGE further reduces the segmental mobility on which the electron conduction in the redox polymer film depends. Though high electron diffusivities are reached in films that are less crosslinked, the poorly crosslinked films dissolve, or swell excessively, and are sheared off the rotating electrodes. With 6.6 wt % PEGDGE crosslinker, the films were mechanically stable at 300 rpm, where the maximum shear stress at the rims of the electrodes was $1.4 \times 10^{-2}$ N/m². At this angular velocity, the current density was 1.9 mA/cm².

The polarization and the current density of the wired Tt-BOD fiber cathode are considerably improved over those of the wired Mv-BOD fiber cathode. In carbon cloth electrodes, the 4.6 mA/cm² current density at −176 mV versus the potential of the reversible $O_2/H_2O$ electrode represents a nine-fold increase over that of the less stable and chloride-inhibited dissolved Mv-BOD-based $O_2$ cathode.

Voltammetric Characteristics:

When the weight fraction of Tt-BOD exceeded 55 wt %, the current was limited by the high electronic resistance of the film caused by the electrostatic crosslinking of the redox polymer and the polyanionic enzyme, leading to lesser mobility of the redox centers. The $\Delta E_P$=25 mV separation of the voltammetric peaks at 1 mV/s scan rate of the wired Tt-BOD cathode exceeded the 5 mV separation of the Mv-BOD cathodes. The slower charge transport in the Tt-electrode was a consequence of the reduced segmental mobility of in the Tt-films. The 113 mV width of the peaks at half height also exceeded the 90 mV width of the Mv-electrode, also reflecting the loss of segmental mobility.

Reproducibility:

When the electrodes were rotated at 1000 rpm, the apparent batch-to-batch reproducibility, as well as the within-batch reproducibility, of the $O_2$ electroreduction currents were better than ±10%, as they also were for Mv-BOD. This reproducibility does not necessarily imply that the composite catalysts are identical within ±10%, because at 1000 rpm the current is limited by $O_2$ transport, not by the kinetics of the electrocatalyst. When the electrodes were rotated under $O_2$ at 4000 rpm, where the currents are limited by the kinetics of the electrocatalyst, the batch-to-batch reproducibility was ±15% and the within-batch reproducibility was ±11%. The spread was only half that between and within batches of Mv-electrodes, where loss of the catalytic films by shearing worsened the reproducibility at high angular velocity (>1000 rpm). The better reproducibility and stability are attributed to the enhanced electrostatic crosslinking of the enzyme and the redox polymer, which reduces the swelling and improves the mechanical stability of the sheared films.

Absence of Inhibition at Physiological pH and Physiological Chloride Concentration:

The dissolved Tt-BOD electrode retained its current through pH 7 to 10 range and the wired Mv-BOD electrode retained its current through the pH 5 to pH 10 range, while the wired Tt-BOD electrode retained its current through the pH 6 to 10.5 range. The decrease in current above pH 11 is irreversible. This decrease is caused by the denaturation of the enzyme, and is attributed, in the case of Mv-BOD, to the ionization of tyrosine residues. The variation of the current is negligibly small across the pH range of human serum or blood.

At pH 5, the current density of the wired Coriolus hirsutus laccase cathode declined by 60% when the chloride concentration was raised from nil to 0.1 M. Laccases are inhibited by halide anions, including chloride anions, because these anions bind with the type II $Cu^{+/2+}$ centers and slow the transfer of electrons from the type I $Cu^{+/2+}$ center to the type III $Cu^{+/2+}$ pair. The dissolved Tt-BOD cathode is inhibited by chloride at 0.1 M concentration as well. Unlike these cathodes, the wired Tt-BOD cathode is the least inhibited by chloride, its current density declining only by 3% when the chloride concentration is raised from 0 to 0.1 M, while that of the wired Mv-BOD cathode declines by 6%. The loss remains small even at 1 M NaCl. Significantly, the inhibition of the wired Tt-BOD cathode by chloride at its 0.096-0.106 M concentration in normal human blood is so small that physiological variation in chloride concentration will not affect the $O_2$ electroreduction current. Other copper-binding anions inhibit the electroreduction of $O_2$, the inhibition declining in the order $CNS^- > F^- > Br^- > Cl^-$. This order is only in partial agreement with the order $CNS^- >> F^- >> Br^- > Cl^-$ found for the wired Mv-BOD and with the order $CNS^- > F^- >> Cl^- > Br^-$ for the inhibition of dissolved Tt-BOD and for laccases. The order has been attributed, in the case of the dissolved enzymes, to differences in the blockage of the access to their type II and type III $Cu^{+/2+}$ clusters.

The observed partial loss of $O_2$ electroreduction current at very high chloride concentration (>1.5 M NaCl) is not attributed to specific binding of chloride to copper centers of the wired BOD, but to the screening of the charges of the electrostatically bound polycationic and polyanionic segments of the redox-polymer-BOD adduct at high ionic strength, causing their dissociation and making the wiring of BOD less effective.

Temperature Dependence and Stability of the Current:

The $O_2$ electroreduction current increased with the temperature up to 60° C. when the rate of increase was about 10° C./h, and declined rapidly when the temperature exceeded 60° C. The decline is attributed to the denaturation of the enzyme. The wired Tt-BOD cathode was more stable than the cathode made of with the dissolved enzyme, for which an optimal temperature of 45° C. was reported. The apparent activation energy for $O_2$ electroreduction was $E_{act}$=34.3 kJ/mol ($E_{act}$=28.2 kJ/mol for Mv-BOD) at pH 7.4 when the electrode rotated at 1000 rpm under 1 atm $O_2$, and the current was $O_2$-transport controlled. Because the current is $O_2$-transport-limited at 1000 rpm, the 34.3 kJ/mol activation energy is that for the diffusion of oxygen in the solution. Its value is consistent with the temperature dependence of the diffusivity of $O_2$. The thermal-denaturation-caused 88.2 kJ/mol activation energy for current loss of the Tt-cathode shows that the cathode is more stable than the Mv-cathode (77.2 kJ/mol), explaining why the Tt-cathode loses only 5% of its current per day of operation at 37.5° C., while the Mv-cathode loses 10%.

The wired Tt-BOD cathode is much more stable than the cathode of Tanaka made with the dissolved enzyme, which had a half-life of one hour in phosphate buffer at 37° C. It was also more stable than that of an immobilized-BOD electrode used in the clinical monitoring of the concentration of bilirubin having a half life of 17 hours at 37° C. and 8 hours at 40° C.

At their physiological concentrations the most readily electooxidized constituents of blood urate, ascorbate and acetaminophen do not damage the Tt-cathode when poised at +300 mV/Ag/AgCl in PBS at 37.5° C. When 0.1 mM ascorbate was added, or 0.1 mM ascorbate and 0.17 mM acetaminophen were added, the current transiently decreased by 5%, and when 0.48 mM urate was added, the current decreased by 22%. While the electrooxidative polymerization of urate in a redox polymer film with a higher density of cationic sites and thus a higher urate concentration in the film causes severe fouling, the present films were not fouled by urate electropolymerization.

Conclusion: Wired BOD films catalyze the electroreduction of $O_2$ to water under physiological conditions. When the oxygen electroreducing cathodes are poised at potentials that are as little as −136 mV reducing relative to the potential of the reversible $O_2/H_2O$, the current density of the wired Tt-BOD cathode exceeds 2 mA/cm$^2$ at 37° C. The cathode operates for six days, with 5% of the current being lost per day. The improvement in operating current density and potential is attributed to the higher redox potential of the type I $Cu^{+/2+}$ redox center of Tt-BOD, and the improved stability is attributed to the enhanced electrostatic bonding of Tt-BOD and its polymeric wire.

Experimental Example 3

Characteristics of a Miniature Glucose Oxygen Biofuel Cell and its Operation in a Living Plant In this experimental example, the temperature, pH, glucose concentration, NaCl concentration, and operating atmosphere dependence of the power output of a compartmentless, miniature glucose-$O_2$ biofuel cell, comprised only of two bioelectrocatalyst-coated carbon fibers, each of 7-μm diameter and 2-cm length (Mano, N.; Mao, F.; Heller, A. J. Am. Chem. Sec. 2002, 124, 12962), was investigated. The bioelectrocatalyst of the anode consists of glucose oxidase from *Aspergillus niger* electrically wired by polymer I, having a redox potential of −0.19 V vs Ag/AgCl. That of the cathode consists of bilirubin oxidase from *Trachyderma tsunodae* wired by polymer II, having a redox potential of +0.36 V vs Ag/AgCl (Mano, N.; Kim, H.-H.; Zhang, Y.; Heller, A. J. Am. Chem. Soc. 2002, 124, 6480. Mano, N.; Kim, H.-H.; Heller, A. J. Phys. Chem. B2002, 106, 8842). Implantation of the fibers in a grape leads to an operating biofuel cell. The cell, made of 7-μm diameter, 2-cm long fibers, produces in the grape 2.4 μW at 0.52 V.

The anode and cathode compartments of most fuel cells are separated by an ion-conducting membrane. In the most widely used $H_2$—$O_2$, cell, hydrogen is oxidized to water at the anode at a reducing potential and oxygen is reduced to water at the cathode at an oxidizing potential. In the phosphoric acid electrolyte $H_2$—$O_2$ cell, a Nafion™ membrane excludes oxygen from the anode compartment and hydrogen from the cathode compartment. (Hillman, A. R. In *Electrochemical Science and Technology of Polymers*; Linford, R. G., Ed.; Elsevier: London, 1987; p 103; *Fuel Cells and Their Applications*; Kordesch, K., Simader, G., Eds.; VCH Publisher: New York, 1996; p 384; Ormerod, R. M. Chem. Soc. Rev. 2003, 32, 17-28.) Because the anode is poised at a reducing potential with respect to the cathode, and because both the anode and the cathode comprise platinum group metal catalysts, hydrogen would be more readily oxidized at the cathode, and oxygen would be more readily reduced at the anode. As a result, the power output would be nil or negligibly small. In all but a few of the earlier reported biofuel cells, the anode and cathode compartments were also separated by an ion-exchange membrane. (Appleby, A. J.; Ng, D. Y. C.; Weinstein, H. J. Appl. Electrochem. 1971, 1, 79-90; Rao, J. R.; Richter, G.; Von Sturm. F.; Weidlich, E. Ber. Bunsen-Ges Phys Chem. 1973 77, 787-790; Wan, B. Y. C.; Tseung, A. C. C., Med. Biol. Eng. 1974, 12, 14-28; Affrossman, S.; Courtney, J. M.; Gilchrist, T.; Martin, I. Med. Biol. Eng. 1975, 13, 539-543; Turner, A. P. F.; Ramsay, G.; Higgins. I. J, Biochem Soc. Trans. 1983, 11, 445 448; Palmore, G. T.; Kim, H.-H. J Electroanal Chem 1999, 464, 110-117; Palmore. G. T.; Bertschy. H.; Bergens. S. H.; Whitesides, G. M. J. Electroanal. Chem. 1998, 443, 155-161; Sasaki, S.; Karube, L. Trends Biotechnol 1999, 17, 50-52.) In cells having platinum group metal-based $O_2$ cathodes, separation was necessary because the anodic reactant's electrooxidation products poisoned the metallic platinum group electrocatalyst of the cathode. (Appleby, A. J.; Ng, D. Y. C.; Weinstein, H. J. Appl. Electrochem. 1971, 1, 79-90; Rao, J. R.; Richter, G.; Von Sturm. F.; Weidlich, E. Ber. Bunsen-Ges Phys Chem. 1973 77, 787-790; Wan, B. Y. C.; Tseung, A. C. C., Med. Biol. Eng. 1974, 12, 14-28; Affrossman, S.; Courtney, J. M.; Gilchrist, T.; Martin, I. Med. Biol. Eng. 1975, 13, 539-543.) In cells containing a dissolved redox mediator in the anode compartment, to transport electrons from its substrate-reduced oxidase or dehydrogenase to the anode, the membrane was essential to prevent electrooxidation of the mediator at the cathode. In cells containing a dissolved redox mediator in the cathode compartment, to transport electrons from the cathode to its $O_2$-oxidized laccase or other enzyme, the membrane was essential to prevent reduction of the mediator at the anode. (Turner, A. P. F.; Ramsay, G.; Higgins. I. J, Biochem Soc. Trans. 1983, 11, 445 448; Palmore, G. T.; Kim, H.-H. J Electroanal Chem 1999, 464, 110-117; Palmore. G. T.; Bertschy. H.; Bergens. S. H.; Whitesides, G. M. J. Electroanal. Chem. 1998, 443, 155-161; Sasaki, S.; Karube, L. Trends Biotechnol 1999, 17, 50-52; Kang, C.; Xie, Y.; Auson, F. C. J. Electroanal. Chem. 1996, 413, 165-174; Pizzariello, A.; Stred'ansky, M.; Miertus, S. Bioelectrochemistry 2002, 56 99-105.)

The electrocatalysts of this study are wired enzymes. (Heller, A. Acc. Chem. Res. 1990, 23, 128-134; Heller, A. J. Phvs. Chem. B 1992, 96, 3579-3587.) They are electrostatic adducts of redox enzymes, which are polyanions at neutral pH, and electron-conducting redox polymers, which are polycations. The adduct prevents phase separation of the redox polymer and the enzyme. The redox potential of polymer I wiring the anodic enzyme (see FIG. 4), glucose oxidase (GOx), is tailored to be just slightly oxidizing with respect to the redox potential of GOx, and polymer II (see FIG. 7) wiring the cathodic enzyme, bilirubin oxidase (BOD), is just slightly reducing with respect to the potential of BOD. This provides for an electron cascade in the direction glucose→glucose oxidase→polymer I→anode→external resistance→cathode→polymer II→$O_2$, with the external resistance, rather than the kinetic resistance of any of the six electron-transfer steps, dominating the potential difference between glucose and $O_2$ (see FIG. 2). By basing the anode and cathode electrocatalysts on wired enzymes, it is possible to make both electrodes so selective for their respective reactants that the current-depleting oxidation of glucose at the cathode, and reduction of $O_2$ at the anode, are slower than the desired electrooxidation and electroreduction of reactants at their intended electrode. Beyond the key condition of selectivity, two additional conditions should be met in order to allow the elimination of the compartment-separating membrane: the readily poisoned, platinum-group, metal catalysts should be avoided, and neither compartment should contain a dissolved redox mediator. Thus, preferably, dissolved redox mediators are not present in the cell, the enzymes and redox polymers are countercharged polyelectrolytes that form bound adducts, such as electrostatic adducts, and the electrodes are selective.

In the compartment-less biofuel cell (as schematically shown in FIG. 2), the electrons of glucose reduce GOx, β-D-glucose being electrooxidized to δ-gluconolactone (see Eq. 1, above). The electrons are collected and transported to the anode via the redox polymer I shown in FIG. 4. Electrons are transported from the cathode via redox polymer II, shown in FIG. 7, to $O_2$-oxidized bilirubin oxidase, catalyzing its electroreduction of $O_2$ to water (see Eq. 2, above). The overall cell reaction is represented by (see Eq. 3, above).

The current densities of the anode and the cathode of a biofuel cell based on the wiring of enzymes are limited by the amount and the turnaround rate of the enzyme that is wired. While in the $H_2$—$O_2$ and in the methanol-air fuel cells, which can be miniaturized and chip-mounted, (Kelley, S. C.; Deluga, G. A.; Smyrl, W. H. AIChE J 2002, 48, 1071-1082) the current densities are of hundreds of milliamperes per square centimeter, the current densities of smooth wired enzyme electrodes arc only ~1 mA/cm$^2$ and reach only 2-10 mA/cm$^2$ when the electrodes are porous. Furthermore, the operational lives of the $H_2$—$O_2$ and methanol-air fuel cells are of years, while the operational lives of biofuel cells based on wiring of enzymes are ~1 week. Nevertheless, because the enzyme wiring-based cells are structurally simpler, are uniquely easy to miniaturize, and their electrodes are potentially mass-manufacturable at the same cost as glucose anodes used in glucose monitors for diabetes management (<10¢), the cells are likely to find applications. As the size of microelectronic circuits and sensors shrinks, the size of the low-power sensor-transmitter package (of potential value in physiological research and in medicine) becomes increasingly dependent on the size of its power source. The miniature biofuel cells are likely to meet the need for a small power source in low-power sensor-transmitter systems.

Earlier, progress toward a compartment-less biofuel cell anode was made by Persson and Gorton, who electrooxidized glucose on a carbon anode on which a redox mediator was chemisorbed and glucose dehydrogenase was immobilized. (Persson, B.; Gorton, L. Enzyme Microb. Technol. 1985, 7, 549-552; Persson, B.; Gorton. L.; Johansson, G. Bioelectrochem. Bioenerg. 1986, 16, 479-483.) Katz et al. reported a compartment-less enzyme-based fuel cell with an operating voltage of 60 mV and a power density of 50 nW/mm$^2$. (Katz, E.: Willner, I.; Kotlyar, A. B. J. Electroanal. Chem. 1999, 479, 64-68.) Katz et al. also proposed a "self-powered enzyme-based biosensor," in which the current passing between a glucose-transport-limited anode and a cathode, not limited by $O_2$ transport, would be indicative of the glucose concentration. However, they did not address the essential issue of the source of the power for amplifying, measuring, and transmitting the signal from such a biosensor. (Katz. E.; Buckmann. A. F.; Willner, I. J. Am. Chem. Soc. 2001, 123. 10752-10753.) Tsujimuráet al. reported a membrane-less glucose-$O_2$ biofuel cell operating in $O_2$-saturated 30 mM MOPS buffer in the presence of 50 mM glucose, producing 580 nW/mm$^2$ at an operating potential of 0.19 V. (Tsujimura, S.; Kano, K.; Ikeda, T. Electrochemistry 2002, 70, 940-942.) Chen et al. describe a compartment-less biofuel cell based on the wiring of glucose oxidase and of laccase to 7-μm-diameter, 2-cm-long carbon fiber electrodes. (Chen, T.; Barton, S. C.; Binyamin, G.; Gao. Z.; Zhang, Y.; Kim, H.-H.; Heller, A. J. Am. Chem. Soc 2001, 123, 8630-8631.) The output of their cell at 37° C. is 0.6 μW, or 1.4 μW/mm$^2$ at 0.38 V. Because their cathode is laccase-based, and because laccase loses much of its activity in 0.14 M NaCl and at pH 7.2, (Baron, S. C.; Kim, H.-H.; Binyamin, G.; Zhang, Y.; Heller, A. J. Phys. Chem. B 2001, 105, 11917-11921; Barton, S. C.; Kim, H.-H.; Binyamin, G.; Zhang, Y.; Heller, A. J. Am. Chem. Soc. 2001, 123, 5802-5803; Baron, S. C.; Pickard, M.; Vasquez-Duhalf, R.; Heller, A. Biosens Bioelectron. 2002, 17, 1071-1074; Xu, F. Appl. Biochem. Biotechnol 2001, 95, 125-133) the cell is operated at pH 5 and in the absence of chloride. Mano et al. report a laccase-comprising, compartment-less cell with an improved redox polymer connecting the reaction centers of glucose oxidase to the carbon fiber. It produces 1.2 μW, or 2.7 μW/mm$^2$, at an operating potential of 0.78 V, the highest reported for a miniature membrane-less biofuel cell. (Mano, N.; Mao, F.; Shin, W.; Chen. T.; Heller, A. Chem. Commun. 2003, 518-519.) Replacement of the laccase by bilirubin oxidase, an oxygen-electroreduction-catalyzing enzyme that maintains its activity at neutral pH and in the presence of 0.14 M NaCl, (Tsujimura, S.; Kano, K.; Ikeda, T. Electrochemistry 2002, 70, 940-942; Mano, N.; Kim, H.-H.; Zhang, Y.; Heller, A. J. Am. Chem. Soc. 2002, 124, 6480-6486; Mano, N.; Kim, H.-H.; Heller, A. J. Phys. Chem. B 2002, 106, 8842-8848; Tsujimura, S.; Tatsumi, H.; Ogawa, J.; Shimizu, S.; Kano, K.; Ikeda, T. J., Electroanal. Chem. 2001, 496, 69-75.) allows operation of the wired enzyme-based, compartment-less, biofuel cell under physiological conditions. The cell produces 1.9 μW at 37° C. under physiological conditions, or 4.3 μW/mm$^2$ at 0.52 V at 37° C. In week-long operation, it generates 0.9 J of electrical energy while passing a charge of 1.7 C. (Mano, N.; Mao, F.; Heller, A. J. Am. Chem. Soc. 2002, 124, 12962-12963.) If a zinc fiber of similar dimensions were utilized in a battery, and if the current efficiency of zinc utilization were 100%, only 0.005 C would be passed. Thus, the dimensions of a biofuel cell operating for a week can be much smaller than those of a battery. The characteristics of this membrane-less biofuel cell, which produces electrical power when implanted in a living organism (a grape), are now described.

Chemicals and Materials:

Bilirubin oxidase (BOD) (EC 1.3.3.5, 1.3 U/mg$^1$) from *Trachyderma Tsunodae* was purchased from Amano (Lombard, Ill.), and glucose oxidase (GOx) (EC 1.1.3.4, 191 U/mg$^1$) from *Aspergillus niger* was purchased from Fluka (Milwaukee, Wis. Poly(ethylene glycol) (400) diglycidyl ether (PEGDGE) from Polysciences, Inc. (Warrington, Pa.), and $NaIO_4$ and NaCl from Sigma (St. Louis, Mo.), were used as received. A fresh solution of BOD in pH 7.4, 20 mM phosphate buffer (PB) was prepared daily. All solutions were made with deionized water passed through a purification train (Sybron Chemicals Inc., Pittsburgh, Pa.). The syntheses of the BOD-wiring redox polymer II (PAA-PVI [Os(4,4'-dichloro-2,2'-bipyridine)$_2$Cl]$^{+/2+}$) (shown in FIG. 7) and the GOx-wiring redox polymer I (PVP-[Os(N,N'-alkylanated-2,2'-biimidazole)$_3$]$^{2+/3+}$) (shown in FIG. 4) were as previously reported. (Mano, N.; Kim, H.-H.; Zhang, Y.; Heller, A. J. Am. Chem. Soc. 2002, 124, 6480-6486; Mano, N.; Kim, H.-H.; Heller, A. J. Phys. Chem. B 2002, 106, 8842-8848; Mano, N.; Mao, F.; Heller, A. J. Am. Chem. Soc. 2002, 124, 12962-12963; Kim, H.-H.; Mano, N.; Zhang, Y.; Heller. A. J. Electrochem. Soc. 2003, 150, A209-A213.)

Instrumentation and Electrodes:

The measurements were performed using a bipotentiostat (CH Instruments, Austin, Tex., model CH1832) and a dedicated computer.

The 2-cm-long, 7-µm-diameter, carbon-fiber electrodes (Goodfellow, Cambridge, UK) were contacted and coated by reported procedures. (Chen, T.; Barton, S. C.; Binyamin, G.; Gao. Z.; Zhang, Y.; Kim, H.-H.; Heller, A. J. Am. Chem. Soc 2001, 123, 8630-8631; Mano, N.; Kim, H.-H.; Zhang, Y.; Heller, A. J. Am. Chem. Soc. 2002, 124, 6480-6486; Mano, N.; Kim, H.-H.; Heller, A. J. Phys. Chem. B 2002, 106, 8842-8848; Mano, N.; Mao, F.; Heller, A. J. Am. Chem. Soc. 2002, 124, 12962-12963; Kim, H.-H.; Mano, N.; Zhang, Y.; Heller. A. J. Electrochem. Soc. 2003, 150, A209-A213.) Each end of the fibers was cemented to a copper wire using conductive carbon paint (SPI, West Chester, Pa.). The carbon paint was allowed to dry and then insulated with the epoxy. The active area of each fiber was 0.44 mm$^2$. Prior to their coating, fibers were made hydrophilic by exposure to a 1-Torr $O_2$ plasma for 3 min. (Sayka, A.; Eberhart, J. G. Solid-State Technol. 1989, 32, 69-70.) The cathodic catalyst was made, as described, of 44.6 wt % bilirubin oxidase, 48.5 wt % polymer II, and 6.9 wt % of the cross-linker PEGDGE. (Mano, N.; Kim, H.-H.; Zhang, Y.; Heller, A. J. Am. Chem. Soc. 2002, 124, 6480-6486; Mano, N.; Kim, H.-H.; Heller, A. J. Phys. Chem. B 2002, 106, 8842-8848; Mano, N.; Mao, F.; Heller, A. J. Am. Chem. Soc. 2002, 124, 12962-12963.) The anodic catalyst solution was made as follows: 100 µL of 40 mg/mL of GOx in 0.1 M NaHCO$_3$ was oxidized by 50 µL, of 7 mg/mL of NaIO$_4$ in the dark for 1 h, and then 2 µL of the periodate-oxidized GOx was mixed with 8 µL of 10 mg/mL of polymer I and a 0.5-µL droplet of 2.5 mg/mL of PEGDGE. A 5-µL, aliquot of this solution was applied to the carbon fiber. The resulting anodic catalyst consisted of the cross-linked adduct of 39.6 wt 9% GOx, 59.5 wt % polymer I, and 0.9 wt % PEGDGE. The glucose concentration was determined by using a FreeStyle™ blood glucose monitor (TheraSense Inc., Alameda, Calif.). The bulk cell used for the characterization of the electrodes in vitro had an Ag/AgCl (3 M KCl) reference electrode and a platinum wire counter electrode (BAS, West Lafayette, Ind.).

Implantation in the Grape:

The fibers were implanted by making a pair of 2-cm-long cuts with a razor blade, so as to create a triangular groove and allow temporary removal of the cut part. After the fiber was implanted, the cut part was replaced in its groove.

Results:

FIG. 12A shows the polarization curves of the 7-µm carbon fiber anode [modified with wired GOx (bold line)] and of the fiber cathode [modified with wired BOD (fine line)], in a quiescent 15 mM glucose solution in air at 37° C. in pH 7.2, 0.1 M NaCl and 20 mM phosphate buffer solution. Catalytic electrooxidation of glucose was observed at −0.2 V vs Ag/AgCl, and it reached its plateau of 10 µA/mm$^2$ near −0.1 V vs Ag/AgCl. Catalytic electroreduction of $O_2$ was observed at +0.48 V vs Ag/AgCl and reached its 9.5 µA/mm$^2$ plateau near +0.35 V vs Ag/AgCl.

FIG. 12B shows the power density of the biofuel cell at 25° C. (fine line) and at 37° C. (bold line). The dependence of the power output on the cell voltage in air (bold line) and under $O_2$ (fine line) is shown in FIG. 13A. In the quiescent PBS buffer, the power density at 1 atm $O_2$ was 30% lower than that in air. FIG. 13B shows the dependence of the power density on the glucose concentration in air (●) and under $O_2$ (○). The current density increased with the glucose concentration up to 20 mM, where a plateau of 4.4 µW/mm$^2$ was reached in air and a plateau of 3.4 µW/mm$^2$ was reached under $O_2$. At 2 mM glucose concentration, the power density was 80% lower under $O_2$ than it was in air; at 35 mM glucose concentration, it was 35% lower under $O_2$ than it was in air. FIG. 14 shows the temperature dependence of the power density for the cell operating at +0.52 V in a quiescent solution in air at 37° C. in a pH 7.2, 0.14 M NaCl, 20 mM phosphate, and 15 mM glucose solution. The power density increased with temperature, reaching a plateau at 40° C., and then declined above 50° C.

The pH dependence of the power density for the cell operating at +0.52 V is seen in FIG. 15A. The power density increased with pH, reaching a plateau at pH 6.2, and then declined slowly above pH 8.4. The NaCl concentration dependence of the power density for the cell operating at +0.52 V is shown in FIG. 15B. The power was nearly independent of the NaCl concentration through the 0-0.1 M range and then declined, dropping at 1 M NaCl to one-fifth of its value at 0.1 M NaCl.

No power was produced when the fibers were implanted in a grasshopper. Implantation of the fibers in a grape (>30 mM glucose, pH 5.4), however, did yield an operating biofuel cell. FIG. 16A shows a photograph of the sliced grape and the contacts of the implanted fibers. Because the fibers of 7-µm diameter were barely visible in the photograph, lines representing their positions were drawn. The dependence of the power density on the operating voltage is shown in FIG. 16B. The power output of the cell depended on the position of the cathode fiber. When the cathode fiber was located near the center of the grape, the power density was 0.47 µW/mm$^2$; when the cathode fiber was near the skin of the grape, the power density was 2.4 µW/mm$^2$. Alter 24 h of continuous operation, 85% of the initial power output was retained.

The reversible redox potential of GOx from A. niger at pH 7.4 is −0.35 vs Ag/AgCl, (Hirose, J.; Inoue, T.; Sakuragi, H.; Kikkawa, M.; Minakami, M.; Morikawa, T.; Iwarnoto, H.; Hiromi, K. Inorg. Chim. Acta 1998, 273, 204-212.) and that of BOD from T. Tsunodae is about +0.36 vs Ag/AgCl (Hirose, J.; Inoue, T.; Sakuragi, H.; Kikkawa, M.; Minakami, M.; Morikawa, T.; Iwamoto, H.; Hiromi, K. Inorg. Chim. Acta 1998, 273, 204-212.) (as schematically shown in FIG. 17). Thus, the redox potentials of GOx and BOD differ by 0.71 V. This value, representing the limit of the operating voltage of the cell, is close to the difference between the observed threshold potentials for electrooxidation of glucose (−0.20 V vs Ag/AgCl) and electroreduction of oxygen +0.48 V vs Ag/AgCl). Concentration polarization and overpotentials for the six electron-transfer steps of the anode and the cathode (as schematically shown in FIG. 1) decrease the operating voltage at the point of maximum power to 0.52 V.

Redox polymer I (FIG. 4), connecting the GOx reaction centers to the anode fiber, enables the electrooxidation of glucose at −100 mV vs Ag/AgCl at a current density of 1.1 mA/cm$^2$ (FIG. 12A, bold line), (Mano, N.; Mao, F.; Heller, A. J. Am. Chem. Soc. 2002, 124, 12962-12963; Mao, F.; Mano, N.; Heller, A. J. Am. Chem. Soc. 2003, 125, 4951-4957.) a potential only 260 mV oxidizing versus the estimated GOx redox potential at pH 7.3. (Stankovich, M. T.; Schopfer, L. M.; Massey, V. J. Biol. Chem. 1978, 253, 4971-4979.) It differs from the earlier redox polymer (Kim, H.-H.; Mano, N.; Zhang, Y.; Heller. A. J. Electrochem. Soc. 2003, 150, A209-A213) in its redox center and in the tethering of it, redox centers to the polymer backbone through a 13-atom-long flexible spacer arm. The redox potential of its [Os(:N, N'-alkylated-2,2'-bi-imidazole)$^{2+/3+}$] redox center is −190 mV vs Ag/AgCl, about 0.8 V reducing relative to that of the familiar Os(bpy)$_3^{2+/3+}$ Complex. (Mano, N.; Mao, F.; Heller, A. J. Am. Chem. Soc. 2002, 124, 12962-12963; Mao, F.;

Mano, N.; Heller, A. J. Am. Chem. Soc. 2003, 125, 4951-4957.) Although the potential difference between the GOx redox centers and the redox polymer is only 170 mV, the polymer effectively wires the enzyme redox centers. The long tether binding the redox centers to the backbone reduces the overvoltage for driving the electrons from the GOx-FADH$_2$ centers to the redox polymer and through the polymer to the electrode. It provides for close approach of the redox centers of the polymer and of the enzyme and facilitates collisional electron transfer between neighboring polymer redox centers, as the tethered centers "wipe" the electrons from large overlapping proximal volumes of the hydrated cross-linked redox polymer. (Mano, N.; Mao, F.; Heller, A. J. Am. Chem. Soc. 2002, 124, 12962-12963.)

Redox polymer II (FIG. 7) is an electron-conducting redox copolymer of polyacrylamide and poly(N-vinylimidazole) complexed with $[Os(4,4'\text{-dichloro-2,2'-bipyridine})_2Cl]^{+/2+}$ (Mano, N.; Kim, H.-H.; Zhang, Y.; Heller, A. J. Am. Chem. Soc. 2002, 124, 6480-6486; Mano, N.; Kim, H.-H.; Heller, A. J. Phys. Chem. B 2002, 106, 8842-8848; Mano, N.; Mao, F.; Heller, A. J. Am. Chem. Soc. 2002, 124, 12962-12963.) It electrically wires the BOD $Cu^{+/2+}$ centers to the cathode fiber. As illustrated in FIG. 12A (fine line), the overpotential for oxygen reduction to water is remarkably low. Even though the oxygen concentration in air-saturated pH7 phosphate buffer is only about 0.1 mM, the current density of the oxygen cathode reaches 1.1 mA/cm$^2$ at −140 mV vs the potential of the reversible $O_2/H_2O$ couple. (Mano, N.; Kim, H.-H.; Zhang, Y.; Heller, A. J. Am. Chem. Soc. 2002, 124, 6480-6486; Mano, N.; Kim, H.-H.; Heller, A. J. Phys. Chem. B 2002, 106, 8842-8848.) Glucose is not electrooxidized on the cathode poised at +0.4 V vs Ag/AgCl.

When the anode and cathode fibers are of equal length, the currents of the two are equal when the anode is poised at −0.19 V vs Ag/AgCl and the cathode at +0.34 mV vs Ag/AgCl, the cell operating at +0.52 V (FIG. 12B). In a quiescent physiological buffer solution, the power output is 2.8 μW/mm$^2$ at 25° C. (FIG. 12B, fine line) and 4.4 μW/mm$^2$ at 37° C. (FIG. 12B, bold line).

Oxygen Pressure Dependence:

At low partial pressures of $O_2$, where electroreduction of $O_2$ to water is $O_2$ mass-transport-limited in the quiescent solution, the power increases with the partial pressure of $O_2$ until the kinetic limit of the cathodic electrocatalyst is reached. As the $O_2$ partial pressure is increased, the anodic glucose electrooxidation current decreases, because $O_2$ competes with the wire for GOx FADH$_2$ electrons (see Eqs. 5 and 6 below). As can be seen in FIG. 13A, at 37° C. and 15 mM glucose concentration, switching the bubbled gas from air to oxygen results in the loss of one-third of the power when the cell operates at 0.52 V.

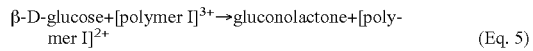

(Eq. 5)

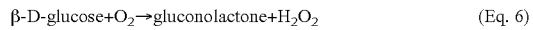

(Eq. 6)

As illustrated in FIG. 13B, the loss depends on the glucose concentration. Although above 15 mM glucose concentration about one-third of the power is lost when the atmosphere is switched from air to oxygen, the loss is much greater, four-fifths of the output, at 2 mM glucose concentration. The difference is attributed to the slower electrooxidation of the solution side of the film than its electrode side. At high glucose concentration, the glucose-reduced front moves toward the electrode, and the effective kinetic resistance is reduced. Excessive loss of current by electroreduction of $O_2$ at the glucose-oxidizing anode is avoided because of the rapid diffusion of electrons in GOx wiring redox polymer I (FIG. 4); the apparent electron diffusion coefficient is as high as 5.8× 10$^{-6}$ cm$^2$/s. (Mano, N.; Mao, F.; Heller, A. J. Am. Chem. Soc. 2002, 124, 12962-12963; Mao, F.; Mano, N.; Heller, A. J. Am. Chem. Soc. 2003, 125, 4951-4957.) The redox centers of the film are rapidly electrooxidized even at −0.1 V vs Ag/AgCl, and in an aerated solution, most of the electrons of GOx are captured by polymer I rather than by dissolved $O_2$.

While the $H_2O_2$ produced in the competing side reaction of $O_2$ with reduced glucose oxidase could damage the glucose electrooxidizing anode if the $H_2O_2$ were allowed to accumulate, the damage it causes to the anode when diluted or decomposed by catalase, an abundant enzyme in many organisms, is not significant. (Binyamin, G.; Heller, A. J. Electrochem. Soc. 1999, 146, 2965-2967.)

Temperature Dependence:

The temperature dependence of the cell operating at 0.52 V at 15 mM glucose concentration in a quiescent PBS buffer solution in air and at 37° C. is seen in FIG. 14. The power density increases up to 50° C. and then declines rapidly as one or both of the enzymes are denatured. The activation energies are 28.3 kJ/mol for the anode reaction (Mano, N.; Mao, F.; Heller, A. J. Am. Chem. Soc. 2002, 124, 12962-12963.) and 34.3 kJ/mol[1] for the cathode reaction. (Mano, N.; Kim, H.-H.; Zhang, Y.; Heller, A. J. Am. Chem. Soc. 2002, 124, 6480-6486.) At ambient temperature, the power density is limited by the kinetics of the cathodic bioelectrocatalyst. The observed activation energy for the thermal denaturing of bilirubin oxidase is 88.2 kJ/mol[1], and for glucose oxidase it is 96 kJ/mol. (Mano, N.; Kim, H.-H.; Zhang, Y.; Heller, A. J. Am. Chem. Soc. 2002, 124, 6480-6486; Mano, N.; Mao, F.; Heller, A. Unpublished results, 2003.) Even though the activation energy for denaturing glucose oxidase is higher, it is the denaturing of bilirubin oxidase (Mano, N.; Kim, H.-H.; Zhang, Y.; Heller, A. J. Am. Chem. Soc. 2002, 124, 6480-6486.) that causes the observed decline from 4.5 to 3.45 μW/mm$^2$ upon increasing the temperature from 45 to 55° C. at a rate of 10° C./h, because in this temperature domain the power output is controlled by the cathode in the 15 mM aerated glucose solution. Because both enzymes are denatured and the activation energy for the denaturing of GOx exceeds that of BOD, (Mano, N.; Kim, H.-H.; Zhang, Y.; Heller, A. J. Am. Chem. Soc. 2002, 124, 6480-6486; Mano, N.; Mao, F.; Heller, A. Unpublished results, 2003.) at temperatures above 55° C. the cell becomes anode-limited, and heating at a rate of 10° C./h from 55 to 60° C. causes the power to drop rapidly, from 3.45 to 2.0 μW/mm$^2$.

pH Dependence:

FIG. 15A shows the pH dependence of the power density when the cell operates at +0.52 V in air. The current density of the anode is near its maximum between pH 6 and 8.2. (Mano, N.; Mao, F.; Heller, A. Unpublished results, 2003.) The current density of the cathode is nearly independent of pH in the pH 6-10.5 range. (Mano, N.; Kim, H.-H.; Zhang, Y.; Heller, A. J. Am. Chem. Soc. 2002, 124, 6480-6486; Mano, N.; Kim, H.-H.; Heller, A. J. Phys. Chem. B 2002, 106, 8842-8848.) At pH<6, (Mano, N.; Kim, H.-H.; Zhang, Y.; Heller, A. J. Am. Chem. Soc. 2002, 124, 6480-6486; Mano, N.; Kim, H.-H.; Heller, A. J. Phys. Chem. B 2002, 106, 8842-8848; Mano, N.; Mao, F.; Heller, A. Unpublished results, 2003.) the power is limited by the kinetics of the anode; at pH 5, where the current density of the anode is 2.0 μA/mm$^2$ and that of the cathode is 4.5 μA/mm$^2$, the power density drops to 1.0 μW/mm$^2$. As the pH is raised to pH 6, the kinetics of the anode improves and, as shown in FIG. 15A, the power density increases. (Mano, N.; Mao, F.; Heller, A. Unpublished results, 2003.) Above pH 6, the current of the cathode is lower than that of the anode. At pH 7, (Mano, N.; Mao, F.; Heller, A. J. Am. Chem. Soc. 2002, 124, 12962-12963.) where the anode current density is 12 µA/mm$^2$ and the cathode current density is 10 µA/mm$^2$, the cathode controls the power. Thus, the optimal operating pH for the cell consisting of two carbon fibers of equal length is 6. Above pH 8.4, the power decreases because of denaturation of bilirubin oxidase. (Mano, N.; Kim, H.-H.; Zhang, Y.; Heller, A. J. Am. Chem. Soc. 2002, 124, 6480-6486; Mano, N.; Kim, H.-H.; Heller, A. J. Phys. Chem. B 2002, 106, 8842-8848. In the pH range of human serum or blood (pH 7.1-7.4), the variation in power is negligibly small.

Effect of NaCl:

Serum, blood, and other physiological fluids contain 0.14 M chloride. Copper-binding anions, particularly halide anions, inhibit multi-copper oxidases. In addition, the electrostatic bond between the polyanionic enzyme and the polycationic redox polymer, which prevents their phase separation, is weakened at high ionic strength, where the enzyme and polymer charges are screened by their respective counterions. (Heller, A. J. Phys. Chem. B 1992, 96, 3579-3587; Degani, Y.; Heller, A. J. Am. Chem. Soc. 1989, 111, 2357-2358; Katakis, I.; Ye, L.; Heller, A. J. Am. Chem. Soc. 1994, 116, 3617-3618.) At greater cross-linking, the phase separation is reduced. The dependence of the power output on the NaCl concentration is seen in FIG. 15B. Above 0.15 M, the anodic current monotonically declines upon increasing the NaCl concentration. Because increasing the salt concentration from 0.1 to 1 M decreases the current density of the wired BOD cathode only by 2%, (Mano, N.; Kim, H.-H.; Zhang, Y.; Heller, A. J. Am. Chem. Soc. 2002, 124, 6480-6486; Mano, N.; Kim, H.-H.; Heller, A. J. Phys. Chem. B 2002, 106, 8842-8848) the decrease in the power output is attributed to the partial unwiring of the GOx. (Mano, N.; Mao, F.; Heller, A. Unpublished results, 2003.)

Operation in the Grape:

For the experiment demonstrating that the cell consisting merely of two coated carbon fibers actually operates in a living organism, the cell was implanted in a grasshopper and in a grape. In the grasshopper, no power was produced. As we learned later, the sugar in the fluid of the grasshopper is not glucose but the disaccharide trehalose. (Harrison, R. R.; Koch, C. Analog Integr. Circuits Signal Process 2000, 24, 213-216.) Power was produced, however, in the grape, a fruit having a high (>30 mM) glucose concentration in its sap. The power output of the cell functioning in the grape was $O_2$-transport-controlled and depended on the position of the cathode fiber. When the cathode fiber was near the center of the grape, where the fruit was oxygen-deficient, the power density was only µW/mm$^2$ at 0.52 V. When the fiber was shallowly implanted near the skin of the grape, where the sap was better oxygenated, the power density was 2.4 µW/mm$^2$ at 0.52 V.

Conclusion:

The area of the electrodes of the compartment-less, glucose-$O_2$ biofuel cell, consisting of two electrocatalyst-coated 7-µm diameter, 2-cm long carbon fibers, is 180 times smaller, its operating voltage is 8 times higher (0.52 vs 0.06 V), and its power density 12 times higher (4.3 vs 0.35 µW/mm$^2$) than those of an earlier reported compartment-less, glucose-$O_2$ cell which also operated under physiological conditions. (Katz, E.: Willner, I.; Kotlyar, A. B. J. Electroanal. Chem. 1999, 479, 64-68.) At neutral pH, where the power output of the cell is cathode-limited, the activation energy for power increase is 34.3 kJ/mol. Above 50° C., the decline is caused by the thermal denaturing of bilirubin oxidase, having an activation energy of 88.2 kJ/mol[1]. When the lengths of the anode and cathode fibers are the same, the power output is limited in the aerated solution below pH 6 by the anode and above pH 6 by the cathode. In the pH range of human serum or blood, the variation of power output is negligibly small. The power output does not vary substantially with NaCl concentration in the 0.05-0.15 M range; in the 0.15-1 M range, it declines as the NaCl concentration is raised. The cell operates continuously at 37° C. in an aerated, glucose-containing physiological (pH 7.2, 0.14 NaCl, 20 mM phosphate) buffer for a week, (Pizzariello, A.; Stred'ansky, M.; Miertus, S. Bioelectrochemistry 2002, 56 99-105.) and, as shown here, it retains 85% of its initial power output of 1.1 µW after operating for a day in a living organism, a grape. The power output of the cell at 37° C. in a physiological buffer solution is 1.9 µW, sufficient for powering low-power CMOS circuits, (Harada, M.; Tsukahara, T.; Kodate, J.; Yamagishi, A.; Yamada, L IEEE. J. Solid State Circuits 2000, 15, 2000-2004.) and its operating voltage of 0.52 V is adequate for operation of low-voltage CMOS/SIMOX integrated circuits. It is hoped, that after considerable further development, the simple and disposable cell will power implanted autonomous sensor-transmitter systems of relevance to physiological research and medicine. These miniature systems would operate for about a week to monitor, for example, the temperature at a site following surgery, indicative of inflammation.

As described herein, the present invention provides power sources, or fuel cells, capable of operating without a membrane, such that their size can be reduced to a sub mm$^2$ footprint and a sub-mm$^3$ volume, for example. This reduced size is of great advantage for a variety of applications, such as applications calling for the implantation of fuel cells in biological systems.

In fuel cells of the present invention, the rate of electrooxidation of fuel at the wired cathode of the cell is much slower than the rate of oxygen electroreduction, and the rate of oxygen electroreduction at the wired anode of the cell is much slower than the rate of fuel electrooxidation, such that no membrane is required. Thus, the fuel cell of the present invention can operate with the anode and the cathode in the same compartment, in the presence of both oxygen and the fuel of the cell, such as glucose.

Not only can the fuel cell operate without cumbersome components, such as membranes, seals and cases, it can do so effectively. For example, according to one aspect of the invention, the fuel cell of the present invention can produce a current density of from about 0.1 to about 10 mA/cm$^2$. In addition, the effective fuel cell of the present invention can be manufactured relatively inexpensively, such as on the order of about 10¢ per cell. The very low cost of the inventive fuel cells is a particular advantage with respect to applications that call for fuel cells having a short life span, such as disposable fuel cells used in biological systems for medical purposes, which may be in use for only a week, or even less.

The fuel cell of the present invention is further advantageous in that it can operate under physiological conditions. As such, the biofuel cell of the present invention may be used within a biological system, such as a human body. For example, according to an embodiment of the invention, the biofuel cell electrooxidizes oxidizable components of a body fluid within a human, such as glucose in a diabetic, and electroreduces oxygen within that fluid. Power is generated in the biofuel cell via the electrooxidation and electroreduction occurring in the same fluid. Advantageously, this biofuel cell is small, effective, powerful, and easy and inexpensive to manufacture.

Various references, publications, and provisional and non-provisional United States patent applications, have been identified herein, each of which is incorporated herein in its entirety by this reference. Various aspects and features of the present invention have been explained or described in relation to beliefs or theories, although it will be understood that the invention is not bound to any particular belief or theory. Various modifications, processes, as well as numerous structures to which the present invention may be applicable will be readily apparent to those of skill in the art to which the present invention is directed, upon review of the specification. Although the various aspects and features of the present invention have been described with respect to various embodiments and specific examples herein, it will be understood that the invention is entitled to protection within the full scope of the appended claims.

The invention claimed is:

1. A fuel cell comprising:
   an anode comprising a first redox polymer and a first enzyme disposed on the surface of the anode for electrooxidizing an analyte and delivering electrons at the anode to generate a current;
   a cathode comprising a second redox polymer and a second enzyme disposed on the surface of the cathode; and
   an electrically insulating separator positioned between and in contact with the anode and cathode, wherein the insulating separator is capable of being penetrated by blood or interstitial fluid,
   wherein the anode and the cathode are in electrical communication.

2. The fuel cell of claim 1, wherein the second enzyme is a copper-containing enzyme.

3. The fuel cell of claim 2, wherein the second enzyme comprises four copper ions per functional unit thereof.

4. The fuel cell of claim 1, wherein the second enzyme is laccase, ascorbate oxidase, ceruloplasmine, or bilirubin oxidase.

5. The fuel cell of claim 1, wherein each of the potential differences between the anode and the first redox polymer, the first redox polymer and the first enzyme, the cathode and the second redox polymer, the second redox polymer and the second enzyme, is from about 10 mV to about 200 mV.

6. The fuel cell of claim 1, wherein the cathode comprises platinum.

7. The fuel cell of claim 1, wherein the cathode comprises carbon.

8. The fuel cell of claim 1, wherein the first enzyme is a glucose-responsive enzyme.

9. The fuel cell of claim 8, wherein the glucose-responsive enzyme is glucose oxidase or glucose dehydrogenase.

10. The fuel cell of claim 1, wherein the first redox polymer comprises at least one redox mediator.

11. The fuel cell of claim 10, wherein the redox mediator comprises ruthenium or osmium.

12. The fuel cell of claim 1, wherein at least a portion of the fuel cell is configured to be positioned subcutaneously in a subject.

13. The fuel cell of claim 1, wherein the anode is positioned on a first side of the electrically insulating separator and the cathode is positioned on an opposite side of the electrically insulating separator from the anode.

14. The fuel cell of claim 1, further comprising a substrate, wherein the anode and cathode are positioned coplanar on a substrate.

15. The fuel cell of claim 4, wherein the second enzyme is an enzyme selected from the group consisting of ascorbate oxidase, a ceruloplasmine and a bilirubin oxidase.

* * * * *